US012652952B2

(12) United States Patent
Ohsawa et al.

(10) Patent No.: US 12,652,952 B2
(45) Date of Patent: Jun. 9, 2026

(54) LIGHT-EMITTING DEVICE, LIGHT-EMITTING APPARATUS, ELECTRONIC APPARATUS, AND LIGHTING DEVICE

(71) Applicant: SEMICONDUCTOR ENERGY LABORATORY CO., LTD., Atsugi (JP)

(72) Inventors: Nobuharu Ohsawa, Zama (JP); Satoshi Seo, Sagamihara (JP); Takeyoshi Watabe, Atsugi (JP); Airi Ueda, Sagamihara (JP); Tomohiro Kubota, Atsugi (JP); Takashi Hirahara, Atsugi (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 1323 days.

(21) Appl. No.: 17/412,450

(22) Filed: Aug. 26, 2021

(65) Prior Publication Data

US 2022/0077391 A1 Mar. 10, 2022

(30) Foreign Application Priority Data

Sep. 4, 2020 (JP) ................................ 2020-149062
Jan. 28, 2021 (JP) ................................ 2021-011706

(51) Int. Cl.
*H01L 51/00* (2006.01)
*C07C 211/61* (2006.01)
(Continued)

(52) U.S. Cl.
CPC .......... *H10K 85/633* (2023.02); *C07C 211/61* (2013.01); *C07C 2601/14* (2017.05);
(Continued)

(58) Field of Classification Search
None
See application file for complete search history.

(56) References Cited

U.S. PATENT DOCUMENTS 8,642,190 B2 2/2014 Ogita et al.
9,051,239 B2 6/2015 Osaka et al.
(Continued)

FOREIGN PATENT DOCUMENTS

CN 102437290 A 5/2012
CN 110240546 A 9/2019
(Continued)

OTHER PUBLICATIONS

Machine English translation of Shimamura et al. (JP 11-162649 A). Feb. 2, 2026.*
(Continued)

*Primary Examiner* — Jay Yang
(74) *Attorney, Agent, or Firm* — Fish & Richardson P.C.

(57) ABSTRACT

A light-emitting device with high emission efficiency and low driving voltage is provided. A light-emitting apparatus, an electronic device, and a lighting device with low power consumption are provided. The following organic compound is provided: the organic compound has an arylamine structure; and when the organic compound is deposited to be a film, the ordinary refractive index of the deposited film with respect to light with a wavelength of 458 nm is greater than or equal to 1.50 and less than or equal to 1.75, the birefringence Δn of the deposited film with respect to light with a wavelength of 458 nm is greater than or equal to 0 and less than or equal to 0.008, or the alignment order parameter of the deposited film with respect to light with a wavelength corresponding to the longest wavelength where an absorption peak appears in the absorption spectrum is greater than or equal to −0.07 and less than or equal to 0.00.

48 Claims, 32 Drawing Sheets

(51) Int. Cl.

| | |
|---|---|
| ***H10K 85/60*** | (2023.01) |
| *H10K 50/15* | (2023.01) |
| *H10K 50/17* | (2023.01) |
| *H10K 59/12* | (2023.01) |
| *H10K 59/80* | (2023.01) |

(52) U.S. Cl.

CPC .......... *C07C 2603/18* (2017.05); *H10K 50/15* (2023.02); *H10K 50/17* (2023.02); *H10K 59/12* (2023.02); *H10K 59/874* (2023.02); *H10K 59/876* (2023.02); *H10K 85/615* (2023.02)

(56) References Cited

U.S. PATENT DOCUMENTS

| | | | |
|---|---|---|---|
| 9,496,503 | B2 | 11/2016 | Takeda et al. |
| 9,634,263 | B2 | 4/2017 | Ogita et al. |
| 9,818,984 | B2 | 11/2017 | Mizuno |
| 10,556,864 | B2 | 2/2020 | Nomura et al. |
| 10,941,108 | B2 | 3/2021 | Jeong et al. |
| 11,964,928 | B2 | 4/2024 | Kubota et al. |
| 12,139,446 | B2 | 11/2024 | Seo et al. |
| 12,460,130 | B2 | 11/2025 | Kubota et al. |
| 2009/0160323 | A1 | 6/2009 | Nomura et al. |
| 2010/0104969 | A1 | 4/2010 | Mochizuki et al. |
| 2015/0207075 | A1 | 7/2015 | Mujica-fernaud. et al. |
| 2016/0111653 | A1 | 4/2016 | Itoi |
| 2018/0009751 | A1 | 1/2018 | Nomura et al. |
| 2019/0016666 | A1 | 1/2019 | Jeong et al. |
| 2020/0176692 | A1 | 6/2020 | Watabe et al. |
| 2020/0235297 | A1 | 7/2020 | Miyake et al. |
| 2021/0005814 | A1 | 1/2021 | Watabe et al. |
| 2021/0202843 | A1 | 7/2021 | Qian et al. |
| 2022/0158095 | A1 | 5/2022 | Huang et al. |

FOREIGN PATENT DOCUMENTS

| | | | |
|---|---|---|---|
| CN | 110373183 | A | 10/2019 |
| CN | 110950762 | A | 4/2020 |
| CN | 111233764 | A | 6/2020 |
| CN | 111533716 | A | 8/2020 |
| CN | 111548278 | A | 8/2020 |
| JP | 11-162649 | A | 6/1999 |
| JP | 11-282181 | A | 10/1999 |
| JP | 2005-120030 | A | 5/2005 |
| JP | 2009-091304 | A | 4/2009 |
| JP | 2014-207356 | A | 10/2014 |
| JP | 2018-181916 | A | 11/2018 |
| JP | 2019-505566 | | 2/2019 |
| KR | 2016-0127429 | A | 11/2016 |
| KR | 2017-0080432 | A | 7/2017 |
| KR | 2018-0137315 | A | 12/2018 |
| KR | 2020-0092211 | A | 8/2020 |
| WO | WO-2017/116167 | | 7/2017 |
| WO | WO-2017/116168 | | 7/2017 |
| WO | WO-2019/220276 | | 11/2019 |
| WO | WO-2020/259078 | | 12/2020 |

OTHER PUBLICATIONS

Taiwanese Office Action (Application No. 110131649) dated Dec. 31, 2024.

Lee.J et al., "Synergetic electrode architecture for efficient graphene-based flexible organic light-emitting diodes", Nature Communications, Jun. 2, 2016, vol. 7, pp. 11791-1-11791-9.

* cited by examiner

LIGHT-EMITTING DEVICE, LIGHT-EMITTING APPARATUS, ELECTRONIC APPARATUS, AND LIGHTING DEVICE

BACKGROUND OF THE INVENTION

1. Field of the Invention

One embodiment of the present invention relates to an organic compound, a light-emitting element, a light-emitting device, a display module, a lighting module, a display device, a light-emitting apparatus, an electronic apparatus, a lighting device, and an electronic device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

2. Description of the Related Art

Light-emitting devices (organic EL devices) including organic compounds and utilizing electroluminescence (EL) have been put to more practical use. In the basic structure of such light-emitting devices, an organic compound layer containing a light-emitting material (an EL layer) is interposed between a pair of electrodes. Carriers are injected by application of voltage to the device, and recombination energy of the carriers is used, whereby light emission can be obtained from the light-emitting material.

Such light-emitting devices are of self-luminous type and thus have advantages over liquid crystal displays, such as high visibility and no need for backlight when used as pixels of a display, and are particularly suitable for flat panel displays. Displays including such light-emitting devices are also highly advantageous in that they can be thin and lightweight. Moreover, such light-emitting devices also have a feature that response speed is extremely fast.

Since light-emitting layers of such light-emitting devices can be successively formed in a planar shape, planar light emission can be achieved. This feature is difficult to realize with point light sources typified by incandescent lamps and light-emitting diodes (LEDs) or linear light sources typified by fluorescent lamps; thus, the light-emitting devices also have great potential as planar light sources, which can be used for lighting devices and the like.

Displays or lighting devices including light-emitting devices are suitable for a variety of electronic apparatuses as described above, and research and development of light-emitting devices have progressed for more favorable characteristics.

Low outcoupling efficiency is often a problem in an organic EL device. To improve outcoupling efficiency and external quantum efficiency, a structure in which a layer including a low-refractive-index material is formed inside an EL layer is proposed (e.g., Patent Document 1).

REFERENCE

[Patent Document 1] United States Patent Application Publication No. 2020/0176692

SUMMARY OF THE INVENTION

It is possible to improve the outcoupling efficiency when the low-refractive-index layer is provided inside the organic EL device as described above; however, there is generally a trade-off relationship between a high carrier-transport property and a low refractive index. This is because the carrier-transport property of an organic compound largely depends on an unsaturated bond, and an organic compound having many unsaturated bonds tends to have a high refractive index.

In order to obtain an organic compound with a low refractive index, a substituent with low molecular refraction (e.g., a saturated hydrocarbon group or a cyclic saturated hydrocarbon group) is preferably introduced into a molecule of the organic compound; however, the substituent might inhibit the movement of carriers to decrease the carrier-transport property.

When an organic EL device is manufactured using a material with a low carrier-transport property, the driving voltage of the EL device is increased, so that the power consumption is increased. The amount of power consumption of an organic EL device is extremely important because a battery is often used to drive the organic EL device owing to its features of being thin and lightweight.

In view of the above, an object of one embodiment of the present invention is to provide an organic compound that has a low refractive index and can inhibit an increase in driving voltage even when used in an EL device.

Another object of one embodiment of the present invention is to provide an organic compound with which a light-emitting device with high emission efficiency and low driving voltage can be manufactured. Another object of one embodiment of the present invention is to provide a light-emitting device with high emission efficiency and low driving voltage. Another object of one embodiment of the present invention is to provide any of a light-emitting device, a light-emitting apparatus, an electronic apparatus, a display device, and an electronic device each having low power consumption.

It is only necessary that at least one of the above-described objects be achieved in the present invention.

One embodiment of the present invention is a light-emitting device including an anode, a cathode, and an EL layer between the anode and the cathode. The EL layer includes a light-emitting layer and a hole-transport region. The hole-transport region is between the anode and the light-emitting layer. The hole-transport region includes an organic compound having an arylamine structure. When the organic compound is deposited as a film, the ordinary refractive index of the deposited film with respect to light with a wavelength of 458 nm is greater than or equal to 1.50 and less than or equal to 1.75, and the birefringence $\Delta n$ of the deposited film with respect to light with a wavelength of 458 nm is greater than or equal to 0 and less than or equal to 0.008.

Another embodiment of the present invention is a light-emitting device including an anode, a cathode, and an EL layer between the anode and the cathode. The EL layer includes a light-emitting layer and a hole-transport region. The hole-transport region is between the anode and the light-emitting layer. The hole-transport region includes an organic compound having an arylamine structure. When the organic compound is deposited as a film, the ordinary refractive index of the deposited film with respect to light with a wavelength of 458 nm is greater than or equal to 1.50 and less than or equal to 1.75, and the alignment order parameter of the deposited film with respect to light with a wavelength corresponding to the longest wavelength where an absorption peak appears in an absorption spectrum is greater than or equal to −0.07 and less than or equal to 0.00.

Another embodiment of the present invention is the light-emitting device with the above structure, in which a group including a para-biphenyl structure is bonded to at least one of nitrogen atoms of amine of the arylamine structure in the organic compound.

Another embodiment of the present invention is a light-emitting device including an anode, a cathode, and an EL layer between the anode and the cathode. The EL layer includes a light-emitting layer and a hole-transport region. The hole-transport region is between the anode and the light-emitting layer. The hole-transport region includes an organic compound having an arylamine structure. When the organic compound is deposited as a film, the ordinary refractive index of the deposited film with respect to light with a wavelength of 458 nm is greater than or equal to 1.50 and less than or equal to 1.75, and the birefringence Δn of the deposited film with respect to light with a wavelength of 458 nm is greater than or equal to 0 and less than or equal to 0.04. A 1,1'-biphenyl-4-yl group is bonded to a nitrogen atom of amine in the organic compound.

Another embodiment of the present invention is a light-emitting device including an anode, a cathode, and an EL layer between the anode and the cathode. The EL layer includes a light-emitting layer and a hole-transport region. The hole-transport region is between the anode and the light-emitting layer. The hole-transport region includes an organic compound having an arylamine structure. When the organic compound is deposited as a film, the ordinary refractive index of the deposited film with respect to light with a wavelength of 458 nm is greater than or equal to 1.50 and less than or equal to 1.75, and the alignment order parameter of the deposited film with respect to light with a wavelength corresponding to the longest wavelength where an absorption peak appears in the absorption spectrum is greater than or equal to −0.10 and less than or equal to 0.00. A 1,1'-biphenyl-4-yl group is bonded to a nitrogen atom of amine in the organic compound.

Another embodiment of the present invention is the light-emitting device with the above structure, in which the organic compound includes at least one of an alkyl group having 3 to 8 carbon atoms and a cycloalkyl group having 6 to 12 carbon atoms in at least one of 2'-, 3'-, 4'-, and 5'-positions in the 1,1'-biphenyl-4-yl group.

Another embodiment of the present invention is the light-emitting device with the above structure, in which the organic compound includes a tert-butyl group in the 3'- and 5'-positions in the 1,1'-biphenyl-4-yl group.

Another embodiment of the present invention is the light-emitting device with the above structure, in which a hydrogen atom is bonded to a carbon atom in a meta-position in one or a plurality of aniline structures included in the arylamine structure in the organic compound.

Another embodiment of the present invention is the light-emitting device with the above structure, in which benzene rings in one or a plurality of aniline structures included in the arylamine structure each independently include a substituent in a para-position in the organic compound.

Another embodiment of the present invention is the light-emitting device with the above structure, in which one of the benzene rings in the plurality of aniline structures included in the arylamine structure includes a cyclohexyl group in a para-position in the organic compound.

Another embodiment of the present invention is the light-emitting device with the above structure, in which one of the benzene rings in the plurality of aniline structures included in the arylamine structure comprises a phenyl group in an ortho-position in the organic compound.

Another embodiment of the present invention is the light-emitting device with the above structure, in which the organic compound includes a triarylamine structure.

Another embodiment of the present invention is the light-emitting device with the above structure, in which a fluorenyl group is bonded to a nitrogen atom of amine of the arylamine structure in the organic compound.

Another embodiment of the present invention is the light-emitting device with the above structure, in which the organic compound is a monoamine compound.

Another embodiment of the present invention is the light-emitting device with the above structure, in which the hole-transport region includes a hole-injection layer and a hole-transport layer, the hole-injection layer is between the anode and the hole-transport layer, and the organic compound is included in the hole-transport layer.

Another embodiment of the present invention is the light-emitting device with the above structure, in which the hole-transport region includes a hole-injection layer and a hole-transport layer, the hole-injection layer is between the anode and the hole-transport layer, and the organic compound is included in both the hole-injection layer and the hole-transport layer.

Another embodiment of the present invention is the light-emitting device with the above structure, in which a substance exhibiting an acceptor property is included in the organic compound of the hole-injection layer.

Another embodiment of the present invention is the light-emitting device with the above structure, in which the substance exhibiting the acceptor property is an organic compound.

One embodiment of the present invention is an organic compound having an arylamine structure. When the organic compound is deposited as a film, the ordinary refractive index of the deposited film with respect to light with a wavelength of 458 nm is greater than or equal to 1.50 and less than or equal to 1.75, and the birefringence Δn of the deposited film with respect to light with a wavelength of 458 nm is greater than or equal to 0 and less than or equal to 0.008.

Another embodiment of the present invention is an organic compound having an arylamine structure. When the organic compound is deposited as a film, the ordinary refractive index of the deposited film with respect to light with a wavelength of 458 nm is greater than or equal to 1.50 and less than or equal to 1.75, and the alignment order parameter of the deposited film with respect to light with a wavelength corresponding to the longest wavelength where an absorption peak appears in an absorption spectrum is greater than or equal to −0.07 and less than or equal to 0.00.

Another embodiment of the present invention is the organic compound with the above structure, in which a group including at least one para-biphenyl structure is bonded to a nitrogen atom of amine of the arylamine structure.

Another embodiment of the present invention is an organic compound including an arylamine structure. When the organic compound is deposited as a film, the ordinary refractive index of the deposited film with respect to light with a wavelength of 458 nm is greater than or equal to 1.50 and less than or equal to 1.75, and the birefringence Δn of the deposited film with respect to light with a wavelength of 458 nm is greater than or equal to 0 and less than or equal to 0.04. A 1-1'-biphenyl-4-yl group is bonded to a nitrogen atom of amine in the organic compound.

Another embodiment of the present invention is an organic compound having an arylamine structure. When the organic compound is deposited as a film, the ordinary refractive index of the deposited film with respect to light with a wavelength of 458 nm is greater than or equal to 1.50 and less than or equal to 1.75, and the alignment order parameter of the deposited film with respect to light with a wavelength corresponding to the longest wavelength where an absorption peak appears in the absorption spectrum is greater than or equal to −0.10 and less than or equal to 0.00. A 1-1'-biphenyl-4-yl group is bonded to a nitrogen atom of amine in the organic compound.

Another embodiment of the present invention is the organic compound with the above structure, which includes at least one of an alkyl group having 3 to 8 carbon atoms and a cycloalkyl group having 6 to 12 carbon atoms in at least one of 2'-, 3'-, 4'-, and 5'-positions of the 1-1'-biphenyl-4-yl group.

Another embodiment of the present invention is the organic compound with the above structure, which includes a tert-butyl group in the 3'- and 5'-positions of the 1-1'-biphenyl-4-yl group.

Another embodiment of the present invention is the organic compound with the above structure, in which hydrogen is bonded to carbon positioned in a meta-position in a benzene ring in one or a plurality of aniline structures included in the arylamine structure.

Another embodiment of the present invention is the organic compound with the above structure, in which benzene rings in the one or plurality of aniline structures included in the arylamine structure each independently include a substituent in a para-position.

Another embodiment of the present invention is the organic compound with the above structure, in which one of the benzene rings in the plurality of aniline structures included in the arylamine structure includes a cyclohexyl group in a para-position.

Another embodiment of the present invention is the organic compound with the above structure, in which one of the benzene rings in the plurality of aniline structures included in the arylamine structure comprises a phenyl group in an ortho-position.

Another embodiment of the present invention is the organic compound with the above structure, which includes a triarylamine structure.

Another embodiment of the present invention is the organic compound with the above structure, in which a fluorenyl group is bonded to the nitrogen atom.

Another embodiment of the present invention is the organic compound with the above structure, which is a monoamine compound.

Another embodiment of the present invention is a material for a hole-transport layer, which includes any of the organic compounds described above.

Another embodiment of the present invention is a material for a hole-injection layer, which includes any of the organic compounds described above.

Another embodiment of the present invention is a light-emitting device including any of the organic compounds described above.

Another embodiment of the present invention is an electronic apparatus including any of the above light-emitting devices, and at least one of a sensor, an operation button, a speaker, and a microphone.

Another embodiment of the present invention is a light-emitting apparatus including any of the above light-emitting devices, and at least one of a transistor and a substrate.

Another embodiment of the present invention is a lighting device including any of the above light-emitting devices and a housing.

Note that the light-emitting apparatus in this specification includes, in its category, an image display device that uses a light-emitting device. The light-emitting apparatus may also include a module in which a light-emitting device is provided with a connector such as an anisotropic conductive film or a tape carrier package (TCP), a module in which a printed wiring board is provided at the end of a TCP, and a module in which an integrated circuit (IC) is directly mounted on a light-emitting device by a chip on glass (COG) method. Furthermore, a lighting device or the like may include the light-emitting apparatus.

According to one embodiment of the present invention, an organic compound with which a light-emitting device with high emission efficiency and low driving voltage can be manufactured can be provided. According to another embodiment of the present invention, a light-emitting device with high emission efficiency and low driving voltage can be provided. According to another embodiment of the present invention, any of a light-emitting device, a light-emitting apparatus, an electronic apparatus, a display device, and an electronic device each having low power consumption can be provided.

Note that the description of these effects does not preclude the existence of other effects. One embodiment of the present invention does not necessarily have all the effects listed above. Other effects will be apparent from and can be derived from the description of the specification, the drawings, the claims, and the like.

BRIEF DESCRIPTION OF THE DRAWINGS

In the accompanying drawings:

FIGS. 9A, 9B1, 9B2, and 9C illustrate electronic apparatuses;

DETAILED DESCRIPTION OF THE INVENTION

Embodiments and examples of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments and examples.

Embodiment 1

Of light entering a material perpendicularly to the light axis of the material, light with a plane of vibration perpendicular to the light axis is called ordinary light (an ordinary ray) and light with a plane of vibration parallel to the light axis is called extraordinary light (an extraordinary ray). An ordinary refractive index $n_o$ and an extraordinary refractive index $n_e$ are refractive indices of a material to be measured with respect to ordinary light and extraordinary light. The ordinary refractive index $n_o$ and the extraordinary refractive index $n_e$ can be calculated by anisotropic analysis. Birefringence (Δn) is expressed by the difference between the ordinary refractive index $n_o$ and the extraordinary refractive index $n_e$ ($\Delta n = |n_o - n_e|$). When a material has anisotropy, the refractive index $n_o$ for ordinary light and the refractive index $n_e$ for extraordinary light sometimes differ from each other, and the difference is the birefringence Δn.

An organic compound of one embodiment of the present invention has an arylamine structure. When the organic compound is deposited as a film, an ordinary refractive index of the deposited film with respect to light with a wavelength of 458 nm is greater than or equal to 1.50 and less than or equal to 1.75, and birefringence Δn of the deposited film with respect to light with a wavelength of 458 nm is greater than or equal to 0 and less than or equal to 0.008.

Figure 1:
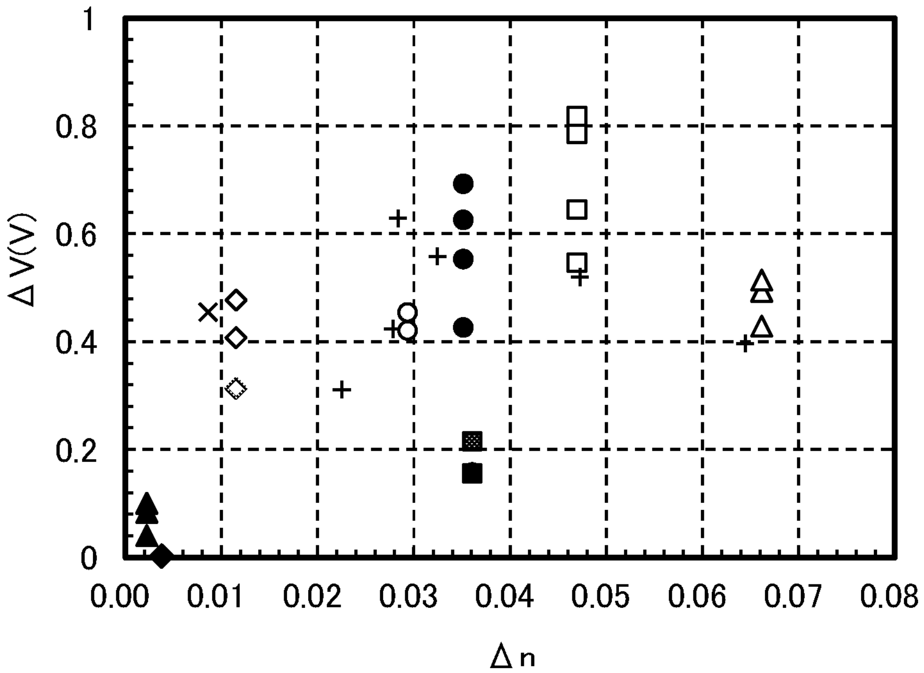
FIG. 1 is a graph showing a difference in driving voltage (ΔV) between a conventional light-emitting device and a light-emitting device including an organic compound with a low refractive index, versus birefringence Δn of a deposited film of the organic compound.

FIG. 1 is a graph showing the relationship between the driving voltage of a light-emitting device and the birefringence Δn of an organic compound used in a hole-transport region (a hole-injection layer and a hole-transport layer).

In FIG. 1, the vertical axis represents a difference in driving voltage (ΔV, at a current of 1 mA) between a reference light-emitting device and light-emitting devices in each of which an organic compound with a low refractive index is used in the hole-transport region. A material that is generally used in light-emitting devices and has a refractive index of approximately 1.8 to 1.9 is used in the hole-transport region of the reference light-emitting device. Note that the light-emitting devices have approximately the same element structure except for the organic compound. In FIG. 1, the horizontal axis represents birefringence Δn of the organic compounds used in the hole-transport region of the light-emitting devices. Note that in FIG. 1, the same symbols are used for plotted points of light-emitting devices including the same organic compound except for plotted points "+".

The light-emitting device that includes an organic compound with a low refractive index sometimes has higher driving voltage than a light-emitting device that includes an organic compound exhibiting a normal refractive index because of having a group with a low molecular refraction or the like, as described above. Actually, in FIG. 1, most of the light-emitting devices have higher driving voltage than the reference light-emitting device not including a low-refractive-index material by 0.3 V or more.

However, as shown in FIG. 1, the organic EL device that has a material with extremely low birefringence Δn less than or equal to 0.008 with respect to light with a wavelength of 458 nm exhibits significantly low driving voltage as compared to the organic EL device including a material with high birefringence Δn. The results show that a light-emitting device that has low driving voltage and high external quantum efficiency and includes a layer with a low refractive index in the EL layer can be manufactured with the use of the following organic compound: the organic compound, when being deposited to be a film, has a low refractive index and low birefringence Δn, i.e., the ordinary refractive index of the deposited film with respect to light with a wavelength of 458 nm is greater than or equal to 1.50 and less than or equal to 1.75 and the birefringence Δn of the deposited film with respect to light with a wavelength of 458 nm is greater than or equal to 0 and less than or equal to 0.008.

Figure 2:
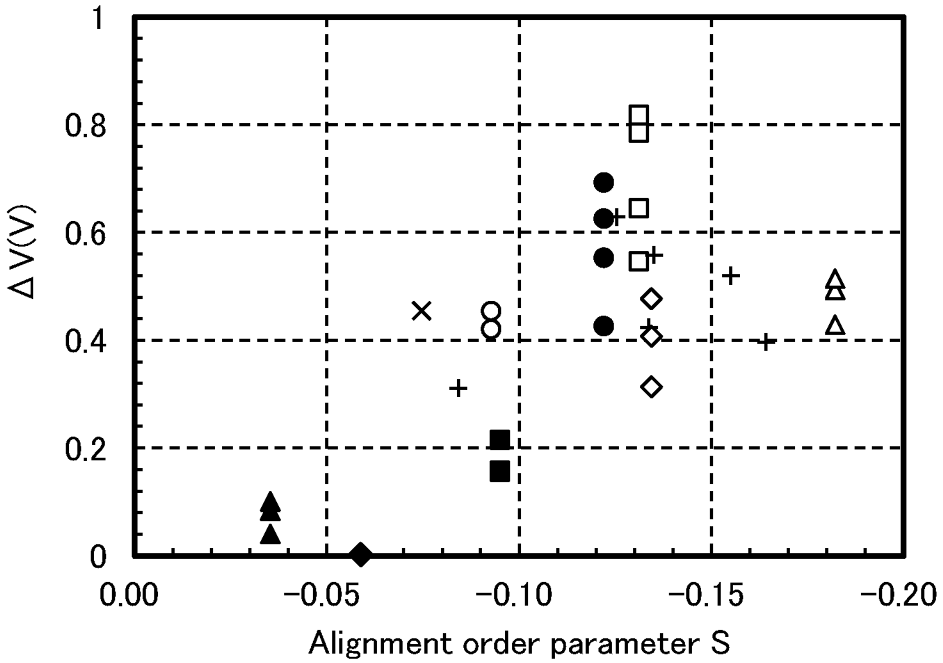
FIG. 2 is a graph showing a difference in driving voltage (ΔV) between a conventional light-emitting device and a light-emitting device including an organic compound with a low refractive index, versus an alignment order parameter S of a deposited film of the organic compound.

Low birefringence Δn means that there is little difference between an optical effect of the material on ordinary light and that on extraordinary light. FIG. 2 is a graph showing the relationship between the alignment order parameter S of an organic compound with a low refractive index, which is used in a light-emitting device having a similar device structure, and a difference in driving voltage (ΔV, at a current of 1 mA) between the light-emitting device and a light-emitting device including a conventional material. The alignment order parameter S is expressed by $S=(k_e-k_o)/(k_e+2k_o)$, where $k_o$ represents an extinction coefficient with respect to light perpendicular to the light axis and $k_e$ represents an extinction coefficient with respect to light parallel to the light axis. The alignment order parameter S is used as an index indicating the alignment state of a material. The alignment order parameter S falls within a range from −0.5 to +1; it is −0.5 in the case of completely parallel alignment with respect to the substrate, +1 in the case of completely perpendicular alignment with respect to the substrate, and 0 in the case of random alignment.

In FIG. 1 and FIG. 2, the same symbols are used for the results of the light-emitting devices including the same organic compound. According to FIG. 2, the material with low birefringence Δn tends to have low alignment order parameter S, which shows a correlation with ΔV. Specifically, a light-emitting device that has low driving voltage and high external quantum efficiency and includes a layer with a low refractive index in the EL layer can be manufactured with the use of the following organic compound: when the organic compound is deposited as a film, the deposited film has a low refractive index (the ordinary refractive index of the deposited film with respect to light with a wavelength of 458 nm is greater than or equal to 1.50 and less than or equal to 1.75) and exhibits an alignment order parameter S greater than or equal to −0.07 and less than or equal to 0.00 with respect to light with a wavelength corresponding to the longest wavelength where an absorption peak appears in the absorption spectrum. This value approximates 0, showing that the use of a material with alignment close to random alignment makes it possible to lower the driving voltage of the light-emitting device.

The organic compound that is used in the light-emitting device and has an ordinary refractive index is greater than or equal to 1.50 and less than or equal to 1.75 with respect to light with a wavelength of 458 nm when being deposited as a film preferably has an amine structure in order to obtain a favorable carrier-transport property. It is further preferable that the amine structure be an arylamine structure to enhance the carrier-transport property. It is still further preferable that the arylamine structure be a triarylamine structure for the same reason.

It is preferable that one or more groups each having a biphenyl structure be bonded to nitrogen in the amine structure. An organic compound in which a group including an ortho-biphenyl structure is bonded as the group including the biphenyl structure is preferable in order to obtain a favorable carrier-transport property. Alternatively, an organic compound in which a group including a fluorene structure is bonded as the group including the biphenyl structure is preferable to obtain a favorable carrier-transport property. Alternatively, an organic compound in which a group including a para-biphenyl structure is bonded as the group including the biphenyl structure is preferable to obtain a favorable carrier-transport property and improve the glass transition temperature (Tg).

It is preferable that a 1,1'-biphenyl-4-yl group be bonded to nitrogen in the amine structure in the organic compound, and that when the organic compound is deposited as a film, the birefringence Δn of the deposited film with respect to light with a wavelength of 458 nm be greater than or equal to 0.008 and less than or equal to 0.04, or the alignment order parameter S of the deposited film with respect to light with a wavelength corresponding the longest wavelength where an absorption peak appears in the absorption spectrum be greater than or equal to −0.10 and less than or equal to 0.00. With this structure, a light-emitting device with low driving voltage can be obtained.

That is, either of the following organic compounds is preferable: an organic compound that includes an arylamine structure and a 1,1'-bephenyl-4-yl group and whose ordinary refractive index with respect to light with a wavelength of 458 nm is greater than or equal to 1.50 and less than or equal to 1.75 when the organic compound is a deposited film and whose birefringence Δn with respect to light with a wavelength of 458 nm is greater than or equal to 0 and less than or equal to 0.04 when the organic compound is a deposited film; and an organic compound that includes an arylamine structure and a 1,1'-bephenyl-4-yl group and whose ordinary refractive index with respect to light with a wavelength of 458 nm is greater than or equal to 1.50 and less than or equal to 1.75 when the organic compound is a deposited film and whose alignment order parameter S with respect to light with a wavelength corresponding to the longest wavelength where an absorption peak appears in the absorption spectrum is greater than or equal to −0.10 and less than or equal to 0.00 when the organic compound is a deposited film. A light-emitting device using such an organic compound can have high external efficiency, low driving voltage, and low power consumption.

In addition, to achieve a low refractive index, it is preferable that a plurality of saturated hydrocarbon groups and/or a plurality of cyclic hydrocarbon groups be bonded in the organic compound. The saturated hydrocarbon group and the cyclic saturated hydrocarbon group are preferably groups each having 1 to 12 carbon atoms, further preferably an alkyl group having 3 to 8 carbon atoms and a cycloalkyl group having 6 to 12 carbon atoms, still further preferably a tert-butyl group and a cyclohexyl group. Note that these groups inhibit transportation of carriers when bonded to a meta-position of a benzene ring directly bonded to nitrogen of an amine skeleton; therefore, it is preferable that these groups not be bonded to such a position. In other words, it is preferable that neither the saturated hydrocarbon group nor the cyclic saturated hydrocarbon group be bonded to a meta-position of an aniline structure.

In addition, an alkyl group having 3 to 8 carbon atoms and a cycloalkyl group having 6 to 12 carbon atoms are preferably bonded to at least one of 2'-, 3'-, 4'-, and 5'-positions of the 1,1'-bephenyl-4-yl group, and in particular, a tert-butyl group is preferably bonded to the 3'- and 5'-positions.

All of the carbon atoms contained in the saturated hydrocarbon group and the cyclic saturated hydrocarbon group form bonds by $sp^3$ hybrid orbitals. The percentage of carbon atoms each forming a bond by the $sp^3$ hybrid orbitals in the total number of carbon atoms in a molecule is preferably greater than or equal to 23% and less than or equal to 55%.

Alternatively, when the above organic compound is subjected to $^1$H-NMR measurement, the integral value of signals at lower than 4 ppm preferably exceeds the integral value of signals at 4 ppm or higher.

It is preferable that the organic compound include at least one fluorene structure to obtain a favorable carrier-transport property.

Examples of the above-described organic compound having a hole-transport property include organic compounds having structures represented by General formulae ($G_{h1}1$) to ($G_{h1}4$) and ($G_{h2}1$) to ($G_{h2}3$) shown below. The organic compounds having such structures have an ordinary refractive index greater than or equal to 1.50 and less than or equal to 1.75 with respect to light with a wavelength of 458 nm when the organic compounds are deposited films. Of these organic compounds, an organic compound whose birefringence Δn with respect to light with a wavelength of 458 nm or alignment order parameter S with respect to light with a wavelength corresponding to the longest wavelength where an absorption peak appears in the absorption spectrum is within the above range can be selected to be used.

[Chemical formula 1]

($G_{h1}1$)

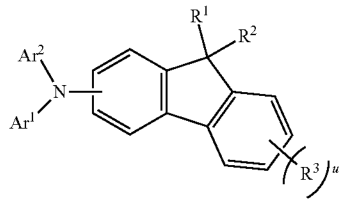

In General formula ($G_{h1}1$), $Ar^1$ and $Ar^2$ each independently represent a substituent with a benzene ring or a substituent in which two or three benzene rings are bonded to each other. Note that one or both of $Ar^1$ and $Ar^2$ have one or more hydrocarbon groups each having 1 to 12 carbon atoms each forming a bond only by the $sp^3$ hybrid orbitals. The total number of carbon atoms contained in all of the hydrocarbon groups bonded to $Ar^1$ and $Ar^2$ is 8 or more and the total number of carbon atoms contained in all of the hydrocarbon groups bonded to $Ar^1$ or $Ar^2$ is 6 or more. Note that in the case where a plurality of straight-chain alkyl groups each having one or two carbon atoms are bonded to $Ar^1$ or $Ar^2$ as the hydrocarbon groups, the straight-chain alkyl groups may be bonded to each other to form a ring.

[Chemical formula 2]

($G_{h1}2$)

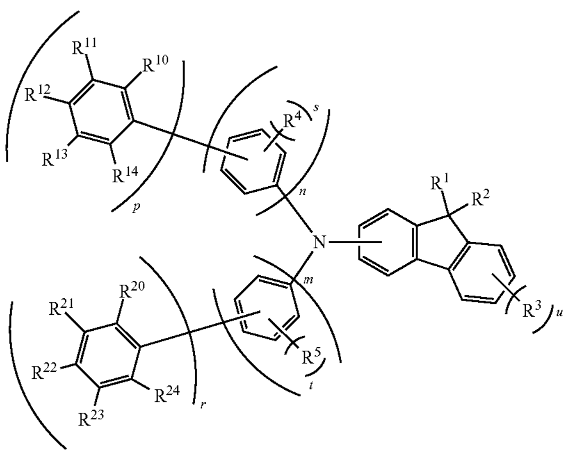

In General formula ($G_{h1}2$), m and r each independently represent 1 or 2 and m+r is 2 or 3. Furthermore, t represents an integer of 0 to 4 and is preferably 0. $R^5$ represents any of hydrocarbon groups having 1 to 3 carbon atoms, and in the case where t is an integer of 2 to 4, $R^5$s may be the same as or different from each other; in the case where there are $R^5$s, adjacent groups (adjacent $R^5$s) may be bonded to each other to form a ring. When m is 2, the kind and number of substituents and the position of bonds included in one phenylene group may be the same as or different from those of the other phenylene group; when r is 2, the kind and number of substituents and the position of bonds included in one phenyl group may be the same as or different from those of the other phenyl group.

[Chemical formula 3]

($G_{h1}3$)

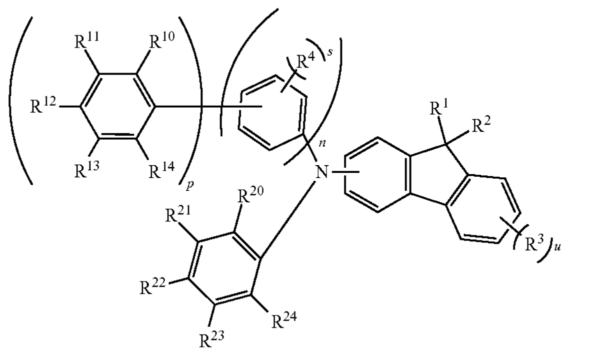

In General formulae ($G_{h1}2$) and ($G_{h1}3$), n and p each independently represent 1 or 2 and n+p is 2 or 3. In addition, s represents an integer of 0 to 4 and is preferably 0. $R^4$ represents any of hydrocarbon groups having 1 to 3 carbon atoms, and in the case where s is an integer of 2 to 4, $R^4$s may be the same as or different from each other; in the case where there are $R^4$s, adjacent groups (adjacent $R^4$s) may be bonded to each other to form a ring. When n is 2, the kind and number of substituents and the position of bonds in one phenylene group may be the same as or different from those of the other phenylene group; when p is 2, the kind and number of substituents and the position of bonds in one phenyl group may be the same as or different from those of the other phenyl group.

[Chemical formula 4]

($G_{h1}4$)

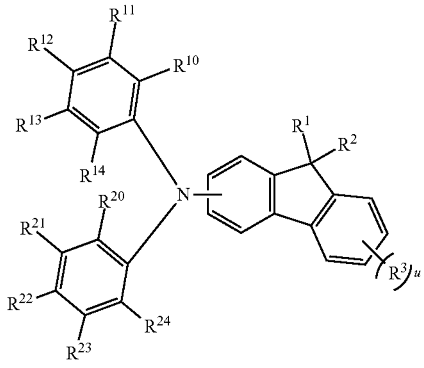

In General formulae ($G_{h1}2$) to ($G_{h1}4$), $R^{10}$ to $R^{14}$ and $R^{20}$ to $R^{24}$ each independently represent hydrogen or a hydrocarbon group having 1 to 12 carbon atoms each forming a bond only by the $sp^3$ hybrid orbitals. Note that at least three of $R^{10}$ to $R^{14}$ and at least three of $R^{20}$ to $R^{24}$ are preferably hydrogen. As the hydrocarbon group having 1 to 12 carbon atoms each forming a bonded only by the $sp^3$ hybrid orbitals, a tert-butyl group and a cyclohexyl group are preferable. The total number of carbon atoms contained in $R^{10}$ to $R^{14}$ and $R^{20}$ to $R^{24}$ is 8 or more and the total number of carbon atoms contained in either $R^{10}$ to $R^{14}$ or $R^{20}$ to $R^{24}$ is 6 or more. Note that adjacent groups of $R^{10}$ to $R^{14}$ and $R^{20}$ to $R^{24}$ may be bonded to each other to form a ring.

In General formulae ($G_{h1}1$) to ($G_{h1}4$), each u independently represents an integer of 0 to 4 and is preferably 0.

Note that in the case where u is an integer of 2 to 4, $R^3$s may be the same as or different from each other. In addition, $R^1$, $R^2$, and $R^3$ each independently represent an alkyl group having 1 to 4 carbon atoms and $R^1$ and $R^2$ may be bonded to each other to form a ring.

An arylamine compound that has at least one aromatic group having first to third benzene ring and at least three alkyl groups, as in General formulae ($G_{h2}1$) to ($G_{h2}3$) shown below, is preferable as one of the materials having a hole-transport property. Note that the first to third benzene rings are bonded in this order and the first benzene ring is directly bonded to nitrogen of amine.

The first benzene ring may further include a substituted or unsubstituted phenyl group and preferably includes an unsubstituted phenyl group. Furthermore, the second benzene ring or the third benzene ring may include a phenyl group substituted by an alkyl group.

Note that hydrogen is not directly bonded to carbon atoms at 1- and 3-positions in two or more of, preferably all of the first to third benzene rings, and the carbon atoms are bonded to any of the first to third benzene rings, the phenyl group substituted by the alkyl group, the at least three alkyl groups, and the nitrogen of the amine.

It is preferable that the arylamine compound further include a second aromatic group. It is preferable that the second aromatic group have an unsubstituted monocyclic ring or a substituted or unsubstituted bicyclic or tricyclic condensed ring; in particular, it is further preferable that the second aromatic group be a group having a substituted or unsubstituted bicyclic, or tricyclic condensed ring where the number of carbon atoms forming the ring is 6 to 13. It is still further preferably that the second aromatic group be a group including a fluorene ring. Note that a dimethylfluorenyl group is preferable as the second aromatic group.

It is preferable that the arylamine compound further include a third aromatic group. The third aromatic group is a group having 1 to 3 substituted or unsubstituted benzene rings.

It is preferable that the at least three alkyl groups and the alkyl group substituted for the phenyl group be each a chain alkyl group having 2 to 5 carbon atoms. In particular, as the alkyl group, a chain alkyl group having a branch of 3 to 5 carbon atoms is preferable, and a t-butyl group is further preferable.

[Chemical formulae 5]

($G_{h2}1$)

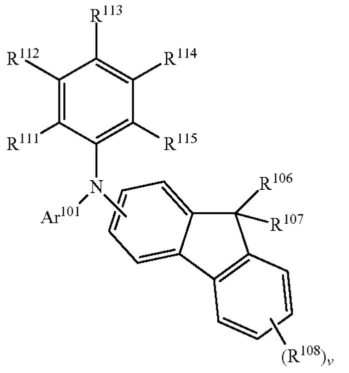

-continued (g1)

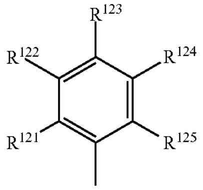

(g2)

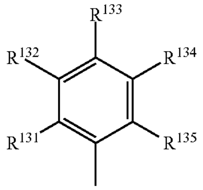

Note that in General formula ($G_{h2}1$), $Ar^{101}$ represents a substituted or unsubstituted benzene ring or a substituent in which two or three substituted or unsubstituted benzene rings are bonded to one another.

[Chemical formulae 6]

($G_{h2}2$)

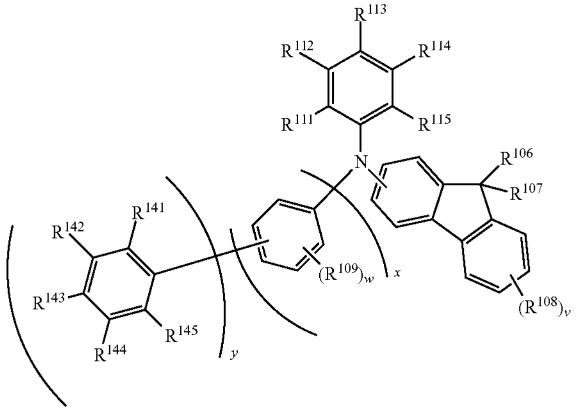

(g1)

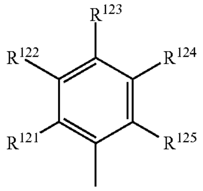

(g2)

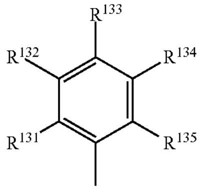

Note that in General formula ($G_{h2}2$), x and y each independently represent 1 or 2 and x+y is 2 or 3. Furthermore, $R^{109}$ represents an alkyl group having 1 to 4 carbon atoms, and w represents an integer of 0 to 4. $R^{141}$ to $R^{145}$ each independently represent any one of hydrogen, an alkyl group having 1 to 6 carbon atoms, and a cycloalkyl group having 5 to 12 carbon atoms. When w is an integer of 2 or more, $R^{109}$s may be the same as or different from each other. When x is 2, the kind and number of substituents and the position of bonds included in one phenylene group may be the same as or different from those of the other phenylene group. When y is 2, the kind and number of substituents and the position of bonds included in one phenyl group including $R^{141}$ to $R^{145}$ may be the same as or different from those of the other phenyl group including $R^{141}$ to $R^{145}$.

[Chemical formulae 7]

($G_{h2}3$)

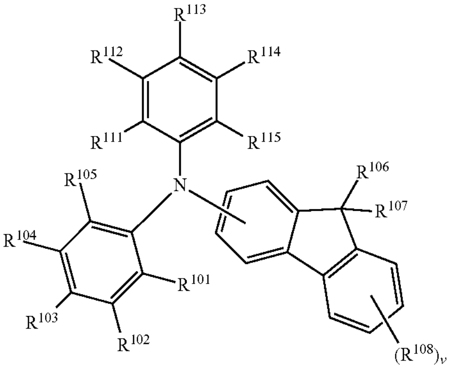

(g1)

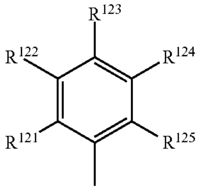

(g2)

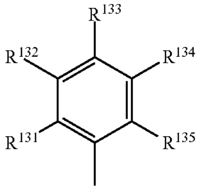

In General formula ($G_{h2}3$), $R^{101}$ to $R^{105}$ each independently represent any one of hydrogen, an alkyl group having 1 to 6 carbon atoms, a cycloalkyl group having 6 to 12 carbon atoms, and a substituted or unsubstituted phenyl group.

In General formulae ($G_{h2}1$) to ($G_{h2}3$), $R^{106}$, $R^{107}$, and $R^{108}$ each independently represent an alkyl group having 1 to 4 carbon atoms, and v represents an integer of 0 to 4. Note that when v is 2 or more, $R^{108}$s may be the same as or different from each other. One of $R^{111}$ to $R^{115}$ represents a substituent represented by General formula (g1), and the others each independently represent any one of hydrogen, an alkyl group having 1 to 6 carbon atoms, and a substituted or unsubstituted phenyl group. In General formula (g1), one of $R^{121}$ to $R^{125}$ represents a substituent represented by General formula (g2), and the others each independently represent any one of hydrogen, an alkyl group having 1 to 6 carbon atoms, and a phenyl group substituted by an alkyl group having 1 to 6 carbon atoms. In General formula (g2), $R^{131}$ to $R^{135}$ each independently represent any one of hydrogen, an alkyl group having 1 to 6 carbon atoms, and a phenyl group substituted by an alkyl group having 1 to 6 carbon atoms. Note that at least three of $R^{111}$ to $R^{115}$, $R^{121}$ to $R^{125}$, and $R^{131}$ to $R^{135}$ are each an alkyl group having 1 to 6 carbon atoms; the number of substituted or unsubstituted phenyl groups in $R^{111}$ to $R^{115}$ is one or less; and the number of phenyl groups substituted by an alkyl group having 1 to 6 carbon atoms in $R^{121}$ to $R^{125}$ and $R^{131}$ to $R^{135}$ is one or less. In at least two combinations of the three combinations $R^{112}$ and $R^{114}$, $R^{122}$ and $R^{124}$, and $R^{132}$ and $R^{134}$, at least one R represents any of the substituents other than hydrogen.

Note that as for the expression "substituted or unsubstituted" in this specification, when a substituted or unsubstituted group has a substituent, an alkyl group having 1 to 6 carbon atoms or a cycloalkyl group having 5 to 12 carbon atoms can be used as the substituent.

As described above, the organic compound of one embodiment of the present invention has a low refractive index, and an increase in the driving voltage of the light-emitting device is small when the organic compound is used in the light-emitting device. Thus, the light-emitting device including the organic compound of one embodiment of the present invention can have high external quantum efficiency and low driving voltage.

Embodiment 2

Figure 3A:
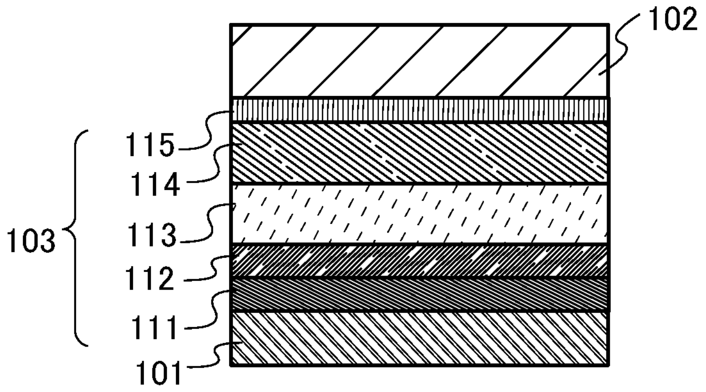
FIGS. 3A to 3C are schematic views of light-emitting devices.

FIG. 3A illustrates a light-emitting device of one embodiment of the present invention. The light-emitting device of one embodiment of the present invention includes a first electrode 101, a second electrode 102, and an EL layer 103, and the organic compound described in Embodiment 1 is used for the EL layer.

The EL layer 103 includes a light-emitting layer 113 and may also include one or both of a hole-injection layer 111 and a hole-transport layer 112. The light-emitting layer 113 includes a light-emitting material, and light is emitted from the light-emitting material in the light-emitting device of one embodiment of the present invention. The light-emitting layer 113 may include a host material and other materials. The organic compound of one embodiment of the present invention described in Embodiment 1 may be included in any of the light-emitting layer 113, the hole-transport layer 112, and the hole-injection layer; alternatively, the organic compound may be included in all of them.

Note that FIG. 3A additionally illustrates an electron-transport layer 114 and an electron-injection layer 115; however, the structure of the light-emitting device is not limited thereto.

The organic compound exhibits a good hole-transport property and thus is effectively used for the hole-transport layer 112. Furthermore, a mixed film of the organic compound of one embodiment of the present invention and an acceptor substance can be used as the hole-injection layer 111.

In addition, the organic compound of one embodiment of the present invention can be used as a host material. Furthermore, the hole-transport material and an electron-transport material may be deposited by co-evaporation so that an exciplex is formed of the electron-transport material and the hole-transport material in the light-emitting layer. The exciplex having an appropriate emission wavelength allows efficient energy transfer to the light-emitting material, achieving a light-emitting device with a high efficiency and a long lifetime.

Since the organic compound of one embodiment of the present invention has a low refractive index, the light-emitting device including the organic compound in its EL layer can have high external quantum efficiency. In addition, using the organic compound of one embodiment of the present invention in the light-emitting device can inhibit an increase in the driving voltage as compared to the case of using another low-refractive index organic compound in the light-emitting device. Thus, the light-emitting device including the organic compound of one embodiment of the present invention can have high external quantum efficiency and low driving voltage.

Next, examples of specific structures and materials of the above-described light-emitting device will be described. As described above, the light-emitting device of one embodiment of the present invention includes, between the pair of electrodes of the first electrode 101 and the second electrode 102, the EL layer 103 including a plurality of layers; the EL layer 103 includes the organic compound disclosed in Embodiment 1 in any of the layers.

The first electrode 101 is preferably formed using any of metals, alloys, and conductive compounds with a high work function (specifically, higher than or equal to 4.0 eV), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer that is in contact with the first electrode 101 in the EL layer 103, an electrode material can be selected regardless of its work function.

Although the EL layer 103 preferably has a stacked-layer structure, there is no particular limitation on the stacked-layer structure, and various layers such as a hole-injection layer, a hole-transport layer, an electron-transport layer, an electron-injection layer, a carrier-blocking layer, an exciton-blocking layer, and a charge-generation layer can be employed. Two kinds of stacked-layer structure of the EL layer 103 are described: the structure illustrated in FIG. 3A, which includes the electron-transport layer 114 and the electron-injection layer 115 in addition to the hole-injection layer 111, the hole-transport layer 112, and the light-emitting layer 113; and the structure illustrated in FIG. 3B, which includes the electron-transport layer 114, the electron-injection layer 115, and a charge-generation layer 116 in addition to the hole-injection layer 111, the hole-transport layer 112, and the light-emitting layer 113. Materials for forming each layer will be specifically described below.

The hole-injection layer 111 contains a substance having an acceptor property. Either an organic compound or an inorganic compound can be used as the substance having an acceptor property.

As the substance having an acceptor property, it is possible to use a compound having an electron-withdrawing group (e.g., a halogen group or a cyano group); for example, 7,7,8,8-tetracyano-2,3,5,6-tetrafluoroquinodimethane (abbreviation: $F_4$-TCNQ), chloranil, 2,3,6,7,10,11-hexacyano- 1,4,5,8,9,12-hexaazatriphenylene (abbreviation: HAT-CN), 1,3,4,5,7,8-hexafluorotetracyano-naphthoquinodimethane (abbreviation: F6-TCNNQ), or 2-(7-dicyanomethylene-1,3,4,5,6,8,9,10-octafluoro-7H-pyren-2-ylidene)malononitrile can be used. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a cyano group, a halogen group such as a fluoro group, or the like) has a very high electron-accepting property and thus is preferable. Specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS). The substance having an acceptor property can extract electrons from an adjacent hole-transport layer (or hole-transport material) by the application of an electric field.

Alternatively, a composite material in which a material having a hole-transport property contains any of the aforementioned substances having an acceptor property can be used for the hole-injection layer 111. By using a composite material in which a material having a hole-transport property contains an acceptor substance, a material used to form an electrode can be selected regardless of its work function. In other words, besides a material having a high work function, a material having a low work function can be used for the first electrode 101.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the material having a hole-transport property used for the composite material preferably has a hole mobility of $1\times10^{-6}$ $cm^2/Vs$ or higher. Organic compounds which can be used as the material having a hole-transport property in the composite material are specifically given below.

Examples of the aromatic amine compounds that can be used for the composite material include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenylanthracen-9-yl)phenyl]-9H-carbazole (abbreviation: CzPA), and 1,4-bis[4-(N-carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA). Note that the organic compound of one embodiment of the present invention can also be used.

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide](abbreviation: PTPDMA), and poly[N,N'-bis(4-butylphenyl)-N,N'-bis(phenyl)benzidine](abbreviation: poly-TPD).

The material having a hole-transport property that is used in the composite material further preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used. Note that the hole-transport material having an N,N-bis(4-biphenyl)amino group is preferable because a light-emitting device having a long lifetime can be fabricated. Specific examples of the hole-transport material include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II) (4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;

1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6;2-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-[4'-(carbazole-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis([1,1'-biphenyl]-4-yl)-9,9'-spirobi[9H-fluoren]-2-amine (abbreviation: BBASF), N,N-bis([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]-9,9'-spirobi[9H-fluoren]-2-amine (abbreviation: PCBASF), N-(1,1'-biphenyl-4-yl)-9,9-dimethyl-N-[4-(9-phenyl-9H-carbazol-3-yl)phenyl]-9H-fluoren-2-amine (abbreviation: PCBBiF), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)-9,9'-spirobi-9H-fluoren-2-amine, and N,N-bis(9,9-dimethyl-9H-fluoren-2-yl)-9,9'-spirobi-9H-fluoren-1-amine.

Note that it is further preferable that the material having a hole-transport property to be used in the composite material have a relatively deep HOMO level of greater than or equal to −5.7 eV and lower than or equal to −5.4 eV. Using the material with a hole-transport property which has a relatively deep HOMO level in the composite material makes it easy to inject holes into the hole-transport layer 112 and to obtain a light-emitting device having a long lifetime.

Note that the organic compound described in Embodiment 1 also has a hole-transport property, and thus can be suitably used as the material for a hole-injection layer used in the composite material. A layer with a low refractive index can be formed in the EL layer 103 with the use of the organic compound described in Embodiment 1, leading to higher external quantum efficiency of the light-emitting device.

Note that mixing the above composite material with a fluoride of an alkali metal or an alkaline earth metal (the proportion of fluorine atoms in a layer using the mixed material is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, which allows the light-emitting device to be driven at a low voltage. In addition, the organic compound having an acceptor property is easy to use because it is easily deposited by vapor deposition.

The hole-transport layer 112 is formed using a material having a hole-transport property. The material having a hole-transport property preferably has a hole mobility higher than or equal to $1\times10^{-6}$ $cm^2/Vs$. The organic compound described in Embodiment 1 has a hole-transport property, and thus can be suitably used as a material for a hole-transport layer. Thus, the hole-transport layer 112 preferably includes the organic compound described in Embodiment 1, further preferably is formed using only the organic compound described in Embodiment 1. The hole-transport layer 112 including the organic compound described in Embodiment 1 can be a layer with a low refractive index in the EL layer 103, leading to higher external quantum efficiency of the light-emitting device.

Examples of the material having a hole-transport property, in the case of using a material other than the organic compound described in Embodiment 1 for the hole-transport layer 112, include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]-9,9'-spirobi[9H-fluoren]-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi- II). Among the above materials, the compound having an aromatic amine skeleton and the compound having a carbazole skeleton are preferable because these compounds are highly reliable and have high hole-transport properties to contribute to a reduction in drive voltage. Note that any of the substances given as examples of the material having a hole-transport property used for the composite material for the hole-injection layer 111 can also be suitably used as the material included in the hole-transport layer 112.

The light-emitting layer 113 includes a light-emitting substance and a host material. The light-emitting layer 113 may additionally include other materials. Alternatively, the light-emitting layer 113 may be a stack of two layers with different compositions.

As the light-emitting substance, fluorescent substances, phosphorescent substances, substances exhibiting thermally activated delayed fluorescence (TADF), or other light-emitting substances may be used. Note that one embodiment of the present invention is more suitably used in the case where the light-emitting layer 113 emits fluorescence, specifically, blue fluorescence.

Examples of the material that can be used as a fluorescent substance in the light-emitting layer 113 are as follows. Other fluorescent substances can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N'-diphenyl-N,N'-(1,6-pyrene-diyl)bis[(6-phenylbenzo[b]naphtho[1,2-d]furan)-8-amine](abbreviation: 1,6BnfAPrn-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). Condensed aromatic diamine compounds typified by pyrenediamine compounds such as 1,6FLPAPrn, 1,6mMemFLPAPrn, and 1,6BnfAPrn-03 are particularly preferable because of their high hole-trapping properties, high emission efficiency, and high reliability. Furthermore, an organic compound having a naphthobisbenzofuran skeleton or a naphthobisbenzothiophene skeleton is preferable because it exhibits deep blue fluorescence and enables a favorable blue light-emitting device to be provided.

Examples of the material that can be used when a phosphorescent substance is used as the light-emitting substance in the light-emitting layer 113 are as follows.

The examples are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: $[Ir(mpptz\text{-}dmp)_3]$), tris(5-methyl-3,4-diphenyl-4H-1,2,4-triazolato)iridium(III) (abbreviation: $[Ir(Mptz)_3]$), and tris[4-(3-biphenyl)-5-isopropyl-3-phenyl-4H-1,2,4-triazolato]iridium(III) (abbreviation: $[Ir(iPrptz\text{-}3b)_3]$); an organometallic iridium complex having a 1H-triazole skeleton, such as tris[3-methyl-1-(2-methylphenyl)-5-phenyl-TH-1,2,4-triazolato]iridium(III) (abbreviation: $[Ir(Mptz1\text{-}mp)_3]$) and tris(1-methyl-5-phenyl-3-propyl-TH-1,2,4-triazolato)iridium(III) (abbreviation: $[Ir(Prptz1\text{-}Me)_3]$); an organometallic iridium complex having an imidazole skeleton, such as fac-tris[1-(2,6-diisopropylphenyl)-2-phenyl-1H-imidazole]iridium(III) (abbreviation: $[Ir(iPrpmi)_3]$) and tris[3-(2,6-dimethylphenyl)-7-methylimidazo[1,2-f]phenanthridinato]iridium(III) (abbreviation: $[Ir(dmpimpt\text{-}Me)_3]$); and an organometallic iridium complex in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: $[Ir(CF_3ppy)_2(pic)]$), and bis[2-(4',6'-difluorophenyl)pyridinato-N,$C^{2'}$]iridium(III) acetylacetonate (abbreviation: FIr(acac)). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: $[Ir(mppm)_3]$), tris(4-t-butyl-6-phenylpyrimidinato)iridium (III) (abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation: $[Ir(tBuppm)_2(acac)]$), (acetylacetonato)bis[6-(2-norbornyl)-4-phenylpyrimidinato]iridium(III) (abbreviation: $[Ir(nbppm)_2(acac)]$), (acetylacetonato)bis[5-methyl-6-(2-methylphenyl)-4-phenylpyrimidinato]iridium(III) (abbreviation: $[Ir(mpmppm)_2(acac)]$), and (acetylacetonato)bis(4,6-diphenylpyrimidinato)iridium(III) (abbreviation: $[Ir(dppm)_2(acac)]$); organometallic iridium complexes having a pyrazine skeleton, such as (acetylacetonato)bis(3,5-dimethyl-2-phenylpyrazinato)iridium(III) (abbreviation: $[Ir(mppr\text{-}Me)_2(acac)]$) and (acetylacetonato)bis(5-isopropyl-3-methyl-2-phenylpyrazinato)iridium(III) (abbreviation: $[Ir(mppr\text{-}iPr)_2(acac)]$); organometallic iridium complexes having a pyridine skeleton, such as tris(2-phenylpyridinato-N,$C^{2'}$)iridium(III) (abbreviation: $[Ir(ppy)_3]$), bis(2-phenylpyridinato-N,$C^{2'}$)iridium(III) acetylacetonate (abbreviation: $[Ir(ppy)_2(acac)]$), bis(benzo[h]quinolinato)iridium(III) acetylacetonate (abbreviation: $[Ir(bzq)_2(acac)]$), tris(benzo[h]quinolinato)iridium(III) (abbreviation: $[Ir(bzq)_3]$), tris(2-phenylquinolinato-N,$C^{2'}$)iridium(III) (abbreviation: $[Ir(pq)_3]$), and bis(2-phenylquinolinato-N,$C^{2'}$)iridium(III) acetylacetonate (abbreviation: $[Ir(pq)_2(acac)]$); and a rare earth metal complex such as tris(acetylacetonato) (monophenanthroline)terbium(III) (abbreviation: $[Tb(acac)_3(Phen)]$). These are mainly compounds that emit green phosphorescence and have an emission peak at 500 nm to 600 nm. Note that organometallic iridium complexes having a pyrimidine skeleton have distinctively high reliability and emission efficiency and thus are particularly preferable.

Other examples include organometallic iridium complexes having a pyrimidine skeleton, such as (diisobutyrylmethanato)bis[4,6-bis(3-methylphenyl)pyrimidinato] iridium(III) (abbreviation: $[Ir(5mdppm)_2(dibm)]$), bis[4,6-bis(3-methylphenyl)pyrimidinato](dipivaloylmethanato) iridium(III) (abbreviation: $[Ir(5mdppm)_2(dpm)]$), and bis[4,6-di(naphthalen-1-yl)pyrimidinato](dipivaloylmethanato) iridium(III) (abbreviation: $[Ir(d1npm)_2(dpm)]$); organometallic iridium complexes having a pyrazine skeleton, such as (acetylacetonato)bis(2,3,5-triphenylpyrazinato)iridium(III) (abbreviation: $[Ir(tppr)_2(acac)]$), bis(2,3,5-triphenylpyrazinato)(dipivaloylmethanato)iridium(III) (abbreviation: $[Ir(tppr)_2(dpm)]$), and (acetylacetonato)bis[2,3-bis(4-fluorophenyl)quinoxalinato]iridium(III) (abbreviation: $[Ir(Fdpq)_2(acac)]$); organometallic iridium complexes having a pyridine skeleton, such as tris(1-phenylisoquinolinato-N,$C^{2'}$)iridium(III) (abbreviation: $[Ir(piq)_3]$) and bis(1-phenylisoquinolinato-N,$C^{2'}$)iridium(III) acetylacetonate (abbreviation: $[Ir(piq)_2(acac)]$); platinum complexes such as 2,3,7,8,12,13,17,18-octaethyl-21H,23H-porphyrinplatinum (II) (abbreviation: [PtOEP]); and rare earth metal complexes such as tris(1,3-diphenyl-1,3-propanedionato) (monophenanthroline)europium(III) (abbreviation: $[Eu(DBM)_3(Phen)]$) and tris[1-(2-thenoyl)-3,3,3-trifluoroacetonato] (monophenanthroline)europium(III) (abbreviation: $[Eu(TTA)_3(Phen)]$). These compounds emit red phosphorescence having an emission peak at 600 nm to 700 nm. Furthermore, the organometallic iridium complexes having a pyrazine skeleton can provide red light emission with favorable chromaticity.

Besides the above phosphorescent compounds, known phosphorescent substances may be selected and used.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2OEP$), which are represented by the following structural formulae.

[Chemical formulae 8]

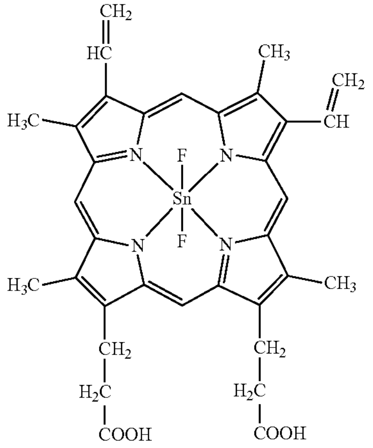

$SnF_2$(Proto IX)

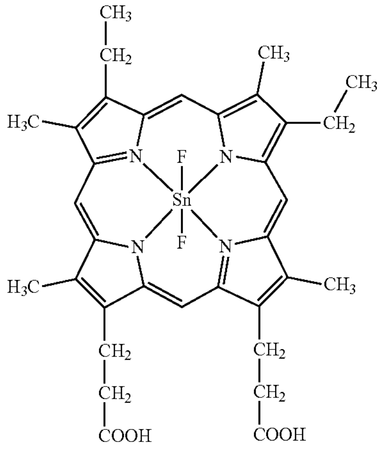

$SnF_2$(Meso IX)

-continued

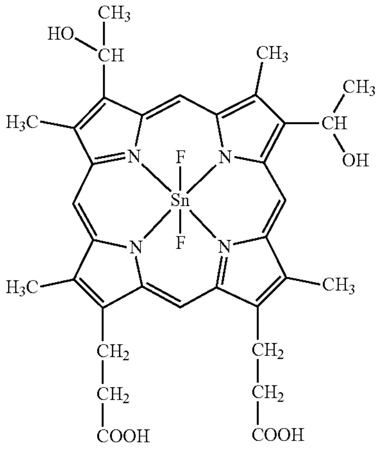

$SnF_2$(Hemato IX)

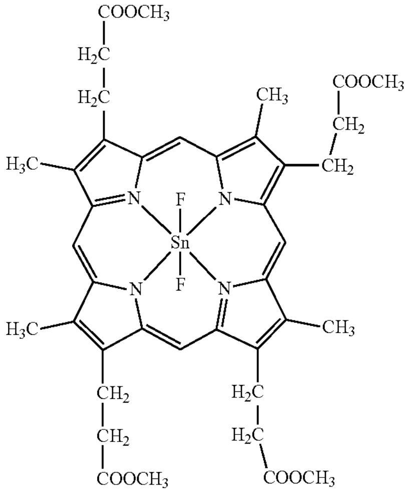

$SnF_2$(Copro III-4Me)

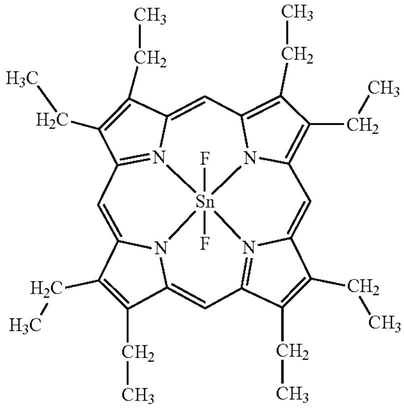

$SnF_2$(OEP)

-continued

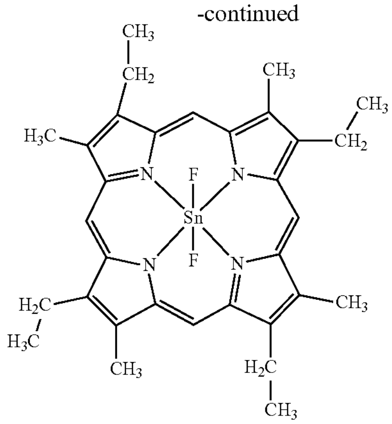

$SnF_2$(Etio I)

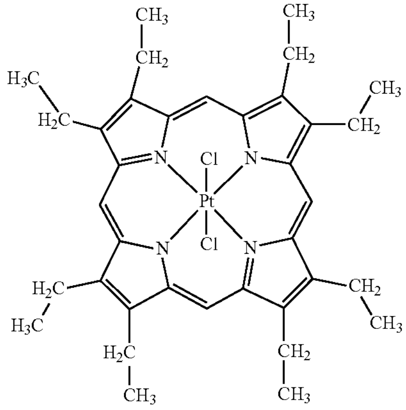

$PtCl_2OEP$

Alternatively, a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Such a heterocyclic compound is preferable because of having excellent electron-transport and hole-transport properties owing to a π-electron rich heteroaromatic ring and a π-electron deficient heteroaromatic ring. Among skeletons having the π-electron deficient heteroaromatic ring, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high accepting properties and high reliability. Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. A dibenzofuran skeleton is preferable as a furan skeleton, and a dibenzothiophene skeleton is preferable as a thiophene skeleton. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which the π-electron rich heteroaromatic ring is directly bonded to the π-electron deficient heteroaromatic ring is particularly preferred because the electron-donating property of the π-electron rich heteroaromatic ring and the electron-accepting property of the π-electron deficient heteroaromatic ring are both improved, the energy difference between the S1 level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane or boranthrene, an aromatic ring or a heteroaromatic ring having a cyano group or a nitrile group such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical formulae 9]

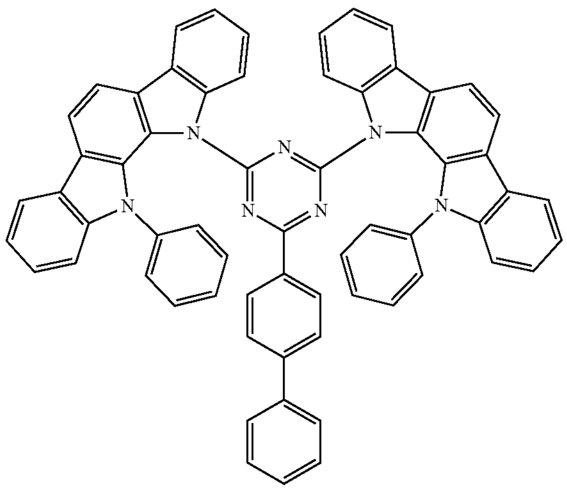

PIC-TRZ

-continued

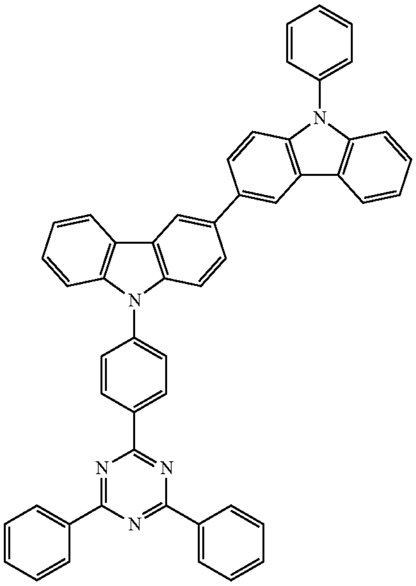

PCCzPTzn

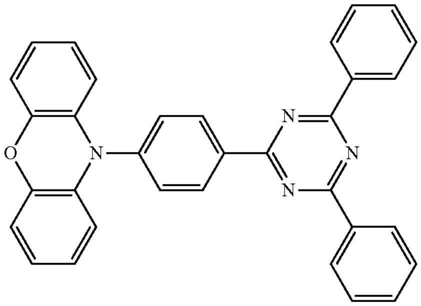

PXZ-TRZ

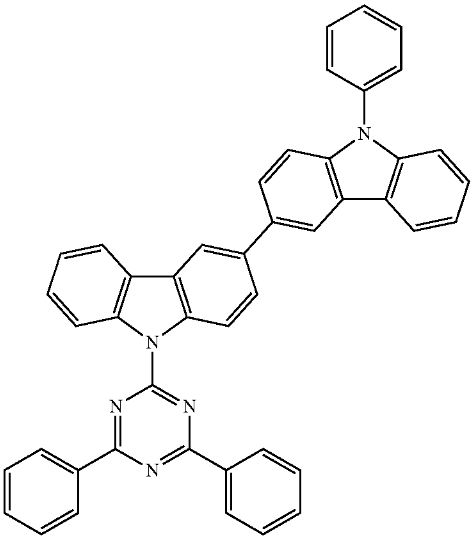

PCCzTzn

-continued

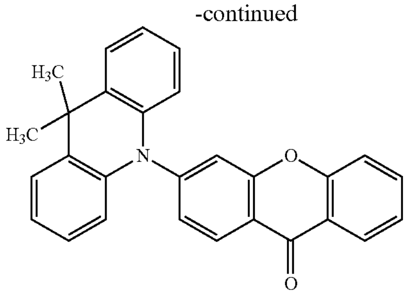

ACRXTN

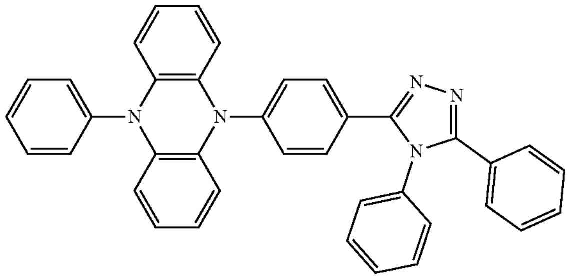

PPZ-3TPT

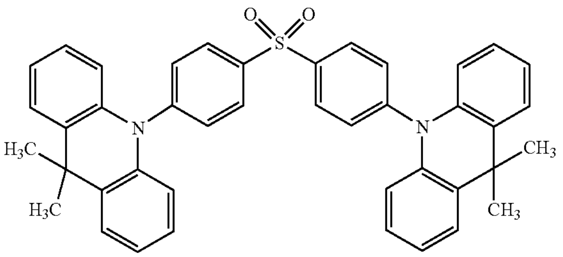

DMAC-DPS

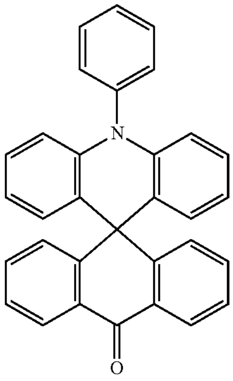

ACRSA

Note that a TADF material is a material having a small difference between the S1 level and the T1 level and a function of converting triplet excitation energy into singlet excitation energy by reverse intersystem crossing. Thus, a TADF material can upconvert triplet excitation energy into singlet excitation energy (i.e., reverse intersystem crossing) using a small amount of thermal energy and efficiently generate a singlet excited state. In addition, the triplet excitation energy can be converted into luminescence.

An exciplex whose excited state is formed of two kinds of substances has an extremely small difference between the S1 level and the T1 level and functions as a TADF material capable of converting triplet excitation energy into singlet excitation energy.

A phosphorescent spectrum observed at a low temperature (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between the S1 level and the T1 level of the TADF material is preferably smaller than or equal to 0.3 eV, further preferably smaller than or equal to 0.2 eV.

When a TADF material is used as the light-emitting substance, the S1 level of the host material is preferably higher than that of the TADF material. In addition, the T1 level of the host material is preferably higher than that of the TADF material.

As the host material in the light-emitting layer, various carrier-transport materials such as materials having an electron-transport property, materials having a hole-transport property, and the TADF materials can be used.

The material having a hole-transport property is preferably an organic compound having an aromatic amine skeleton or a π-electron rich heteroaromatic ring skeleton. Examples of the substance include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]-9,9'-spirobi[9H-fluoren]-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. In addition, the organic compound described in Embodiment 1 can also be used.

As the material having an electron-transport property, metal complexes such as bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc (II) (abbreviation: ZnBTZ); or an organic compound having a π-electron deficient heteroaromatic ring skeleton is preferable. Examples of the organic compound having a π-electron deficient heteroaromatic ring skeleton include 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-TH-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); heterocyclic compounds having a triazine skeleton such as 2-[3'-(9,9-dimethyl-9H-fluoren-2-yl)-1,1'-biphenyl-3-yl]-4,6-diphenyl-1,3,5-triazine (abbreviation: mFBPTzn), 2-[(1,1'-Biphenyl)-4-yl]-4-phenyl-6-[9,9'-spirobi(9H-fluoren)-2-yl]-1,3,5-triazine (abbreviation: BP-SFTzn), 2-{3-[3-(Benzo[b]naphtho[1,2-d]furan-8-yl)phenyl]phenyl}-4,6-diphenyl-1,3,5-triazine (abbreviation: mBnfBPTzn), and 2-{3-[3-(Benzo[b]naphtho[1,2-d]furan-6-yl)phenyl]phenyl}-4,6-diphenyl-1,3,5-triazine (abbreviation: mBnfBPTzn-02); and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton, the heterocyclic compound having a triazine skeleton, and the heterocyclic compound having a pyridine skeleton have high reliability and thus are preferable. In particular, the heterocyclic compound having a diazine (e.g., pyrimidine or pyrazine) skeleton has a high electron-transport property to contribute to a reduction in driving voltage.

As the TADF material that can be used as the host material, the above materials mentioned as the TADF material can also be used. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. Here, the TADF material functions as an energy donor, and the light-emitting substance functions as an energy acceptor.

This is very effective in the case where the light-emitting substance is a fluorescent substance. In that case, the S1 level of the TADF material is preferably higher than that of the fluorescent substance in order that high emission efficiency be achieved. Furthermore, the T1 level of the TADF material is preferably higher than the S1 level of the fluorescent substance. Therefore, the T1 level of the TADF material is preferably higher than that of the fluorescent substance.

It is also preferable to use a TADF material that emits light whose wavelength overlaps with the wavelength on a lowest-energy-side absorption band of the fluorescent substance. This enables smooth transfer of excitation energy from the TADF material to the fluorescent substance and accordingly enables efficient light emission, which is preferable.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton which causes light emission) of the fluorescent substance. As the protective group, a substituent having no π bond and a saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituents having no π bond are poor in carrier transport performance, whereby the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a π bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

In the case where a fluorescent substance is used as the light-emitting substance, a material having an anthracene skeleton is favorably used as the host material. The use of a substance having an anthracene skeleton as the host material for the fluorescent substance makes it possible to obtain a light-emitting layer with high emission efficiency and high durability. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: αN-PNPAnth). Note that CzPA, cgDBCzPA, 2mBnfPPA, and PCzPA have excellent characteristics and thus are preferably selected.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The weight ratio of the content of the material having a hole-transport property to the content of the material having an electron-transport property may be 1:19 to 19:1.

Note that a phosphorescent substance can be used as part of the mixed material. When a fluorescent substance is used as the light-emitting substance, a phosphorescent substance can be used as an energy donor for supplying excitation energy to the fluorescent substance.

An exciplex may be formed of these mixed materials. When these mixed materials are selected so as to form an exciplex that exhibits light emission whose wavelength overlaps with the wavelength on a lowest-energy-side absorption band of the light-emitting substance, energy can be transferred smoothly and light emission can be obtained efficiently, which is preferable. The use of such a structure is preferable because the driving voltage can also be reduced.

Note that at least one of the materials forming an exciplex may be a phosphorescent substance. In this case, triplet excitation energy can be efficiently converted into singlet excitation energy by reverse intersystem crossing.

Combination of a material having an electron-transport property and a material having a hole-transport property whose HOMO level is higher than or equal to that of the material having an electron-transport property is preferable for forming an exciplex efficiently. In addition, the LUMO level of the material having a hole-transport property is preferably higher than or equal to the LUMO level of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

The formation of an exciplex can be confirmed by a phenomenon in which the emission spectrum of the mixed film in which the material having a hole-transport property and the material having an electron-transport property are mixed is shifted to the longer wavelength side than the emission spectra of each of the materials (or has another peak on the longer wavelength side) observed by comparison of the emission spectra of the material having a hole-transport property, the material having an electron-transport property, and the mixed film of these materials, for example. Alternatively, the formation of an exciplex can be confirmed by a difference in transient response, such as a phenomenon in which the transient PL lifetime of the mixed film has longer lifetime components or has a larger proportion of delayed components than that of each of the materials, observed by comparison of transient photoluminescence (PL) of the material having a hole-transport property, the material having an electron-transport property, and the mixed film of the materials. The transient PL can be rephrased as transient electroluminescence (EL). That is, the formation of an exciplex can also be confirmed by a difference in transient response observed by comparison of the transient EL of the material having a hole-transport property, the material having an electron-transport property, and the mixed film of the materials.

An electron-transport layer 114 contains a substance having an electron-transport property. As the substance having an electron-transport property, it is possible to use any of the above-listed substances having electron-transport properties that can be used as the host material.

Note that the electron-transport layer preferably includes a material having an electron-transport property and an alkali metal, an alkaline earth metal, a compound thereof, or a complex thereof. The electron mobility of the material included in the electron-transport layer 114 in the case where the square root of the electric field strength [V/cm] is 600 is preferably higher than or equal to $1\times10^{-7}$ $cm^2/Vs$ and lower than or equal to $5\times10^{-5}$ $cm^2/Vs$. The amount of electrons injected into the light-emitting layer can be controlled by the reduction in the electron-transport property of the electron-transport layer 114, whereby the light-emitting layer can be prevented from having excess electrons. It is particularly preferable that this structure be employed when the hole-injection layer is formed using a composite material that includes a material having a hole-transport property with a relatively deep HOMO level of −5.7 eV or higher and −5.4 eV or lower, in which case the light-emitting device can have a long lifetime. In this case, the material having an electron-transport property preferably has a HOMO level of −6.0 eV or higher. The material having an electron-transport property is preferably an organic compound having an anthracene skeleton and further preferably an organic compound having both an anthracene skeleton and a heterocyclic skeleton. The heterocyclic skeleton is preferably a nitrogen-containing five-membered ring skeleton or a nitrogen-containing six-membered ring skeleton, and particularly preferably a nitrogen-containing five-membered ring skeleton or a nitrogen-containing six-membered ring skeleton including two heteroatoms in the ring, such as a pyrazole ring, an imidazole ring, an oxazole ring, a thiazole ring, a pyrazine ring, a pyrimidine ring, or a pyridazine ring. In addition, it is preferable that the alkali metal, the alkaline earth metal, the compound thereof, or the complex thereof have a 8-hydroxyquinolinato structure. Specific examples include 8-hydroxyquinolinato-lithium (abbreviation: Liq) and 8-hydroxyquinolinato-sodium (abbreviation: Naq). In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) of the alkali metal, the alkaline earth metal, the compound, or the complex can also be used. There is preferably a difference in the concentration (including 0) of the alkali metal, the alkaline earth metal, the compound thereof, or the complex thereof in the electron-transport layer in the thickness direction.

A layer containing an alkali metal, an alkaline earth metal, or a compound thereof such as lithium fluoride (LiF), cesium fluoride (CsF), calcium fluoride ($CaF_2$), or 8-hydroxyquinolinato-lithium (Liq) may be provided as the electron-injection layer 115 between the electron-transport layer 114 and the second electrode 102. For example, an electride or a layer that is formed using a substance having an electron-transport property and that includes an alkali metal, an alkaline earth metal, or a compound thereof can be used as the electron-injection layer 115. Examples of the electride include a substance in which electrons are added at high concentration to calcium oxide-aluminum oxide.

Note that as the electron-injection layer 115, it is possible to use a layer containing a substance that has an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, a light-emitting device including the layer can have high external quantum efficiency.

Figure 3B:
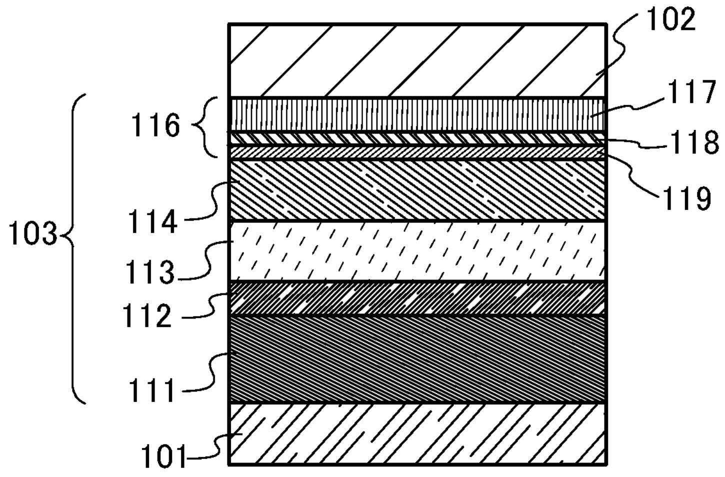

Instead of the electron-injection layer 115, a charge-generation layer 116 may be provided (FIG. 3B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the second electrode 102 serving as a cathode; thus, the light-emitting device operates. Since the organic compound of one embodiment of the present invention has a low refractive index, using the organic compound for the p-type layer 117 enables the light-emitting device to have high external quantum efficiency.

Note that the charge-generation layer 116 preferably includes an electron-relay layer 118 and/or an electron-injection buffer layer 119 in addition to the p-type layer 117.

The electron-relay layer 118 includes at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, further preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

For the second electrode 102, a metal, an alloy, an electrically conductive compound, or a mixture thereof each having a low work function (specifically, lower than or equal to 3.8 eV) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the second electrode 102 and the electron-transport layer, for the second electrode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an ink-jet method, a spin coating method, or the like. Alternatively, a wet process using a sol-gel method or a wet process using a paste of a metal material may be employed.

Furthermore, any of a variety of methods can be used for forming the EL layer 103, regardless of a dry method or a wet method. For example, a vacuum evaporation method, a gravure printing method, an offset printing method, a screen printing method, an ink-jet method, a spin coating method, or the like may be used.

Different methods may be used to form the electrodes or the layers described above.

The structure of the layers provided between the first electrode 101 and the second electrode 102 is not limited to the above-described structure. Preferably, a light-emitting region where holes and electrons recombine is positioned away from the first electrode 101 and the second electrode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of a light-emitting device with a structure in which a plurality of light-emitting units are stacked (this type of light-emitting device is also referred to as a stacked or tandem light-emitting device) is described with reference to FIG. 3C. This light-emitting device includes a plurality of light-emitting units between an anode and a cathode. One light-emitting unit has substantially the same structure as the EL layer 103 illustrated in FIG. 3A. In other words, the light-emitting device illustrated in FIG. 3A or 3B includes a single light-emitting unit, and the light-emitting device illustrated in FIG. 3C includes a plurality of light-emitting units.

Figure 3C:
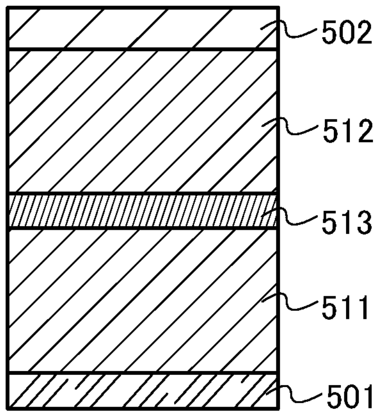

In FIG. 3C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 illustrated in FIG. 3A, and the materials given in the description for FIG. 3A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the anode 501 and the cathode 502. That is, in FIG. 3C, the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 3B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side and thus, an electron-injection layer is not necessarily formed in the light-emitting unit on the anode side.

The light-emitting device having two light-emitting units is described with reference to FIG. 3C; however, one embodiment of the present invention can also be applied to a light-emitting device in which three or more light-emitting units are stacked. With a plurality of light-emitting units partitioned by the charge-generation layer 513 between a pair of electrodes as in the light-emitting device of this embodiment, it is possible to provide a long-life element which can emit light with high luminance at a low current density. A light-emitting apparatus which can be driven at a low voltage and has low power consumption can be provided.

When the emission colors of the light-emitting units are different, light emission of a desired color can be obtained from the light-emitting device as a whole. For example, in a light-emitting device having two light-emitting units, the emission colors of the first light-emitting unit may be red and green and the emission color of the second light-emitting unit may be blue, so that the light-emitting device can emit white light as the whole.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting apparatus including the light-emitting device described in Embodiment 2 is described.

Figure 4A:
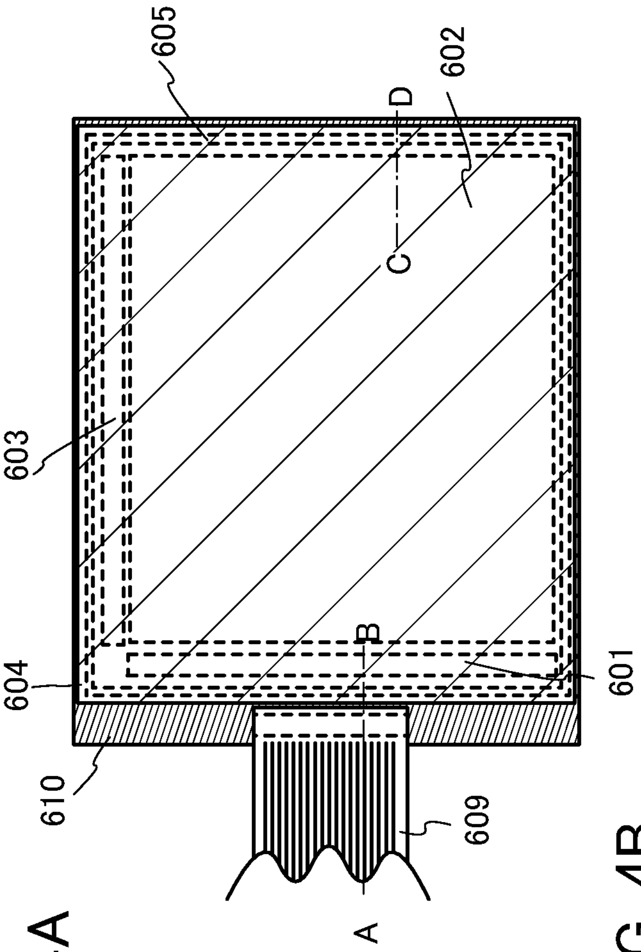
FIGS. 4A and 4B illustrate an active matrix light-emitting apparatus.
Figure 4B:
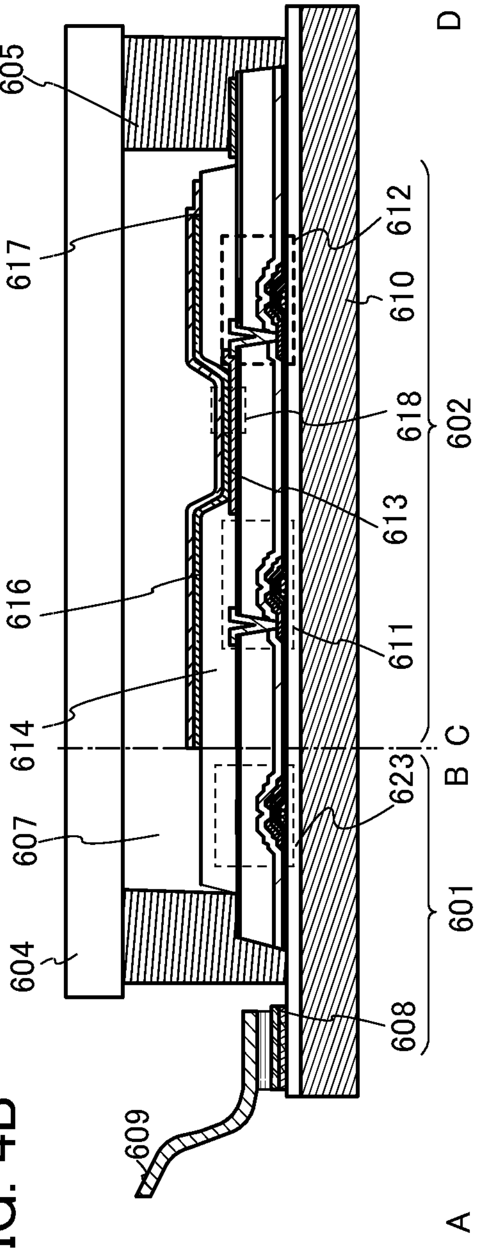

In this embodiment, the light-emitting apparatus manufactured using the light-emitting device described in Embodiment 2 is described with reference to FIGS. 4A and 4B. Note that FIG. 4A is a top view of the light-emitting apparatus and FIG. 4B is a cross-sectional view taken along the lines A-B and C-D in FIG. 4A. This light-emitting apparatus includes a driver circuit portion (source line driver circuit) 601, a pixel portion 602, and a driver circuit portion (gate line driver circuit) 603, which are to control light emission of a light-emitting device and illustrated with dotted lines. Reference numeral 604 denotes a sealing substrate; 605, a sealing material; and 607, a space surrounded by the sealing material 605.

Reference numeral 608 denotes a lead wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting apparatus in the present specification includes, in its category, not only the light-emitting apparatus itself but also the light-emitting apparatus provided with the FPC or the PWB.

Next, a cross-sectional structure is described with reference to FIG. 4B. The driver circuit portions and the pixel portion are formed over an element substrate 610; FIG. 4B shows the source line driver circuit 601, which is a driver circuit portion, and one pixel in the pixel portion 602.

The element substrate 610 may be a substrate containing glass, quartz, an organic resin, a metal, an alloy, or a semiconductor or a plastic substrate formed of fiber reinforced plastic (FRP), poly(vinyl fluoride) (PVF), polyester, or acrylic resin.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. It is preferable that a semiconductor having crystallinity be used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic apparatus with extremely low power consumption can be obtained.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit portion 601. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

Note that to cover an end portion of the first electrode 613, an insulator 614 is formed, for which a positive photosensitive acrylic resin film is used here.

In order to improve coverage with an EL layer or the like which is formed later, the insulator 614 is formed to have a curved surface with curvature at its upper or lower end portion. For example, in the case where positive photosensitive acrylic resin is used as a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance, favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, and Ca, or an alloy or a compound thereof, such as MgAg, MgIn, and AlLi) is preferably used. In the case where light generated in the EL layer 616 is transmitted through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting device is formed with the first electrode 613, the EL layer 616, and the second electrode 617. The light-emitting device is the light-emitting device described in Embodiment 2. In the light-emitting apparatus of this embodiment, the pixel portion, which includes a plurality of light-emitting devices, may include both the light-emitting device described in Embodiment 2 and a light-emitting device having a different structure.

The sealing substrate 604 is attached to the element substrate 610 with the sealing material 605, so that a light-emitting device 618 is provided in the space 607 surrounded by the element substrate 610, the sealing substrate 604, and the sealing material 605. The space 607 may be filled with a filler, or may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material not be permeable to moisture or oxygen as much as possible. As the sealing substrate 604, a glass substrate, a quartz substrate, or a plastic substrate formed of fiber reinforced plastic (FRP), poly(vinyl fluoride) (PVF), polyester, and acrylic resin can be used.

Although not illustrated in FIGS. 4A and 4B, a protective film may be provided over the second electrode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material through which an impurity such as water does not permeate easily. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting apparatus manufactured using the light-emitting device described in Embodiment 2 can be obtained.

The light-emitting apparatus in this embodiment is manufactured using the light-emitting device described in Embodiment 2 and thus can have favorable characteristics. Specifically, since the light-emitting device described in Embodiment 2 has high emission efficiency, the light-emitting apparatus can achieve low power consumption.

Figure 5A:
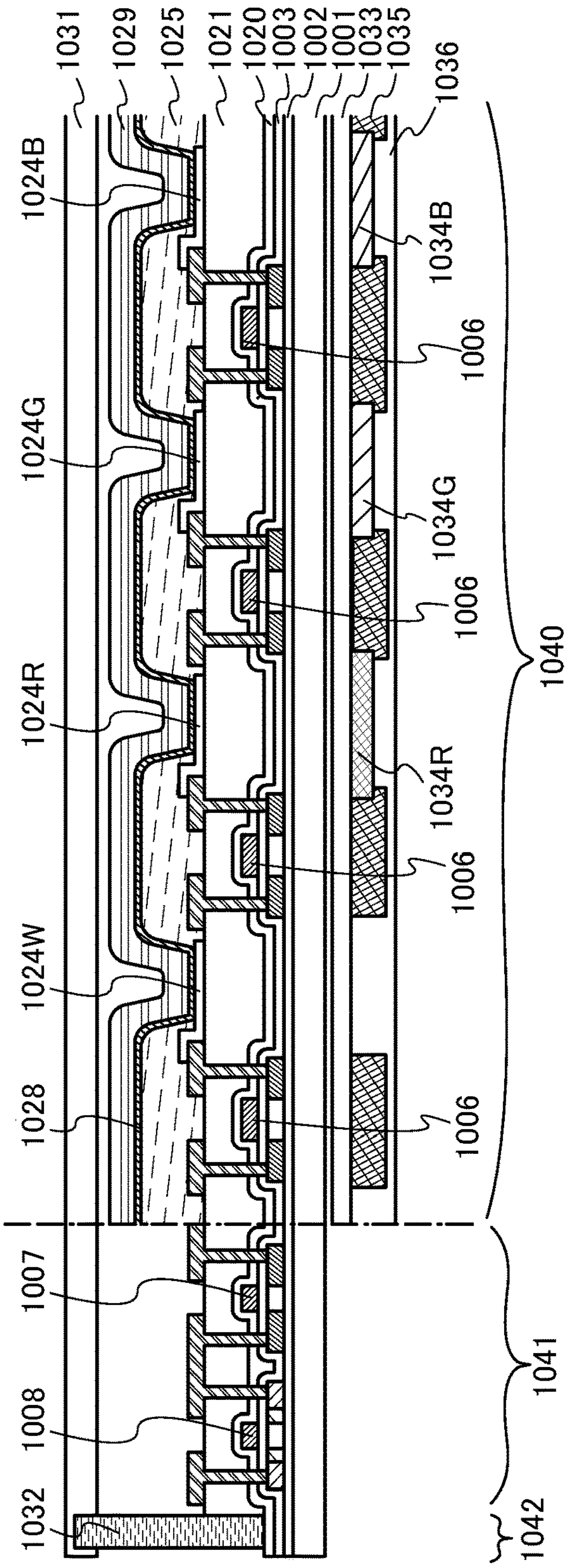
FIGS. 5A and 5B each illustrate an active matrix light-emitting apparatus.
Figure 5B:
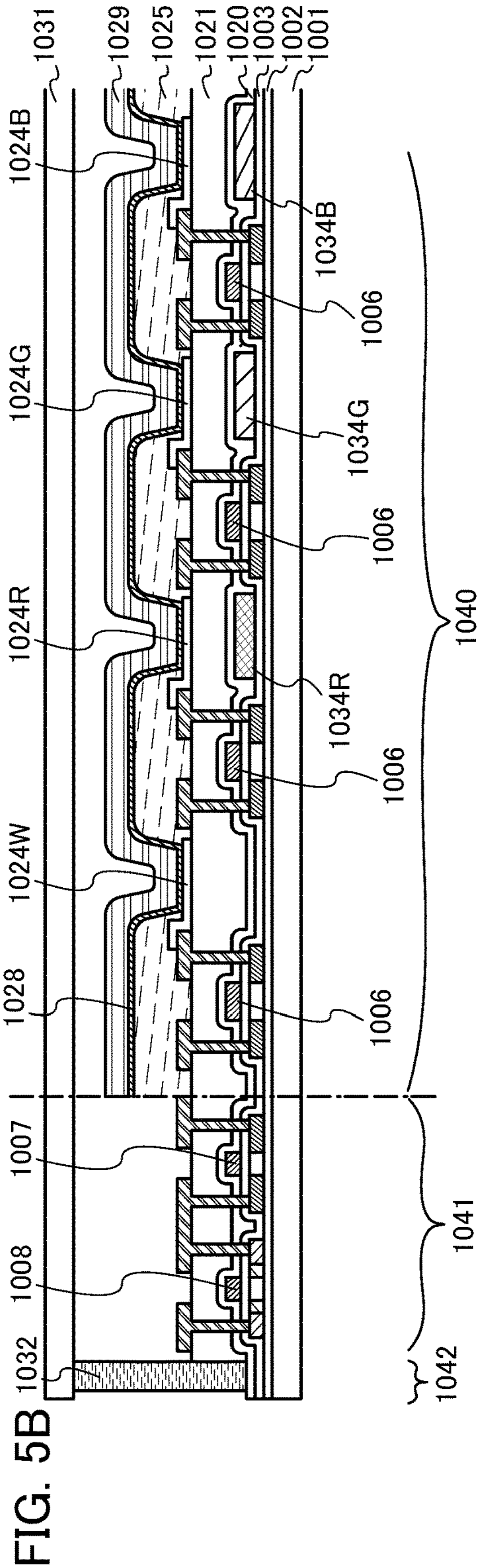

FIGS. 5A and 5B each illustrate an example of a light-emitting apparatus in which full color display is achieved by formation of a light-emitting device exhibiting white light emission and with the use of coloring layers (color filters) and the like. In FIG. 5A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition 1025, an EL layer 1028, a second electrode 1029 of the light-emitting devices, a sealing substrate 1031, a sealing material 1032, and the like are illustrated.

In FIG. 5A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 5A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, green, or blue, an image can be displayed using pixels of the four colors.

FIG. 5B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 6:
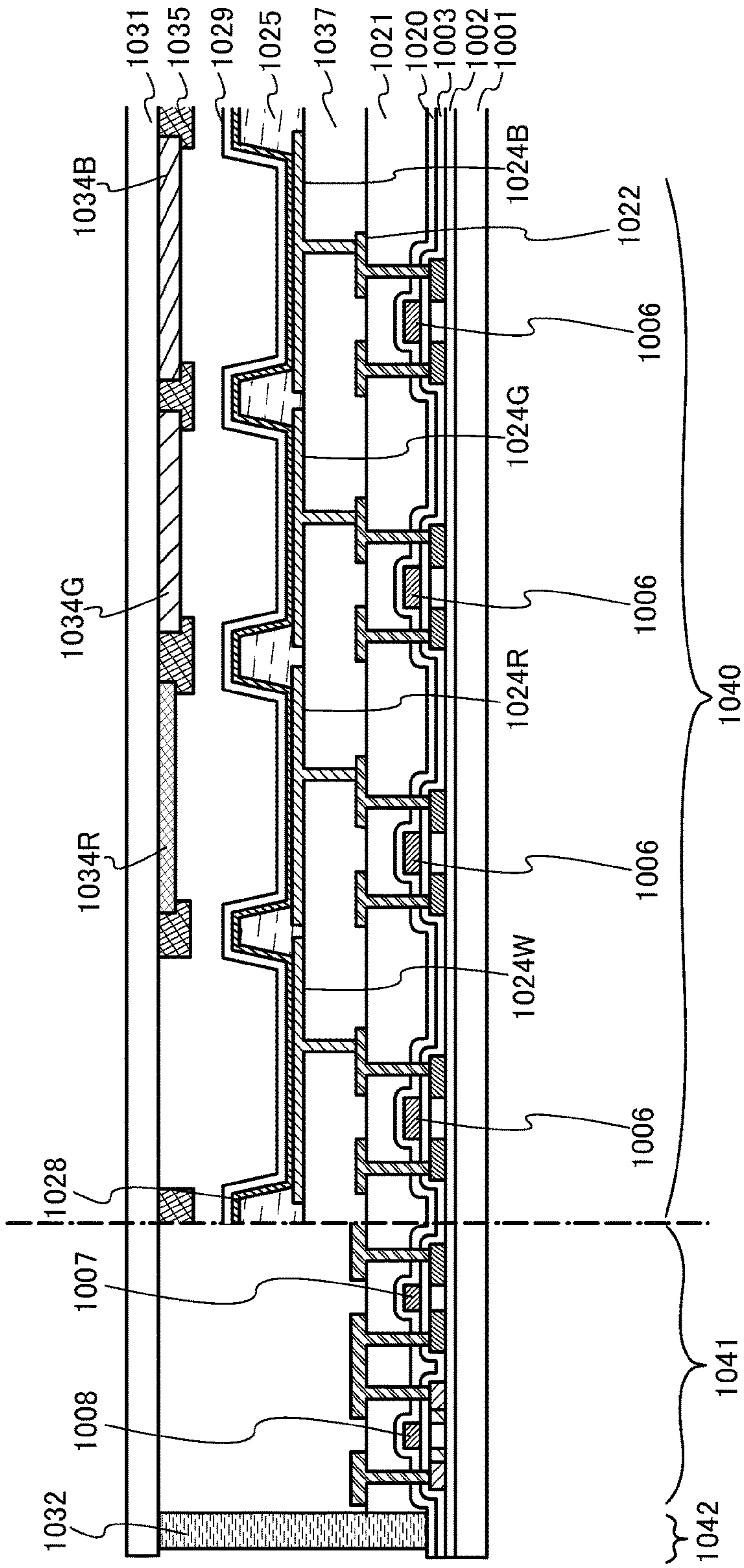
FIG. 6 illustrates an active matrix light-emitting apparatus.

The above-described light-emitting apparatus is a light-emitting apparatus having a structure in which light is extracted from the substrate 1001 side where FETs are formed (a bottom emission structure), but may be a light-emitting apparatus having a structure in which light is extracted from the sealing substrate 1031 side (a top emission structure). FIG. 6 is a cross-sectional view of a light-emitting apparatus having a top emission structure. In this case, a substrate which does not transmit light can be used as the substrate 1001. The process up to the step of forming a connection electrode which connects the FET and the anode of the light-emitting device is performed in a manner similar to that of the light-emitting apparatus having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting devices each serve as an anode here, but may serve as a cathode. Furthermore, in the case of a light-emitting apparatus having a top emission structure as illustrated in FIG. 6, the first electrodes are preferably reflective electrodes. The EL layer 1028 is formed to have a structure similar to the structure of the EL layer 103, which is described in Embodiment 2, with which white light emission can be obtained.

In the case of a top emission structure as illustrated in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display using four colors of red, yellow, green, and blue or three colors of red, green, and blue may be performed.

In the light-emitting apparatus having a top emission structure, a microcavity structure can be favorably employed. A light-emitting device with a microcavity structure is formed with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode has a visible light reflectivity of 40% to 100% preferably 70% to 100%, and a resistivity of $1\times10^{-2}$ Ωcm or lower. In addition, the semi-transmissive and semi-reflective electrode has a visible light reflectivity of 20% to 80%, preferably 40% to 70%, and a resistivity of $1\times10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and λ is a wavelength of color to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting device described above may be combined with a plurality of EL layers; for example, a light-emitting device may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because the luminance can be increased owing to yellow light emission and each subpixel can employ a microcavity structure suitable for wavelengths of the corresponding color.

The light-emitting apparatus in this embodiment is manufactured using the light-emitting device described in Embodiment 2 and thus can have favorable characteristics. Specifically, since the light-emitting device described in Embodiment 2 has high emission efficiency, the light-emitting apparatus can achieve low power consumption.

Figure 7A:
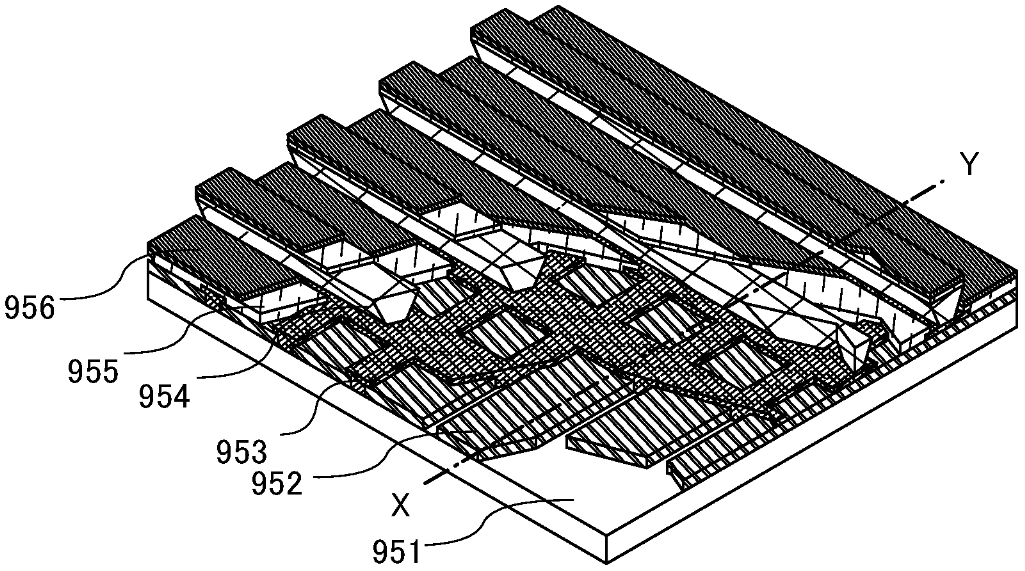
FIGS. 7A and 7B illustrate a passive matrix light-emitting apparatus.
Figure 7B:
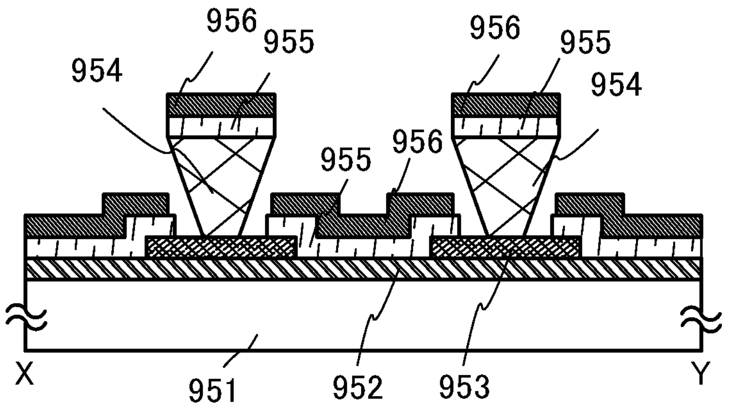

An active matrix light-emitting apparatus is described above, whereas a passive matrix light-emitting apparatus is described below. FIGS. 7A and 7B illustrate a passive matrix light-emitting apparatus manufactured using the present invention. Note that FIG. 7A is a perspective view of the light-emitting apparatus, and FIG. 7B is a cross-sectional view taken along the line X-Y in FIG. 7A. In FIGS. 7A and 7B, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side of the trapezoid which is parallel to the surface of the insulating layer 953 and is in contact with the insulating layer 953) is shorter than the upper side (a side of the trapezoid which is parallel to the surface of the insulating layer 953 and is not in contact with the insulating layer 953). The partition layer 954 thus provided can prevent defects in the light-emitting device due to static electricity or others. The passive-matrix light-emitting apparatus also includes the light-emitting device described in Embodiment 2; thus, the light-emitting apparatus can have high reliability or low power consumption.

Since many minute light-emitting devices arranged in a matrix in the light-emitting apparatus described above can each be controlled, the light-emitting apparatus can be suitably used as a display device for displaying images.

This embodiment can be freely combined with any of the other embodiments.

Embodiment 4

Figure 8A:
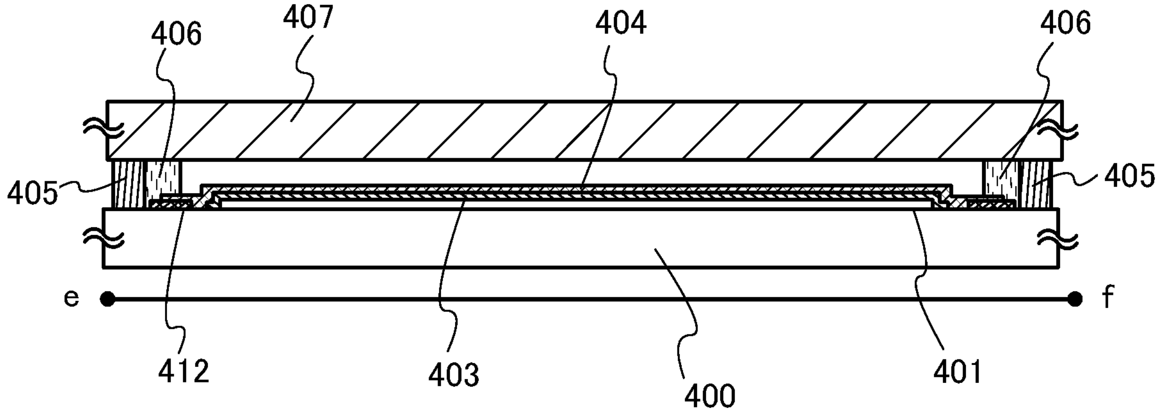
FIGS. 8A and 8B illustrate a lighting device.
Figure 8B:
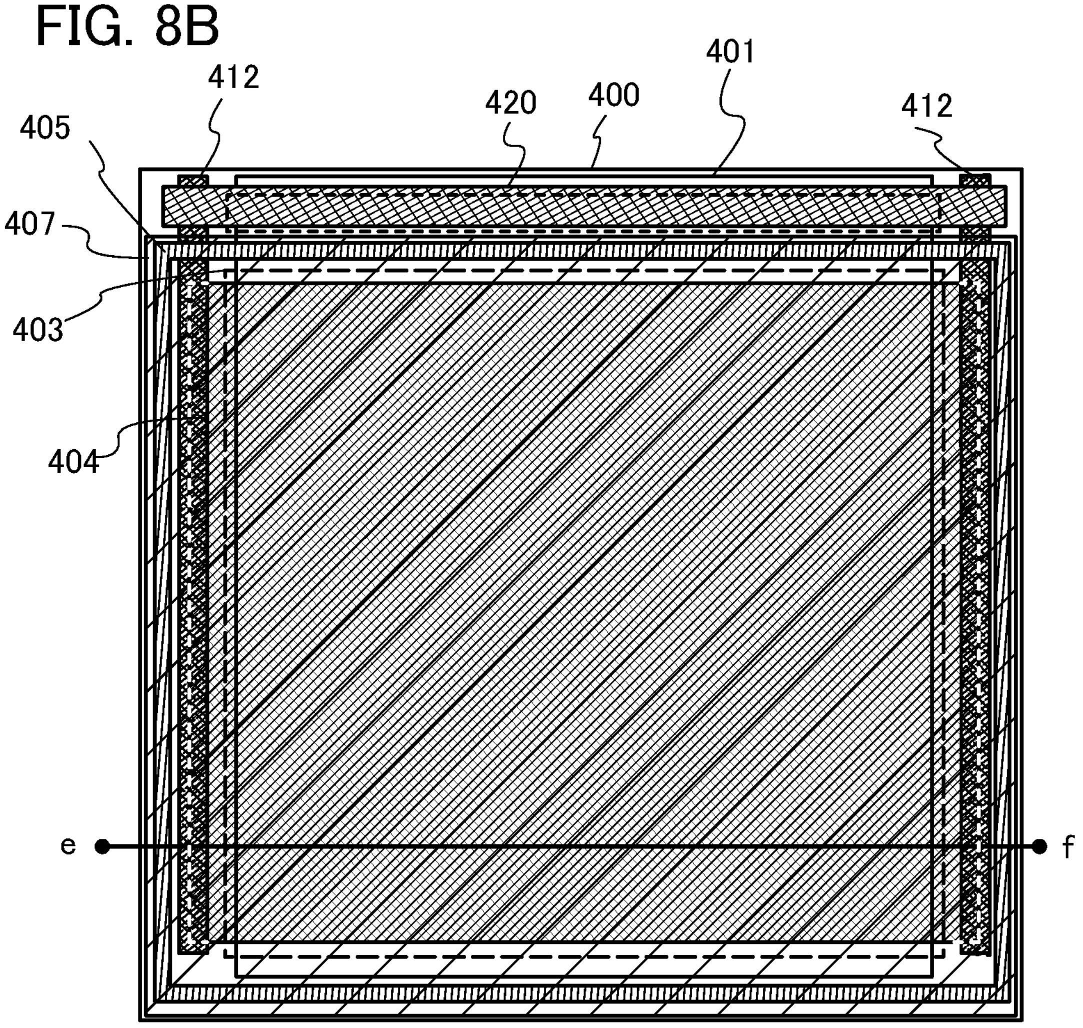

In this embodiment, an example in which the light-emitting device described in Embodiment 2 is used for a lighting device will be described with reference to FIGS. 8A and 8B. FIG. 8B is a top view of the lighting device, and FIG. 8A is a cross-sectional view taken along the line e-f in FIG. 8B.

In the lighting device in this embodiment, a first electrode 401 is formed over a substrate 400 which is a support and has a light-transmitting property. The first electrode 401 corresponds to the first electrode 101 in Embodiment 1. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to, for example, the structure of the EL layer 103 in Embodiment 1, or the structure in which the light-emitting units 511 and 512 and the charge-generation layer 513 are combined. Refer to the description for the structure.

The second electrode 404 is formed to cover the EL layer 403. The second electrode 404 corresponds to the second electrode 102 in Embodiment 1. The second electrode 404 is formed using a material having high reflectance when light is extracted through the first electrode 401 side. The second electrode 404 is connected to the pad 412, whereby voltage is applied.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device having low power consumption.

The substrate 400 provided with the light-emitting device having the above structure is fixed to a sealing substrate 407 with sealing materials 405 and 406 and sealing is performed, whereby the lighting device is completed. It is possible to use only either the sealing material 405 or the sealing material 406. The inner sealing material 406 (not shown in FIG. 8B) can be mixed with a desiccant which enables moisture to be adsorbed, increasing reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

The lighting device described in this embodiment includes as an EL element the light-emitting device described in Embodiment 2; thus, the light-emitting apparatus can consume less power.

Embodiment 5

In this embodiment, examples of electronic apparatuses each including the light-emitting device described in Embodiment 2 will be described. The light-emitting device described in Embodiment 2 has high emission efficiency and low power consumption. As a result, the electronic apparatuses described in this embodiment can each include a light-emitting portion having low power consumption.

Examples of the electronic apparatus including the above light-emitting device include television devices (also referred to as TV or television receivers), monitors for computers and the like, digital cameras, digital video cameras, digital photo frames, cellular phones (also referred to as mobile phones or mobile phone devices), portable game machines, portable information terminals, audio playback devices, and large game machines such as pachinko machines. Specific examples of these electronic apparatuses are shown below.

Figure 9A:
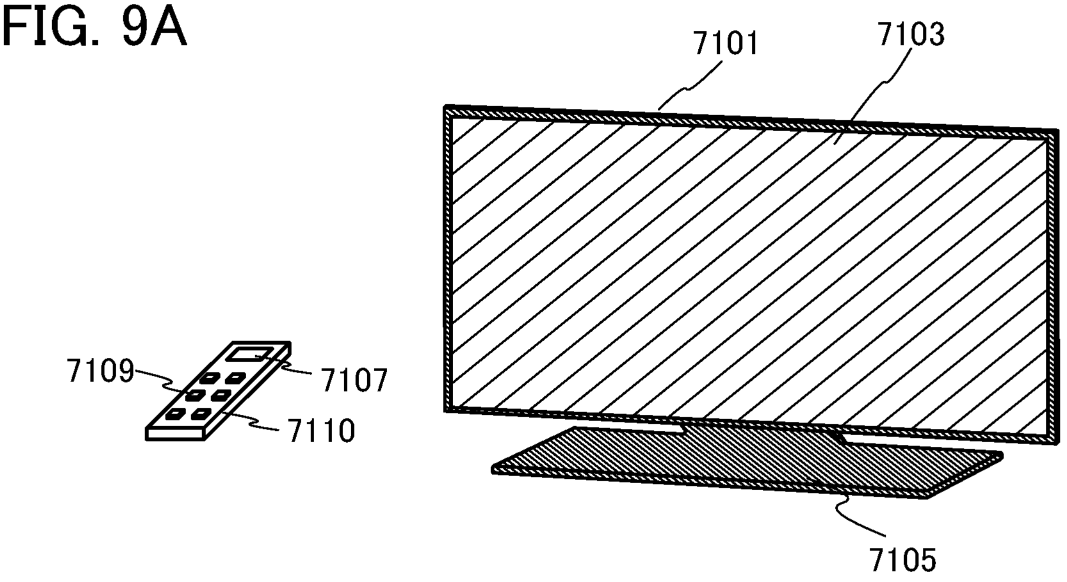
Figure 9A:
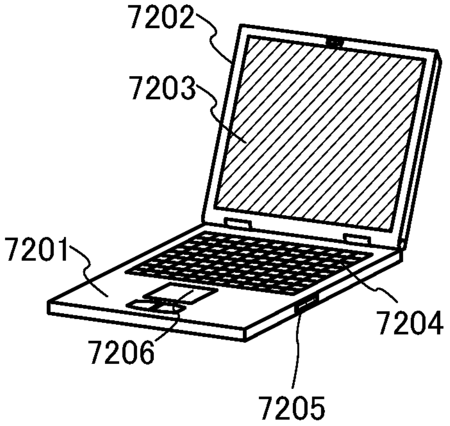
Figure 9A:
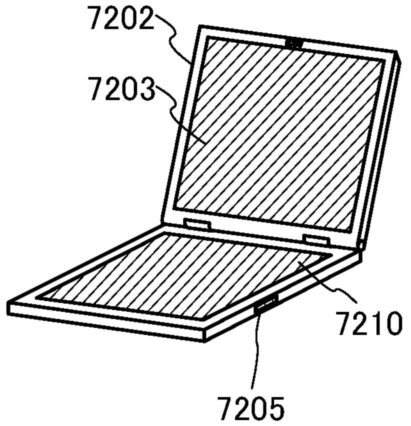

FIG. 9A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting devices described in Embodiment 2 are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 9B1 illustrates a computer, which includes a main body 7201, a housing 7202, a display portion 7203, a keyboard 7204, an external connection port 7205, a pointing device 7206, and the like. Note that this computer is manufactured using the light-emitting devices described in Embodiment 2 and arranged in a matrix in the display portion 7203. The computer illustrated in FIG. 9B1 may have a structure illustrated in FIG. 9B2. A computer illustrated in FIG. 9B2 is provided with a second display portion 7210 instead of the keyboard 7204 and the pointing device 7206. The second display portion 7210 is a touch panel, and input operation can be performed by touching display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

Figure 9C:
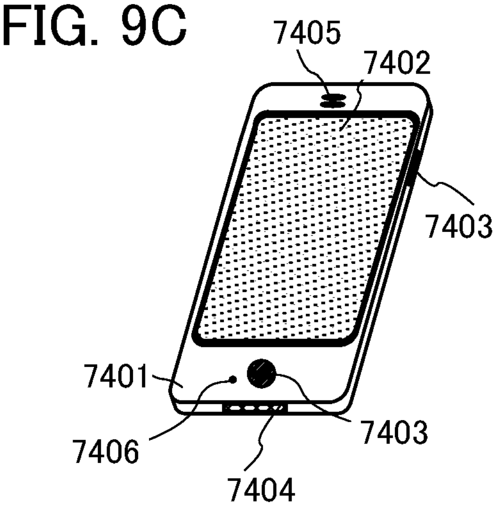

FIG. 9C illustrates an example of a portable terminal. A cellular phone is provided with a display portion 7402 incorporated in a housing 7401, operation buttons 7403, an external connection port 7404, a speaker 7405, a microphone 7406, and the like. Note that the cellular phone has the display portion 7402 including the light-emitting devices described in Embodiment 2 and arranged in a matrix.

When the display portion 7402 of the portable terminal illustrated in FIG. 9C is touched with a finger or the like, data can be input into the portable terminal. In this case, operations such as making a call and creating an e-mail can be performed by touching the display portion 7402 with a finger or the like.

The display portion 7402 has mainly three screen modes. The first mode is a display mode mainly for displaying images. The second mode is an input mode mainly for inputting information such as text. The third mode is a display-and-input mode in which the two modes, the display mode and the input mode, are combined.

For example, in the case of making a call or creating an e-mail, a text input mode mainly for inputting text is selected for the display portion 7402 so that text displayed on the screen can be input. In this case, it is preferable to display a keyboard or number buttons on almost the entire screen of the display portion 7402.

When a sensing device including a sensor such as a gyroscope sensor or an acceleration sensor for detecting inclination is provided inside the portable terminal, display on the screen of the display portion 7402 can be automatically changed in direction by determining the orientation of the portable terminal (whether the portable terminal is placed horizontally or vertically).

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken when the display portion 7402 is touched with the palm or the finger, whereby personal authentication can be performed. Furthermore, by providing a backlight or a sensing light source which emits near-infrared light in the display portion, an image of a finger vein, a palm vein, or the like can be taken.

Note that the structure described in this embodiment can be combined with any of the structures described in Embodiments 1 to 4 as appropriate.

As described above, the application range of the light-emitting apparatus having the light-emitting device described in Embodiment 2 is wide so that this light-emitting apparatus can be applied to electronic apparatuses in a variety of fields. By using the light-emitting device described in Embodiment 2, an electronic apparatus with low power consumption can be obtained.

Figure 10A:
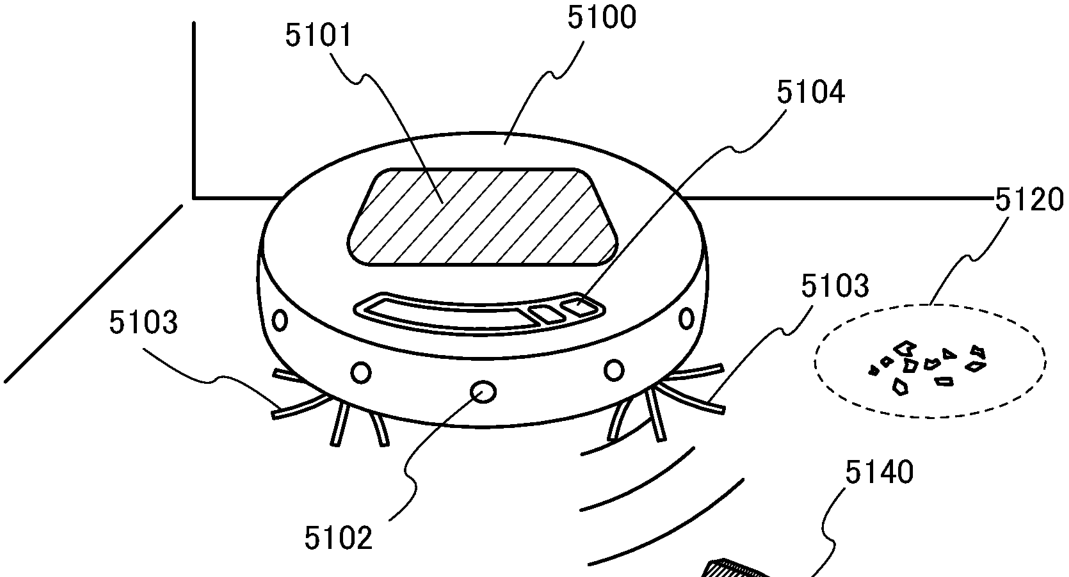
FIGS. 10A to 10C illustrate electronic apparatuses.
Figure 10A:
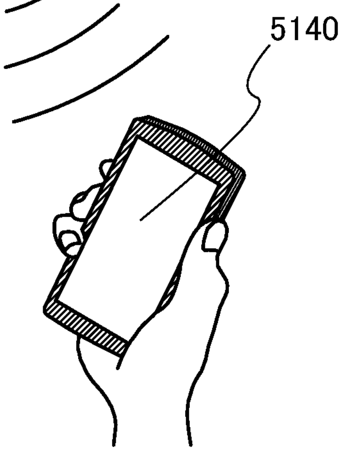

FIG. 10A is a schematic view illustrating an example of a cleaning robot.

A cleaning robot 5100 includes a display 5101 on its top surface, a plurality of cameras 5102 on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. The cleaning robot 5100 has a wireless communication means.

The cleaning robot 5100 is self-propelled, detects dust 5120, and sucks up the dust through the inlet provided on the bottom surface.

The cleaning robot 5100 can determine whether there is an obstacle such as a wall, furniture, or a step by analyzing images taken by the cameras 5102. When the cleaning robot 5100 detects an object that is likely to be caught in the brush 5103 (e.g., a wire) by image analysis, the rotation of the brush 5103 can be stopped.

The display 5101 can display the remaining capacity of a battery, the amount of collected dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic apparatus 5140 such as a smartphone. The portable electronic apparatus 5140 can display images taken by the cameras 5102. Accordingly, an owner of the cleaning robot 5100 can monitor his/her room even when the owner is not at home. The owner can also check the display on the display 5101 by the portable electronic apparatus 5140 such as a smartphone.

The light-emitting apparatus of one embodiment of the present invention can be used for the display 5101.

Figure 10B:
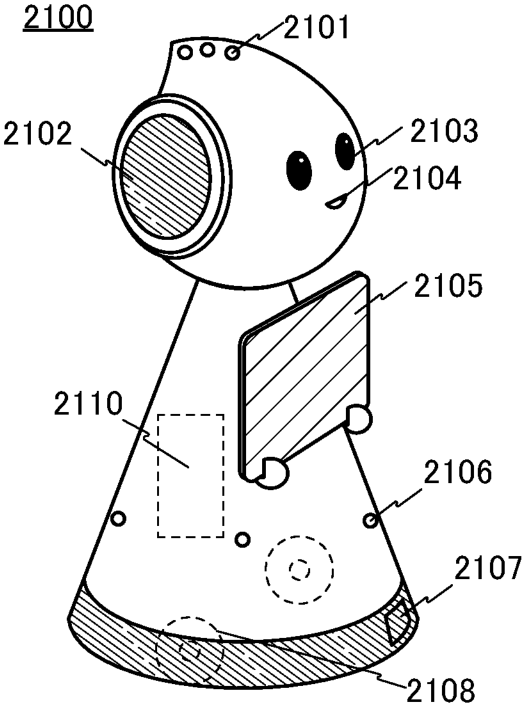

A robot 2100 illustrated in FIG. 10B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 10C:
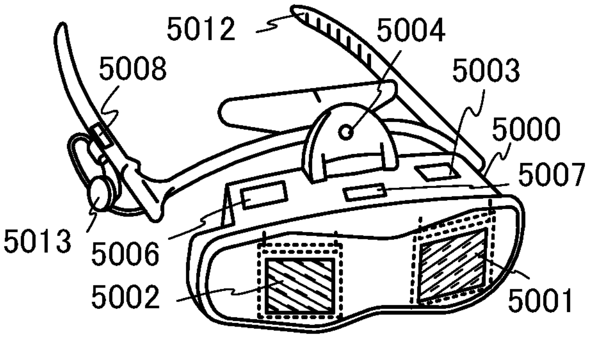

FIG. 10C illustrates an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 11:
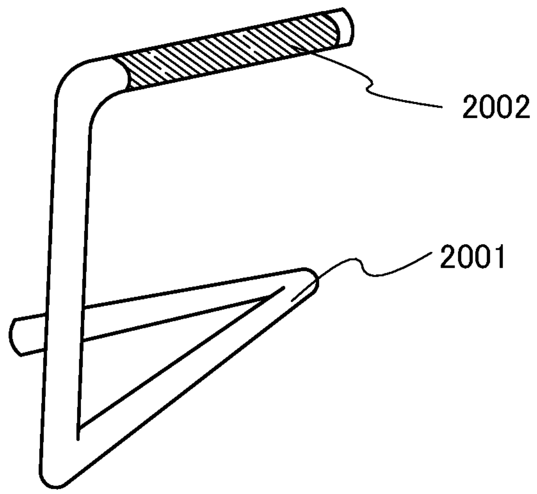
FIG. 11 illustrates a lighting device.

FIG. 11 illustrates an example in which the light-emitting device described in Embodiment 2 is used for a table lamp which is a lighting device. The table lamp illustrated in FIG. 11 includes a housing 2001 and a light source 2002, and the lighting device described in Embodiment 3 may be used for the light source 2002.

Figure 12:
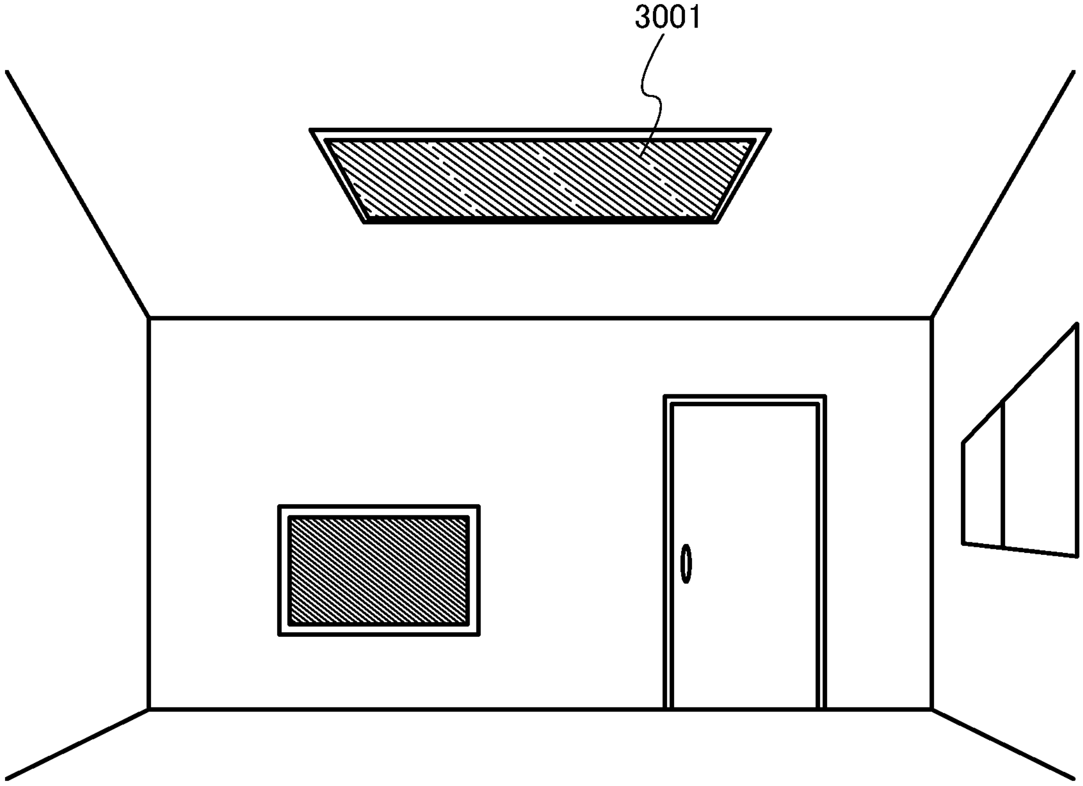
FIG. 12 illustrates a lighting device.

FIG. 12 illustrates an example in which the light-emitting device described in Embodiment 2 is used for an indoor lighting device 3001. Since the light-emitting device described in Embodiment 2 has high emission efficiency, the lighting device can have low power consumption. Furthermore, since the light-emitting device described in Embodiment 2 can have a large area, the light-emitting device can be used for a large-area lighting device. Furthermore, since the light-emitting device described in Embodiment 2 is thin, the light-emitting device can be used for a lighting device having a reduced thickness.

Figure 13:
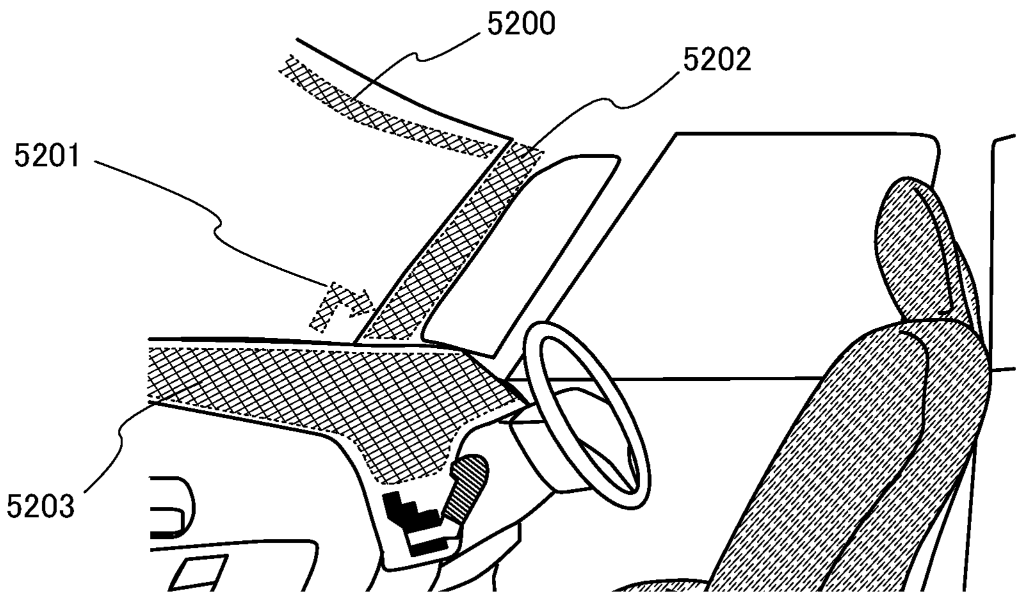
FIG. 13 illustrates in-vehicle display devices and lighting devices.

The light-emitting device described in Embodiment 2 can also be used for an automobile windshield, an automobile dashboard, or the like. FIG. 13 illustrates one mode in which the light-emitting devices described in Embodiment 2 are used for an automobile windshield, an automobile dashboard, and the like. Display regions 5200 to 5203 each include the light-emitting device described in Embodiment 2.

The display regions 5200 and 5201 are display devices which are provided in the automobile windshield and in which light-emitting devices each of which is described in Embodiment 2 are incorporated. The light-emitting devices described in Embodiment 2 can be formed into what is called a see-through display device, through which the opposite side can be seen, by including a first electrode and a second electrode formed of electrodes having a light-transmitting property. Such see-through display devices can be provided even in the automobile windshield without hindering the view. In the case where a driving transistor or the like is provided, a transistor having a light-transmitting property, such as an organic transistor including an organic semiconductor material or a transistor including an oxide semiconductor, is preferably used.

A display device incorporating the light-emitting device described in Embodiment 2 is provided in the display region 5202 in a pillar portion. The display region 5202 can compensate for the view hindered by the pillar by displaying an image taken by an imaging unit provided in the car body. Similarly, the display region 5203 provided in the dashboard portion can compensate for the view hindered by the car body by displaying an image taken by an imaging unit provided on the outside of the automobile. Thus, blind areas can be eliminated to enhance the safety. Images that compensate for the areas which a driver cannot see enable the driver to ensure safety easily and comfortably.

The display region 5203 can provide a variety of kinds of information such as navigation data, the speed, the number of rotations, air-condition setting, and the like. The content or layout of the display can be changed freely by a user as appropriate. Note that such information can also be displayed on the display regions 5200 to 5203. The display regions 5200 to 5203 can also be used as lighting devices.

Figure 14A:
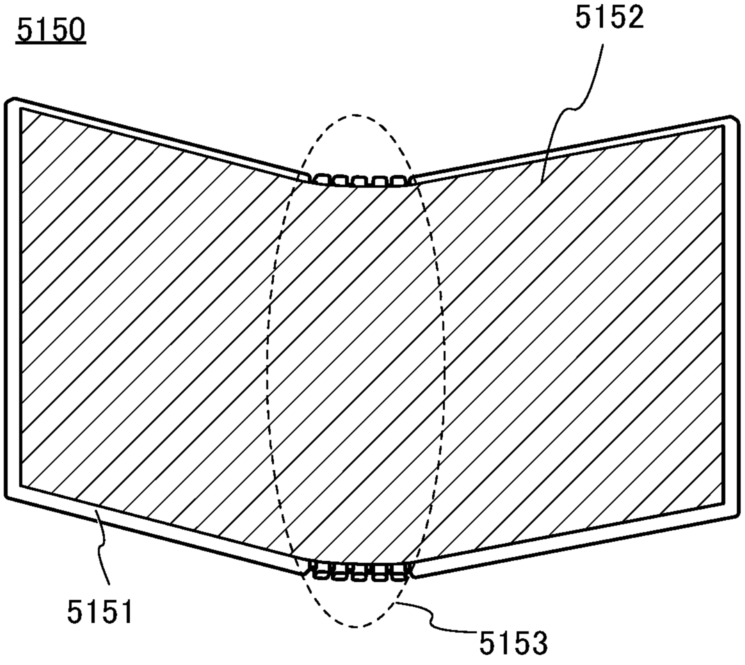
FIGS. 14A and 14B illustrate an electronic apparatus.
Figure 14B:
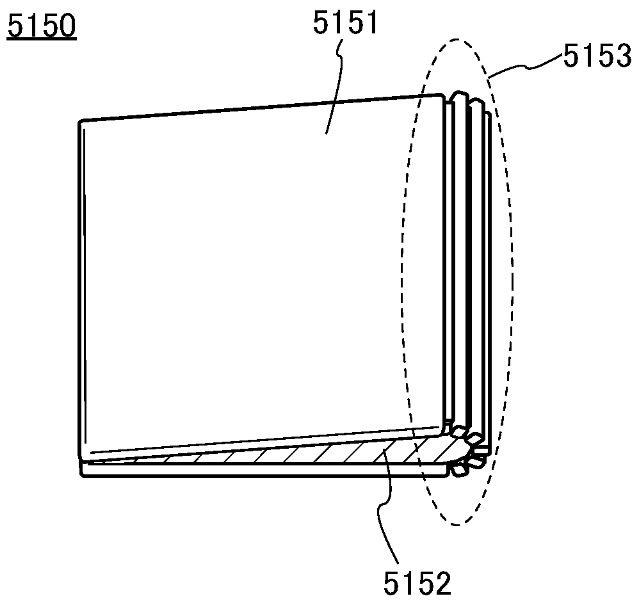

FIGS. 14A and 14B illustrate a foldable portable information terminal 5150. The foldable portable information terminal 5150 includes a housing 5151, a display region 5152, and a bend portion 5153. FIG. 14A illustrates the portable information terminal 5150 that is opened. FIG. 14B illustrates the portable information terminal 5150 that is folded. Despite its large display region 5152, the portable information terminal 5150 is compact in size and has excellent portability when folded.

The display region 5152 can be folded in half with the bend portion 5153. The bend portion 5153 includes a flexible member and a plurality of supporting members. When the display region is folded, the flexible member expands and the bend portion 5153 has a radius of curvature of greater than or equal to 2 mm, preferably greater than or equal to 3 mm.

Note that the display region 5152 may be a touch panel (an input/output device) including a touch sensor (an input device). The light-emitting apparatus of one embodiment of the present invention can be used for the display region 5152.

Figure 15A:
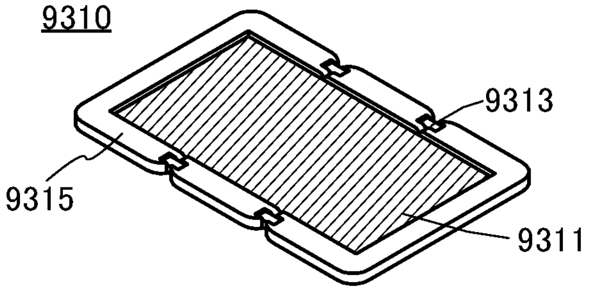
FIGS. 15A to 15C illustrate an electronic apparatus.
Figure 15B:
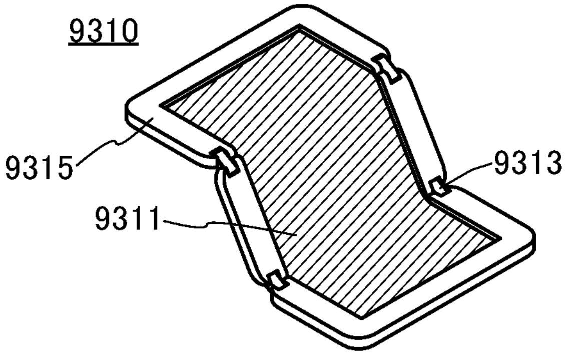
Figure 15C:
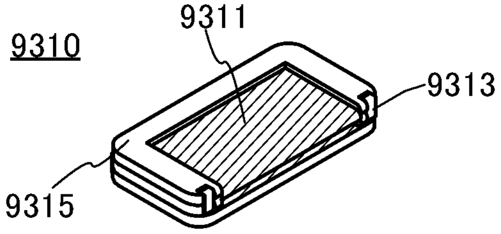

FIGS. 15A to 15C illustrate a foldable portable information terminal 9310. FIG. 15A illustrates the portable information terminal 9310 that is opened. FIG. 15B illustrates the portable information terminal 9310 that is being opened or being folded. FIG. 15C illustrates the portable information terminal 9310 that is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state.

The light-emitting apparatus of one embodiment of the present invention can be used for the display panel 9311.

Example 1

In this example, results of detailed examinations on driving voltages of light-emitting devices including low-refractive-index organic compounds and driving voltages of light-emitting devices including comparative materials will be described. Structural formulae of main organic compounds used in this example are shown below.

[Chemical formulae 10]

(i)

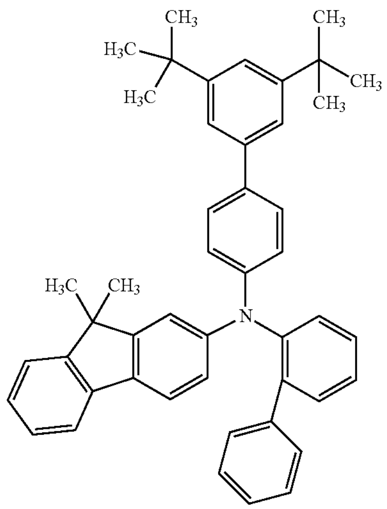

mmtBuBioFBi (ii)

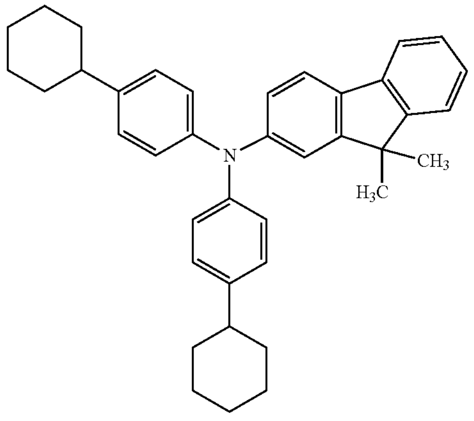

dchPAF

-continued
(iii)
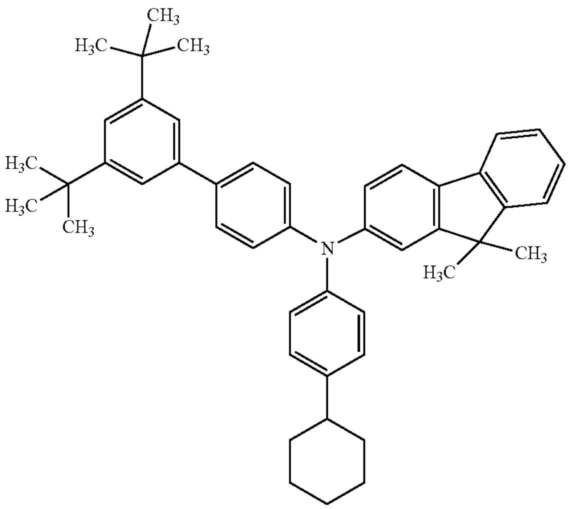
mmtBuBichPAF
(iv)
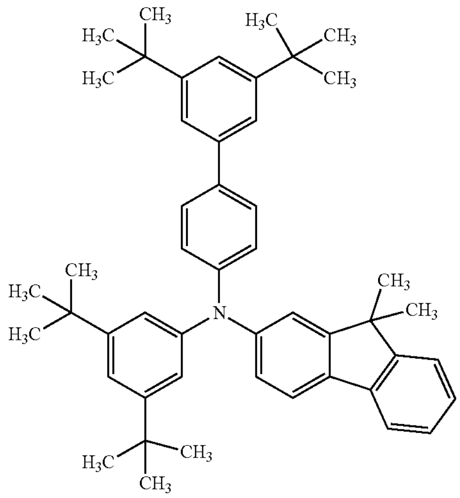
mmtBuBimmtBuPAF
(v)
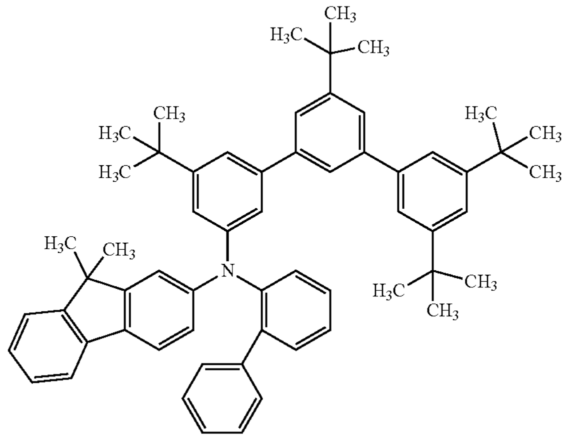
mmtBumTPoFBi-02
-continued
(vi)
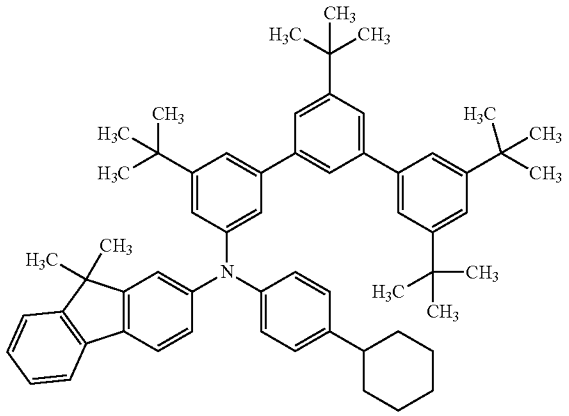
mmtBumTPChPAF-02
(vii)
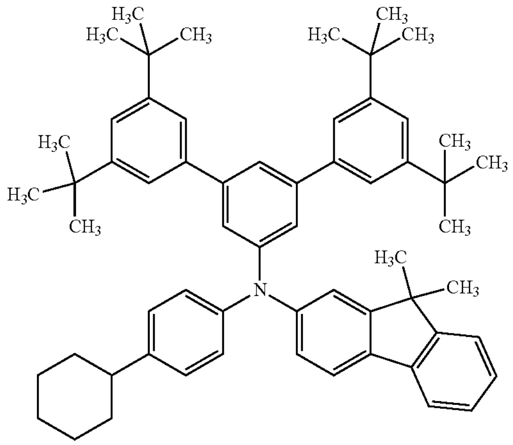
mmtBumTPChPAF

[Chemical formulae 11]
(viii)
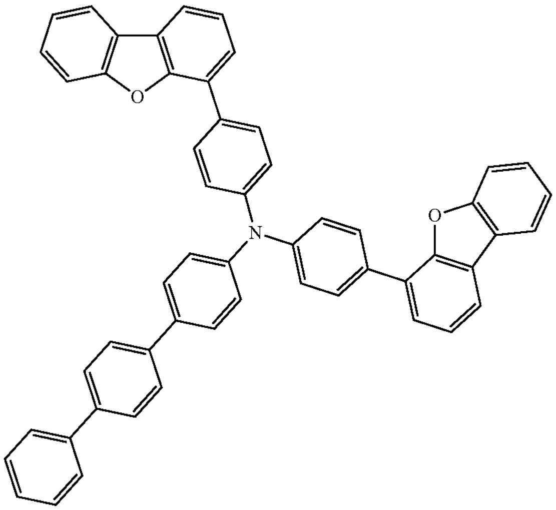
DBfBB1TP
(ix)
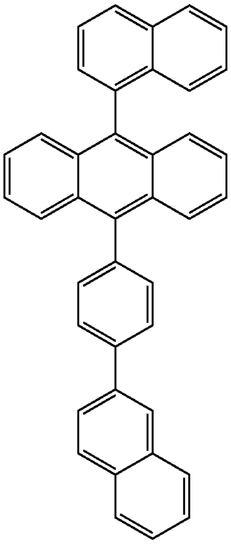
αN-βNPAnth
(x)
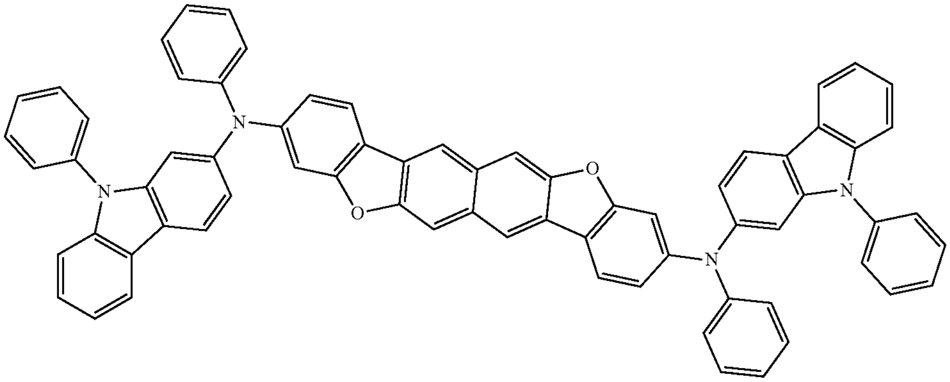
3,10PCA2Nbf(IV)-02
(xi)
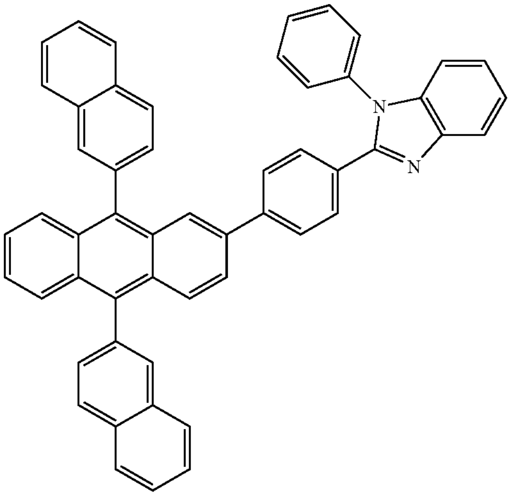
ZADN
(xii)
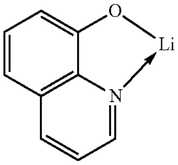
Liq -continued (xiii)

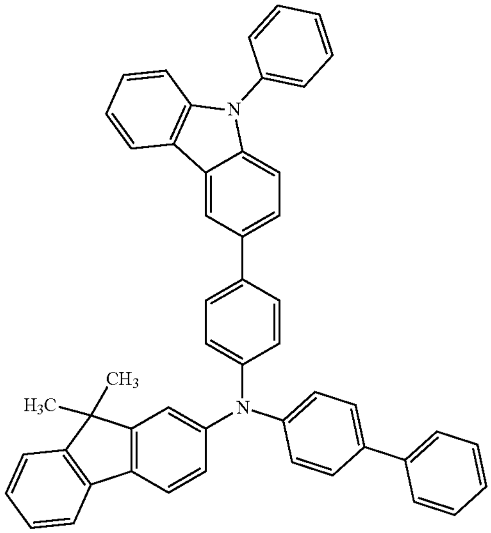

PCBBiF (Method for Fabricating Light-Emitting Devices 1 to 7)

First, indium tin oxide containing silicon oxide (ITSO) was deposited over a glass substrate by a sputtering method to form the first electrode 101. The thickness of the first electrode 101 was 55 nm and the electrode area was 2 mm×2 mm.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus so that a surface over which the first electrode 101 was formed faced downward. Then, a low-refractive-index organic compound (low-n HTM) and an electron acceptor material (OCHD-001) were deposited over the first electrode 101 to a thickness of 10 nm by co-evaporation using an evaporation method with resistance heating so that the weight ratio of the low-n HTM to the OCHD-001 was 1:0.1; thus, the hole-injection layer 111 was formed.

Note that as the low-n HTM material, the following are used in light-emitting devices: N-3',5'-ditertiarybutyl-1,1'-biphenyl-4-yl-N-1,1'-biphenyl-2-yl-9,9-dimethyl-9H-fluoren-2-amine (abbreviation: mmtBuBioFBi) represented by the structural formula (i) was used in a light-emitting device 1-1; N,N-bis(4-cyclohexylphenyl)-9,9-dimethyl-9H-fluoren-2-amine (abbreviation: dchPAF) represented by the structural formula (ii) was used in light-emitting devices 2-1 to 2-3; N-[(3',5'-ditertiarybutyl)-1,1'-biphenyl-4-yl]-N-(4-cyclohexylphenyl)-9,9-dimethyl-9H-fluoren-2-amine (abbreviation: mmtBuBichPAF) represented by the structural formula (iii) was used in light-emitting devices 3-1 and 3-2; N-(3,5-ditertiarybutylphenyl)-N-(3',5',-ditertiarybutyl-1,1'-biphenyl-4-yl)-9,9,-dimethyl-9H-fluoren-2-amine (abbreviation: mmtBuBimmtBuPAF) represented by the structural formula (iv) was used in a light-emitting device 4; N-(1,1'-biphenyl-2-yl)-N-(3,3",5',5"-tetra-tert-butyl-1,1':3',1"-terphenyl-5-yl)-9,9-dimethyl-9H-fluoren-2-amine (abbreviation: mmtBumTPoFBi-02) represented by the structural formula (v) was used in light-emitting devices 5-1 to 5-3; N-(4-cyclohexylphenyl)-N-(3,3",5',5"-tetra-tert-butyl-1,1':3',1"-terphenyl-5-yl)-9,9-dimethyl-9H-fluoren-2-amine (abbreviation: mmtBumTPChPAF-02) represented by the structural formula (vi) was used in light-emitting devices 6-1 to 6-3; and N-(3,3",5,5"-tetra-t-butyl-1,1':3',1"-terphenyl-5'-yl)-N-(4-cyclohexylphenyl)-9,9-dimethyl-9H-fluoren-2-amine (abbreviation: mmtBumTPchPAF) represented by the structural formula (vii) was used in light-emitting devices 7-1 to 7-4.

Note that light-emitting devices using the same low-n HTM are sometimes denoted by the same reference numeral: for example, the light-emitting devices 2-1 to 2-3 are sometimes collectively referred to as light-emitting devices 2.

Next, over the hole-injection layer 111, mmtBuBioFBi was deposited by evaporation in the light-emitting device 1-1, dchPAF was deposited by evaporation in the light-emitting devices 2-1 to 2-3, mmtBuBichPAF was deposited by evaporation in the light-emitting devices 3-1 and 3-2, mmtBuBimmtBuPAF was deposited by evaporation in the light-emitting device 4, mmtBumTPoFBi-02 was deposited by evaporation in the light-emitting devices 5-1 to 5-3, mmtBumTPChPAF-02 was deposited by evaporation in the light-emitting devices 6-1 to 6-3, and mmtBumTPchPAF was deposited by evaporation in the light-emitting devices 7-1 to 7-4 so that their thicknesses were each 30 nm. After that, N,N-bis[4-(dibenzofurane-4-yl)phenyl]-4-amino-p-terphenyl (abbreviation: DBfBB1TP) represented by the structural formula (viii) was deposited by evaporation to a thickness of 15 nm in the light-emitting device 1-1 and the light-emitting device 2-1 and to a thickness of 10 nm in the other light-emitting devices, whereby the hole-transport layer 112 was formed in each of the light-emitting devices.

Then, 9-(1-naphthyl)-10-[4-(2-naphthyl)phenyl]anthracene (abbreviation: αN-PNPAnth) represented by the structural formula (ix) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by the structural formula (x) were deposited by co-evaporation to a thickness of 25 nm such that the weight ratio of αN-βNPAnth to 3,10PCA2Nbf(IV)-02 was 1:0.015, whereby the light-emitting layer 113 was formed.

Then, 2-{4-[9,10-di(naphthalen-2-yl)-2-anthryl]phenyl}-1-phenyl-1H-benzimidazole (abbreviation: ZADN) represented by the structural formula (xi) and 8-quinolinolato-lithium (abbreviation: Liq) represented by the structural formula (xii) were deposited over the light-emitting layer 113 by co-evaporation to a thickness of 25 nm such that the weight ratio of ZADN to Liq was 1:1, whereby the electron-transport layer 114 was formed.

After the formation of the electron-transport layer 114, Liq was deposited by evaporation to a thickness of 1 nm to form the electron-injection layer 115, and then aluminum was deposited by evaporation to a thickness of 200 nm to form the second electrode 102. Thus, the light-emitting devices were fabricated.

(Method for Fabricating Comparative Light-Emitting Device 1)

A comparative light-emitting device 1 was fabricated in a manner similar to that for the light-emitting device 1-1 except that mmtBuBioFBi in the light-emitting device 1-1 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (xiii).

The structures of the light-emitting devices and the comparative light-emitting device 1 are listed in the following table.

The light-emitting devices and the comparative light-emitting device were sealed with a glass substrate in a glove box containing a nitrogen atmosphere so as not to be exposed to the air (a sealing material was applied to surround the devices and UV treatment and heat treatment at 80° C. for one hour were performed at the time of sealing).

Figure 16:
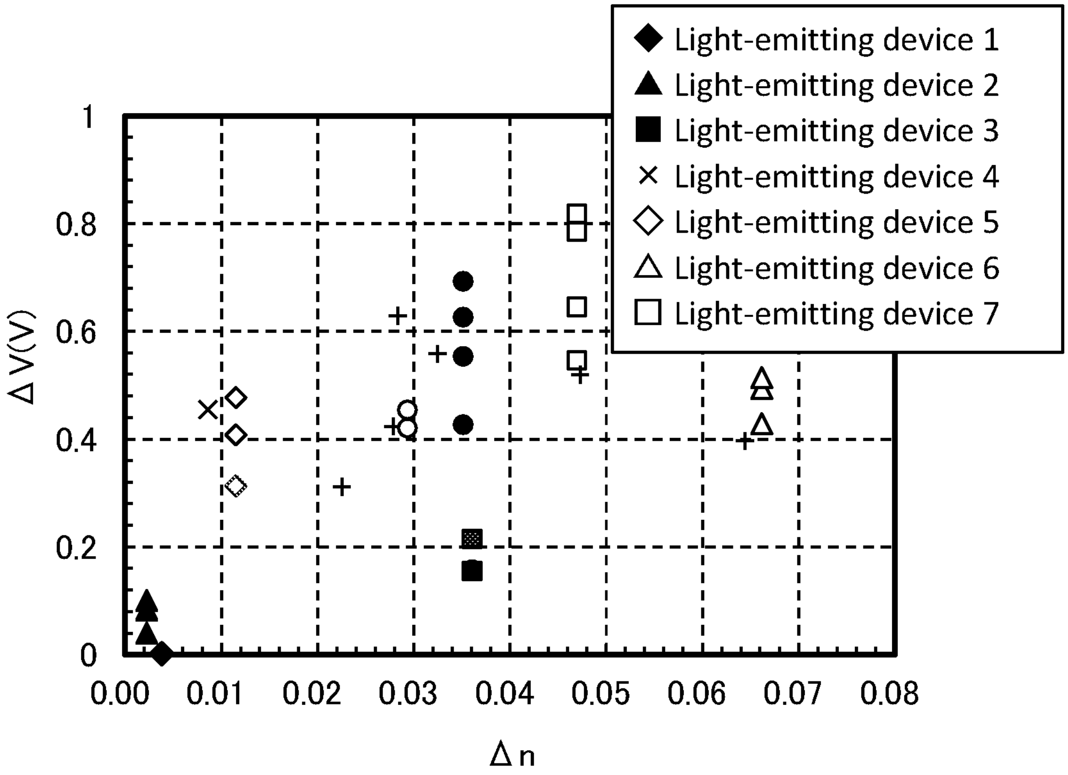
FIG. 16 is a graph showing a difference in driving voltage (ΔV) between a conventional light-emitting device and light-emitting devices 1 to 7, versus birefringence Δn of a deposited film of a low-refractive-index organic compound of each of the light-emitting devices 1 to 7.

FIG. 16 shows a graph in which the difference in driving voltage (ΔV) between each light-emitting device and the comparative light-emitting device when they were driven at 1 mA is plotted on the y-axis, and the birefringence Δn of the low-n HTM used in the light-emitting device with respect to light with a wavelength of 458 nm is plotted on the x-axis. Note that the plotted values denoted by "+" show results of light-emitting devices having the same structure as the light-emitting devices 1 to 7 and including a different low-n HTM, although details thereof are omitted.

FIG. 16 shows that the light-emitting devices 1 and 2, each of which includes the low-n HTM with birefringence Δn greater than or equal to 0 and less than or equal to 0.008, definitely have smaller ΔV and lower driving voltage than the other light-emitting devices.

Figure 17:
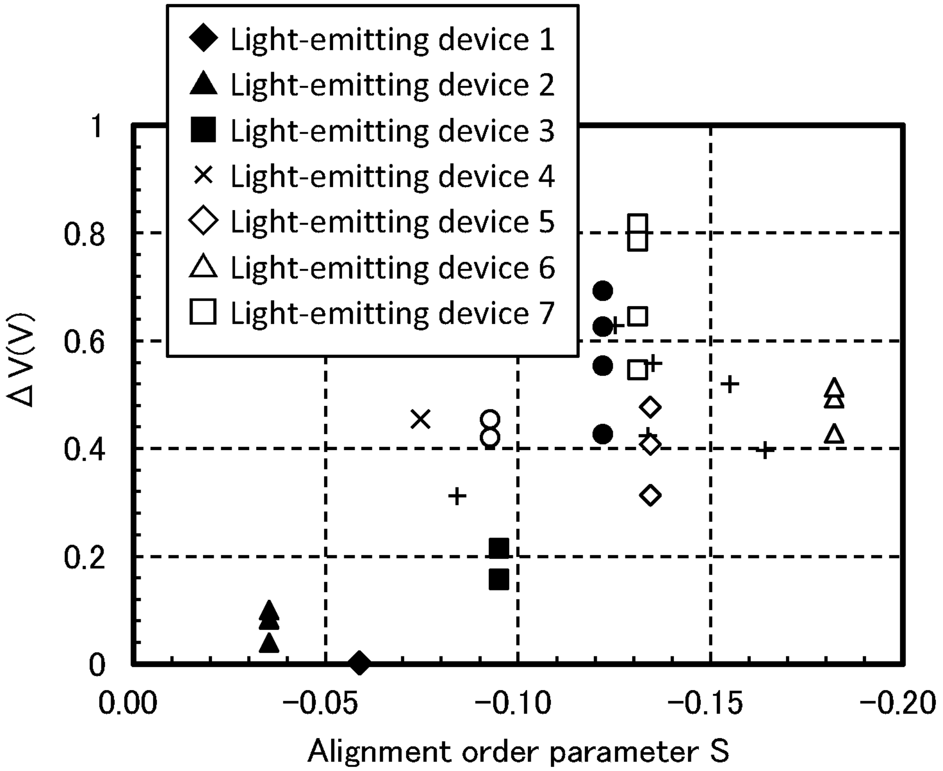
FIG. 17 is a graph showing a difference in driving voltage (ΔV) between a conventional light-emitting device and the light-emitting devices 1 to 7, versus an alignment order parameter S of the deposited film of the low-refractive-index organic compound of each of the light-emitting devices 1 to 7.

Similarly, FIG. 17 shows a graph in which the difference in driving voltage (ΔV) between each light-emitting device and the comparative light-emitting device when they were driven at 1 mA is plotted on the x-axis, and the alignment order parameter S of the deposited film of the low-n HTM used in the light-emitting device (the alignment order parameter with respect to light with a wavelength corresponding to the longest wavelength where an absorption peak appears in the absorption spectrum of the low-n HTM)

TABLE 1

| Hole-injection layer | Hole-transport layer | Electron-blocking layer | Light-emitting layer | Electron-transport layer | Electron-injection layer |
|---|---|---|---|---|---|
| 10 nm HTM: OCHD-001 (1:0.1) | 30 nm HTM | 10 nm*1 DBfBB1TP | 25 nm αN-BNP Anth: 3,10PCA2Nbf(IV)-02 (1:0.015) | 25 nm ZADN:Liq (1:1) | 1 nm Liq |

*1:15 nm only in the light-emitting devices 1-1 and 2-1

Note that the light-emitting devices 1 to 3 of the above light-emitting devices are the light-emitting devices of Example.

Figure 26:
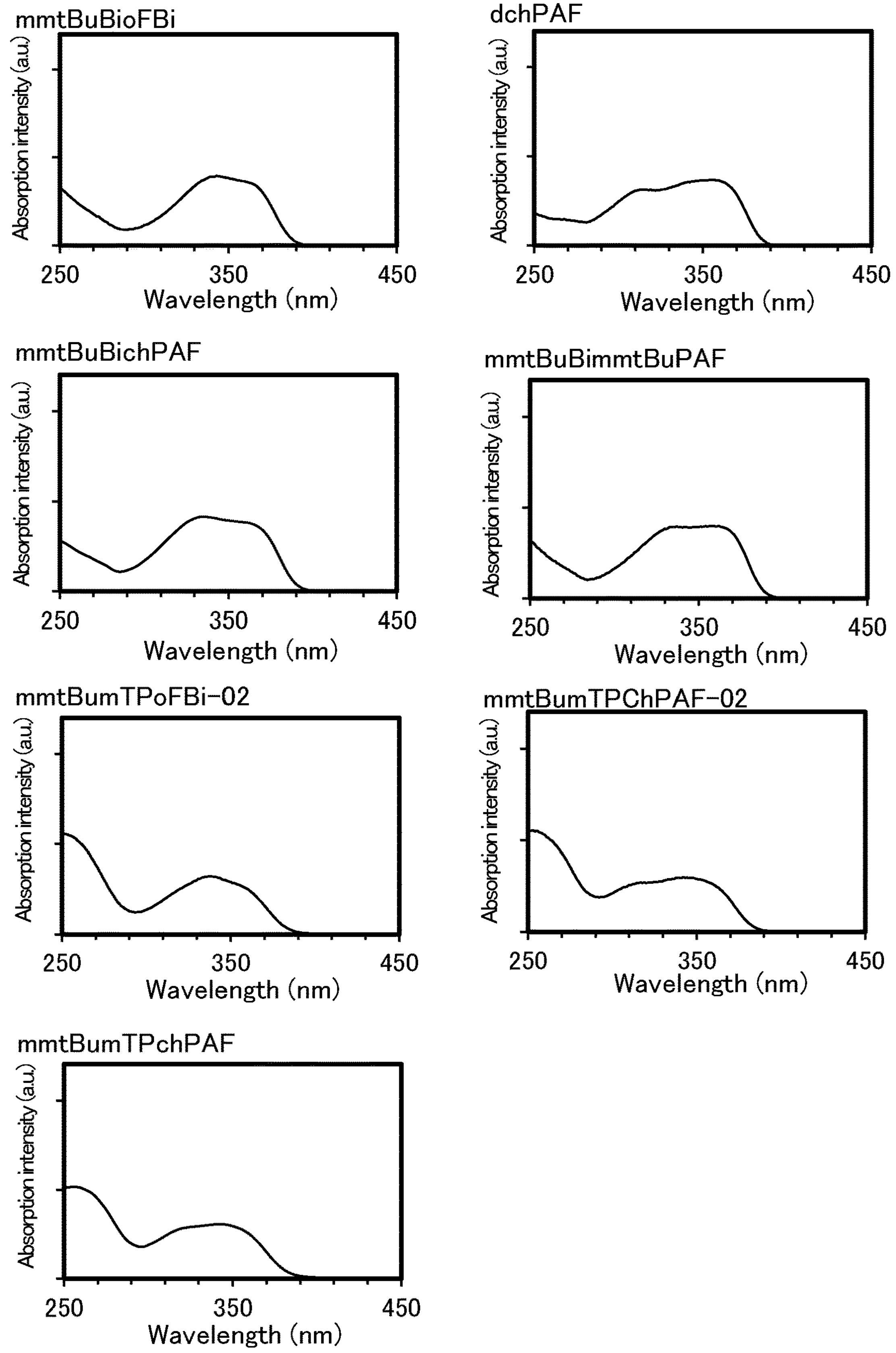
FIG. 26 shows absorption spectra of low-n HTMs that were used.

The following table shows the ordinary refractive indices $n_o$, the birefringence Δn, and the alignment order parameters S with respect to light with a wavelength of 458 nm, of the low-n HTMs and PCBBiF serving as a reference. The low-n HTMs and PCBBiF were used in the hole-injection layers and the hole-transport layers.

is plotted on the y-axis. In a manner similar to that in FIG. 16, the plotted values denoted by "+" show results of light-emitting devices having the same structure as the light-emitting devices 1 to 7 and including a different low-n HTM. Note that the absorption spectra of the low-n HTM deposited films are as shown in FIG. 26.

FIG. 17 shows that the light-emitting devices 1 and 2, each of which includes the low-n HTM that has an alignment order parameter S greater than or equal to −0.070 and less

TABLE 2

| | | HTM | Refractive index $n_o$ (@458 nm) | Birefringence Δn (@458 nm) | Alignment order parameter S |
|---|---|---|---|---|---|
| Light-emitting device | 1-1 | mmtBuBioFBi | 1.74 | 0.004 | −0.059 |
| | 2-1 to 2-3 | dchPAF | 1.71 | 0.002 | −0.035 |
| | 3-1 to 3-2 | mmtBuBichPAF | 1.72 | 0.036 | −0.095 |
| | 4 | mmtBuBimmtBuPAF | 1.68 | 0.009 | −0.075 |
| | 5-1 to 5-3 | mmtBumTPOFBi-02 | 1.70 | 0.012 | −0.134 |
| | 6-1 to 6-3 | mmtBumTPChPAF-02 | 1.67 | 0.066 | −0.182 |
| | 7-1 to 7-4 | mmtBumTPchPAF | 1.67 | 0.047 | −0.131 |
| Comparative light-emitting device 1 | | PCBBiF | 1.83 | 0.243 | −0.281 |

than or equal to 0.00 with respect to light with a wavelength corresponding to the longest wavelength where an absorption peak appears in the absorption spectrum when the low-n HTM is a deposited film, definitely have smaller ΔV and lower driving voltage than the other light-emitting devices The light-emitting device 3 has smaller ΔV than the other light-emitting devices including the low-n HTMs despite having high birefringence Δn, 0.036, and a low alignment order parameter S, −0.095. A para-biphenyl structure, in particular, a 1,1'-bephenyl-4-yl group, is directly bonded to nitrogen of amine in the low-n HTM used in the light-emitting device 3 as in the low-n HTM used in the light-emitting device 1, whereby the light-emitting device 3 has low driving voltage.

Note that the low-n HTM has a plurality of alkyl groups each having 3 to 8 carbon atoms and a plurality of cycloalkyl groups each having 6 to 12 carbon atoms to obtain a low refractive index. In the case where these groups are bonded to the 1,1'-bephenyl-4-yl group, it is preferable that these groups be bonded to any of 2'-, 3'-, 4'-, and 5'-positions, in particular, to the 3'- and 5'-positions, in which case the carrier-transport property of the low-n HTM is not inhibited and the driving voltage is reduced.

On the other hand, even when a 1,1'-bephenyl-4-yl group is directly bonded to nitrogen as in the case of the low-n HTM of the light-emitting device 4, the carrier-transport property is reduced to increase the driving voltage in the case where the alkyl group having 3 to 8 carbon atoms and the cycloalkyl group having 6 to 12 carbon atoms are each bonded at a meta-position of carbon serving as a start point, which is bonded to the nitrogen and included in a benzene ring in the nearest position to the nitrogen in an aryl group bonded to the nitrogen.

As described above, it is found that a light-emitting device including a low-n HTM can have low driving voltage when the birefringence Δn or the alignment order parameter S of the low-n HTM is within a certain range. It is also found that the use of a low-n HTM with a particular structure in a light-emitting device makes the light-emitting device have low driving voltage with the birefringence Δ or the alignment order parameter S being within a wider range than the above range.

Example 2

In this example, a light-emitting device including the organic compound of one embodiment of the present invention will be described in detail. Structural formulae of typical organic compounds used in this example are shown below.

[Chemical formulae 12]

(i)

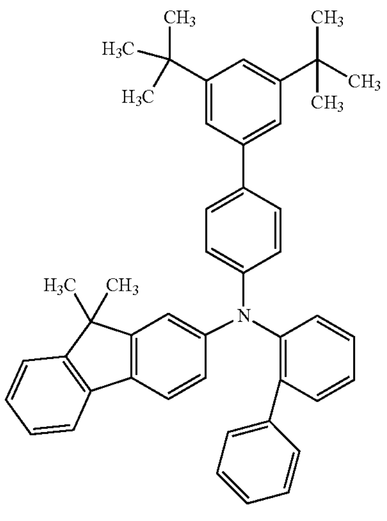

mmtBuBioFBi (viii)

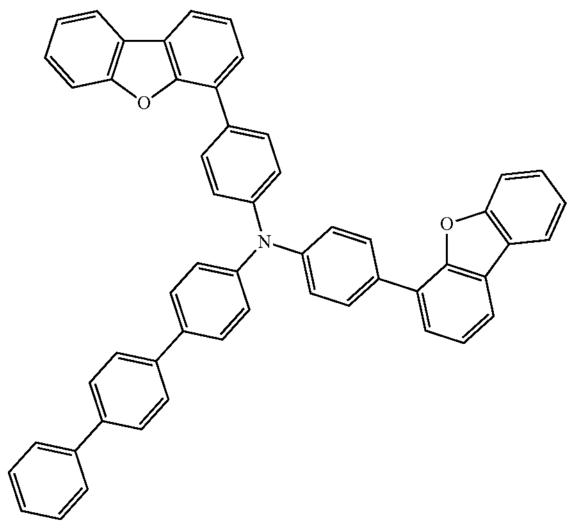

DBfBB1TP

-continued
(ix)
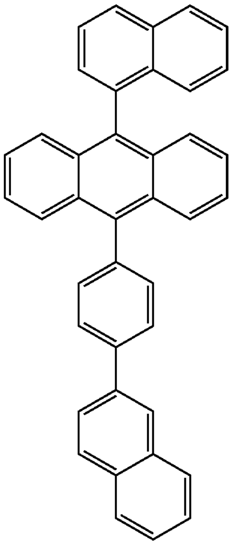
αN-βNPAnth
(xii)
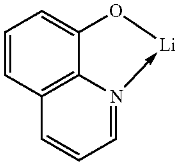
Liq
(x)
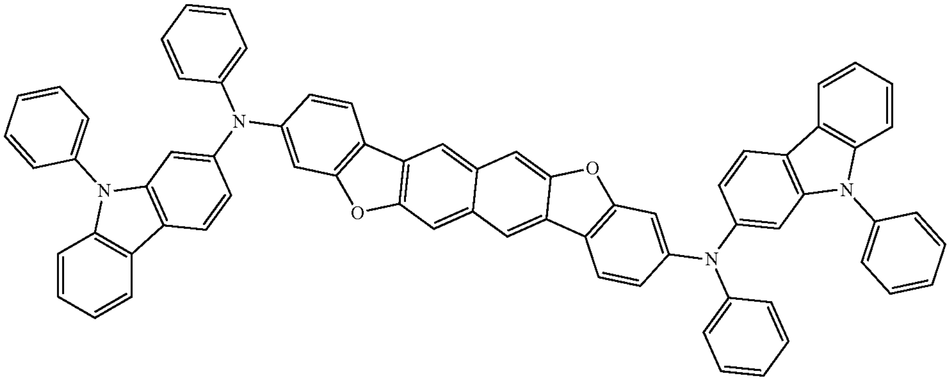
3,10PCA2Nbf(IV)-02
(xi)
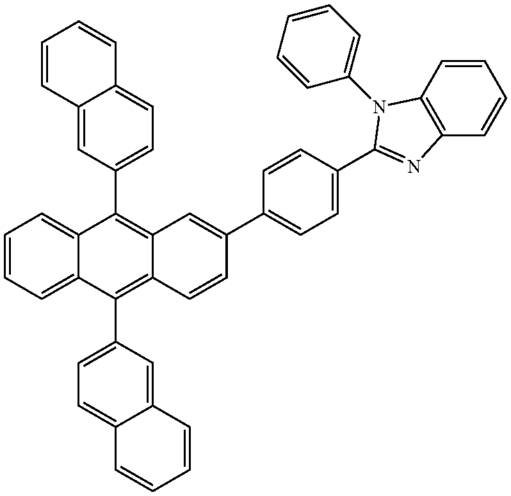
ZADN
(ii)
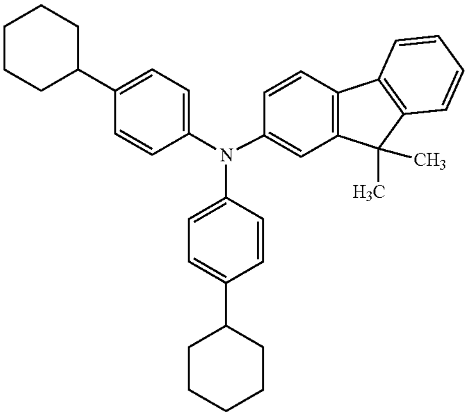
dchPAF -continued (iii)

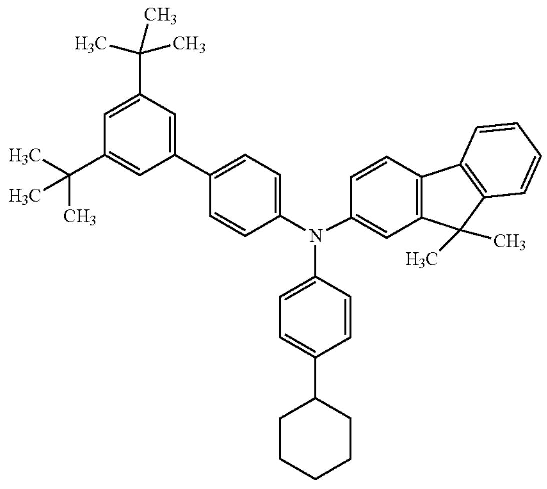

mmtBuBichPAF (xiii)

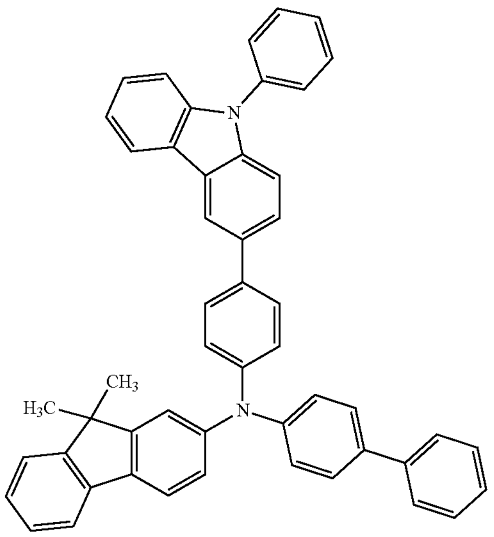

PCBBiF (Method for Fabricating Light-Emitting Devices 1-2, 2-4, and 3-3)

First, indium tin oxide containing silicon oxide (ITSO) was deposited over a glass substrate by a sputtering method to form the first electrode 101. The thickness of the first electrode 101 was 55 nm and the electrode area was 2 mm×2 mm.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus so that a surface over which the first electrode 101 was formed faced downward. Then, a low-refractive-index organic compound (low-n HTM) and an electron acceptor material (OCHD-001) were deposited over the first electrode 101 to a thickness of 10 nm by co-evaporation using an evaporation method with resistance heating so that the weight ratio of the low-n HTM to the OCHD-001 was 1:0.1; thus, the hole-injection layer 111 was formed.

Note that as the low-n HTM material, the following are used in light-emitting devices: N-3',5'-ditertiarybutyl-1,1'-biphenyl-4-yl-N-1,1'-biphenyl-2-yl-9,9-dimethyl-9H-fluoren-2-amine (abbreviation: mmtBuBioFBi) represented by the structural formula (i) was used in a light-emitting device 1-2; N,N-bis(4-cyclohexylphenyl)-9,9-dimethyl-9H-fluoren-2-amine (abbreviation: dchPAF) represented by the structural formula (ii) was used in a light-emitting device 2-4; and N-[(3',5'-ditertiarybutyl)-1,1'-biphenyl-4-yl]-N-(4-cyclohexylphenyl)-9,9-dimethyl-9H-fluoren-2-amine (abbreviation: mmtBuBichPAF) represented by the structural formula (iii) was used in a light-emitting device 3-3.

Next, over the hole-injection layer 111, mmtBuBioFBi was deposited by evaporation in the light-emitting device 1-2, dchPAF was deposited by evaporation in the light-emitting device 2-4, and mmtBuBichPAF was deposited by evaporation in the light-emitting devices 3-3 so that their thicknesses were each 30 nm. Then, N,N-bis[4-(dibenzofurane-4-yl)phenyl]-4-amino-p-terphenyl (abbreviation: DBfBB1TP) represented by the structural formula (viii) was deposited by evaporation to a thickness of 15 nm, whereby the hole-transport layer 112 was formed.

Then, 9-(1-naphthyl)-10-[4-(2-naphthyl)phenyl]anthracene (abbreviation: αN-PNPAnth) represented by the structural formula (ix) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by the structural formula (x) were deposited by co-evaporation to a thickness of 25 nm such that the weight ratio of αN-βNPAnth to 3,10PCA2Nbf(IV)-02 was 1:0.015, whereby the light-emitting layer 113 was formed.

Then, over the light-emitting layer 113, 2-{4-[9,10-di(naphthalen-2-yl)-2-anthryl]phenyl}-1-phenyl-TH-benzimidazole (abbreviation: ZADN) represented by the structural formula (xi) and 8-quinolinolato-lithium (abbreviation: Liq) represented by the structural formula (xii) were deposited by co-evaporation to a thickness of 25 nm such that the weight ratio of ZADN to Liq was 1:1, whereby the electron-transport layer 114 was formed.

After the formation of the electron-transport layer 114, Liq was deposited by evaporation to a thickness of 1 nm to form the electron-injection layer 115, and then, aluminum was deposited by evaporation to a thickness of 200 nm to form the second electrode 102. Thus, the light-emitting devices were fabricated.

(Method for Fabricating Comparative Light-Emitting Device 10)

A comparative light-emitting device 10 was fabricated in a manner similar to that for the light-emitting device 1-2 except that mmtBuBioFBi in the light-emitting device 1-2 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (xiii).

The structures of the light-emitting devices and the comparative light-emitting device are listed in the following table.

TABLE 3

| Hole-injection layer | Hole-transport layer | Electron-blocking layer | Light-emitting layer | Electron-transport layer | Electron-injection layer |
|---|---|---|---|---|---|
| 10 nm HTM: OCHD-001 (1:0.1) | 30 nm HTM | 15 nm DBfBB1TP | 25 nm αN-BNP Anth: 3,10PCA2Nbf(IV)-02 (1:0.015) | 25 nm ZADN:Liq (1:1) | 1 nm Liq |

TABLE 4

| | | HTM |
|---|---|---|
| Light-emitting device | 1-2 | mmtBuBioFBi |
| | 2-4 | dchPAF |
| | 3-3 | mmtBuBichPAF |
| Comparative light-emitting device 10 | | PCBBiF |

The following table shows the ordinary refractive indices $n_o$, the birefringence Δn, and the alignment order parameters S of the deposited films of the low-n HTMs and PCBBiF serving as a comparative material. The low-n HTMs and PCBBiF were used in the hole-injection layers and the hole-transport layers.

TABLE 5

| | | HTM | Refractive index $n_o$ (@458 nm) | Birefringence Δn (@458 nm) | Alignment order parameter S |
|---|---|---|---|---|---|
| Light-emitting device | 1-2 | mmtBuBioFBi | 1.74 | 0.004 | −0.059 |
| | 2-4 | dchPAF | 1.71 | 0.002 | −0.035 |
| | 3-3 | mmtBuBichPAF | 1.72 | 0.036 | −0.095 |
| Comparative light-emitting device 10 | | PCBBiF | 1.83 | 0.243 | −0.281 |

The light-emitting devices and the comparative light-emitting device 10 were sealed using a glass substrate in a glove box containing a nitrogen atmosphere so as not to be exposed to the air (a sealing material was applied to surround the devices and UV treatment and heat treatment at 80° C. for one hour were performed at the time of sealing). Then, the initial characteristics of the light-emitting devices were measured. Note that particular treatment for improving outcoupling efficiency was not performed on the glass substrate over which the light-emitting device was formed.

Figure 18:
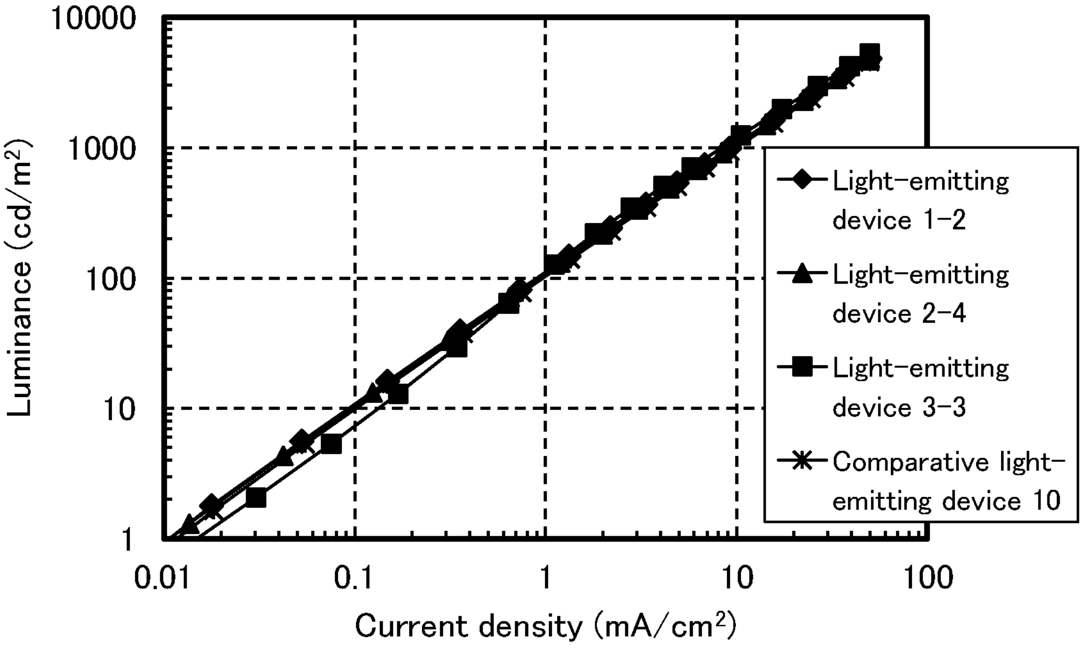
FIG. 18 shows the luminance-current density characteristics of light-emitting devices 1-2, 2-4, 3-3, and a comparative light-emitting device 10.
Figure 19:
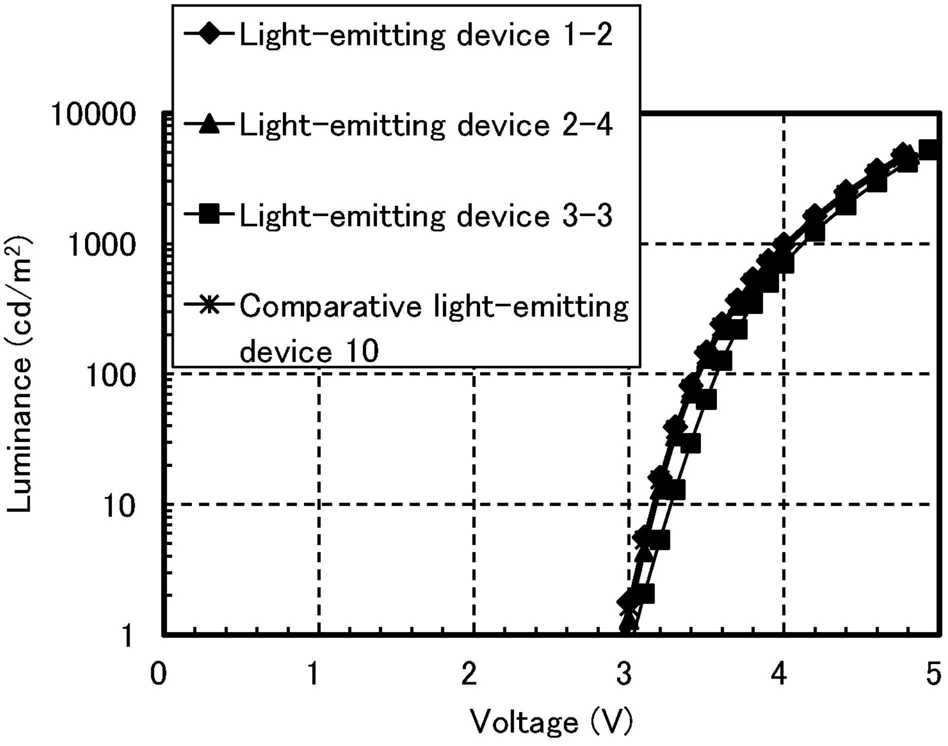
FIG. 19 shows the luminance-voltage characteristics of the light-emitting devices 1-2, 2-4, 3-3, and the comparative light-emitting device 10.
Figure 20:
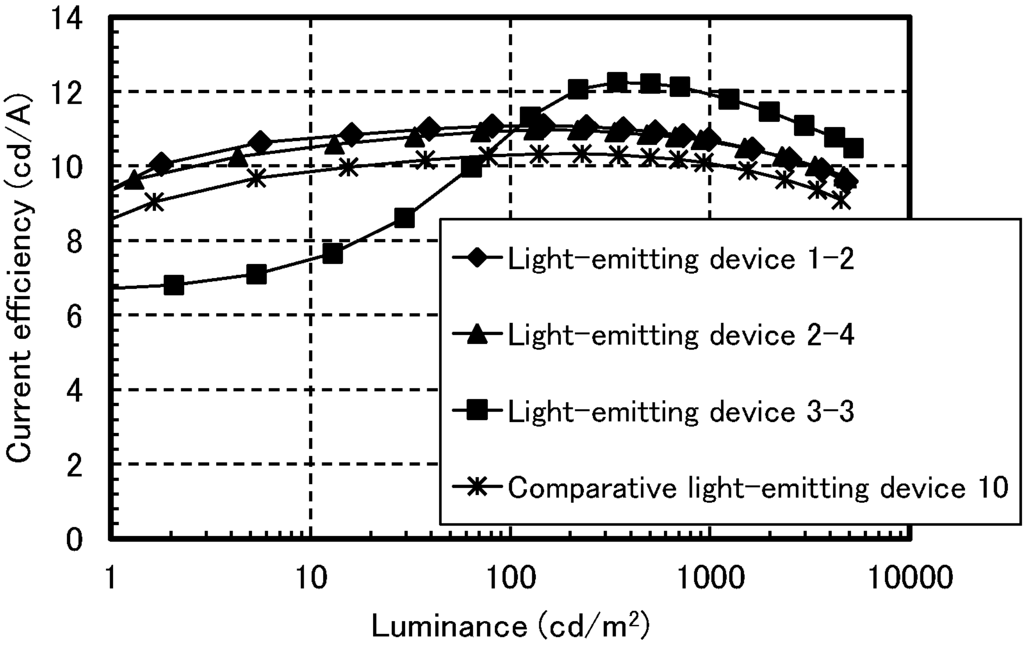
FIG. 20 shows the current efficiency-luminance characteristics of the light-emitting devices 1-2, 2-4, 3-3, and the comparative light-emitting device 10.
Figure 21:
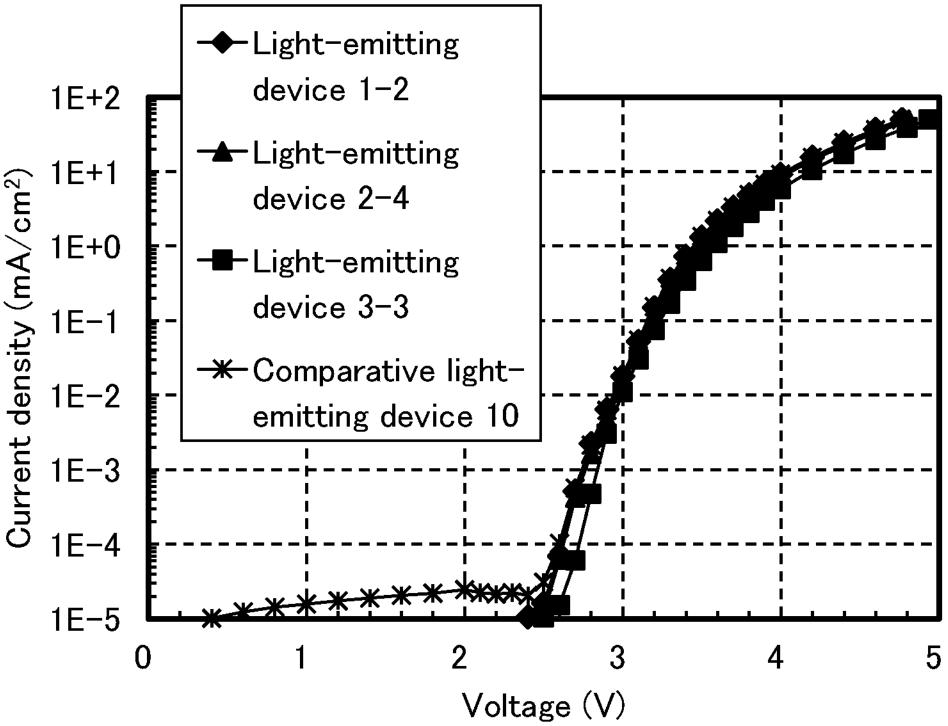
FIG. 21 shows the current density-voltage characteristics of the light-emitting devices 1-2, 2-4, 3-3, and the comparative light-emitting device 10.
Figure 22:
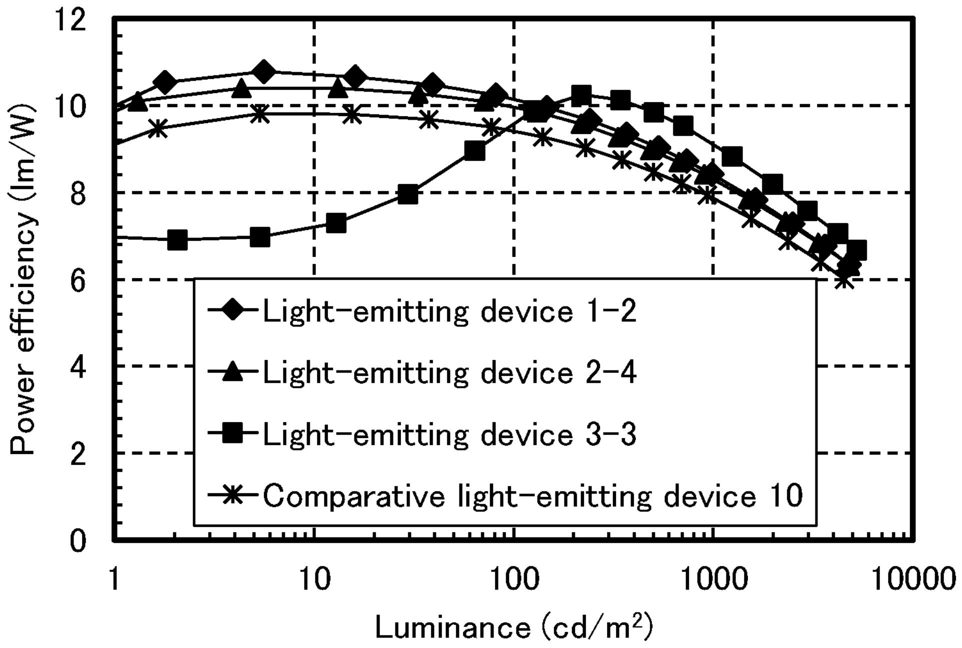
FIG. 22 shows the power efficiency-luminance characteristics of the light-emitting devices 1-2, 2-4, 3-3, and the comparative light-emitting device 10.
Figure 23:
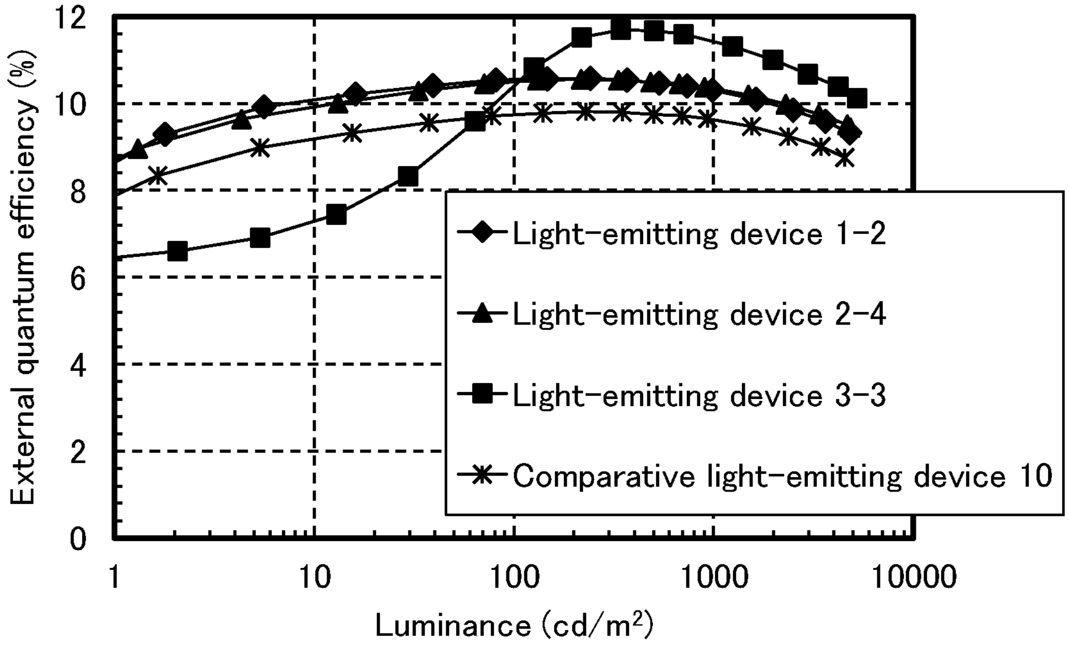
FIG. 23 shows the external quantum efficiency-luminance characteristics of the light-emitting devices 1-2, 2-4, 3-3, and the comparative light-emitting device 10.
Figure 24:
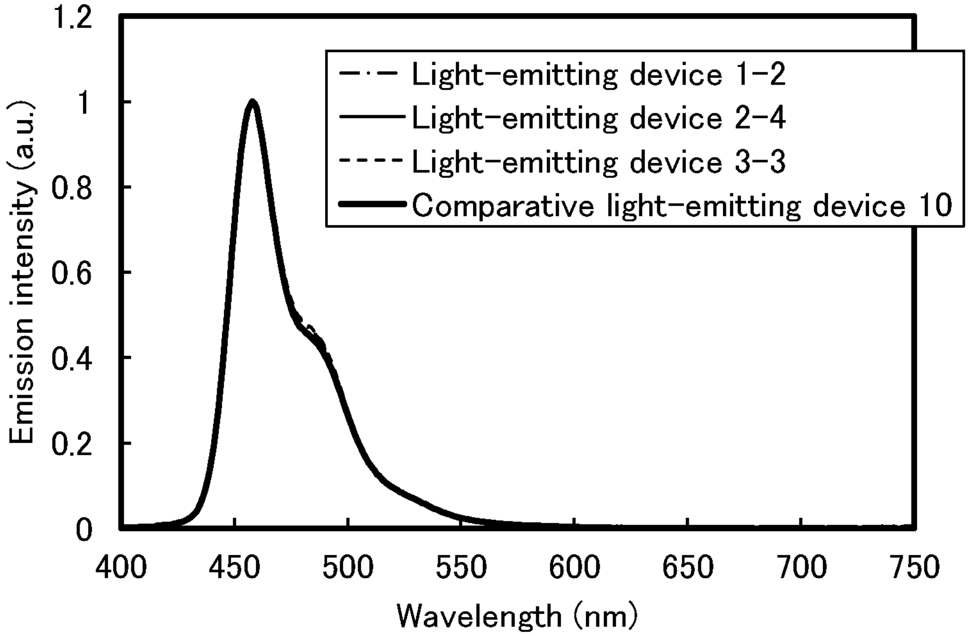
FIG. 24 shows the emission spectra of the light-emitting devices 1-2, 2-4, 3-3, and the comparative light-emitting device 10.

FIG. 18 shows the luminance-current density characteristics of the light-emitting devices 1-2, 2-4, and 3-3 and the comparative light-emitting device 10, FIG. 19 shows the luminance-voltage characteristics thereof, FIG. 20 shows the current efficiency-luminance characteristics thereof, FIG. 21 shows the current density-voltage characteristics thereof, FIG. 22 shows the power efficiency-luminance characteristics thereof, FIG. 23 shows the external quantum efficiency-luminance characteristics thereof, and FIG. 24 shows the emission spectra thereof. Table 6 shows the main characteristics of the light-emitting devices at a luminance about 1000 cd/$m^2$. Luminance, CIE chromaticity, and emission spectra were measured at normal temperature with a spectroradiometer (UR-UL1R produced by TOPCON TECHNOHOUSE CORPORATION). The external quantum efficiency was calculated from the measured luminance and emission spectra, on the assumption that the light-emitting devices had Lambertian light-distribution characteristics.

TABLE 6

| | Voltage (V) | Current (mA) | Current density (mA/$cm^2$) | Chromaticity x | Chromaticity y | Current efficiency (cd/A) | External quantum efficiency (%) |
|---|---|---|---|---|---|---|---|
| Light-emitting device 1-2 | 4.0 | 0.37 | 9.2 | 0.14 | 0.11 | 10.7 | 10.3 |
| Light-emitting device 2-4 | 4.0 | 0.34 | 8.4 | 0.14 | 0.11 | 10.7 | 10.4 |
| Light-emitting device 3-3 | 4.2 | 0.42 | 10.5 | 0.14 | 0.11 | 11.8 | 11.3 |
| Comparative light-emitting device 10 | 4.0 | 0.37 | 9.2 | 0.14 | 0.11 | 10.1 | 9.6 |

FIG. 18 to FIG. 24 show that the light-emitting devices of one embodiment of the present invention each have significantly high external quantum efficiency and favorable emission efficiency by including a low-refractive-index organic compound in the hole-injection layer and the hole-transport layer, while exhibiting driving voltage equivalent to that of the comparative light-emitting device 10. Accordingly, the light-emitting devices of one embodiment of the present invention are light-emitting devices with low power consumption.

Figure 25:
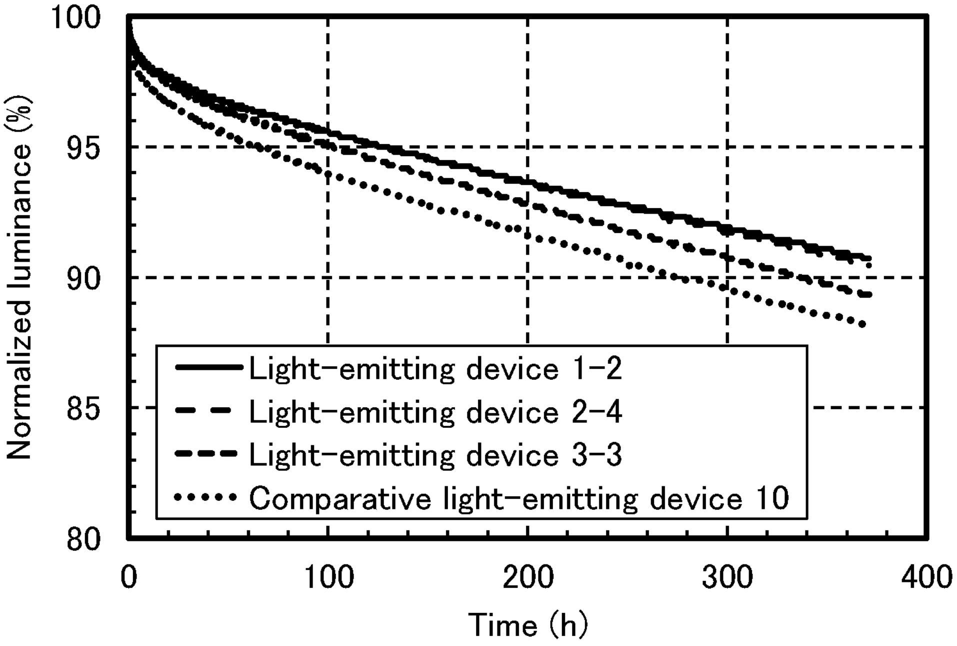
FIG. 25 is a graph showing a change in luminance over driving time of the light-emitting devices 1-2, 2-4, 3-3 and the comparative light-emitting device 10.

FIG. 25 is a graph showing a change in luminance over driving time of the light-emitting devices 1-2, 2-4, and 3-3 and the comparative light-emitting device 10 at a current density of 50 mA/$cm^2$. In addition, as shown in FIG. 25, the light-emitting devices 1-2, 2-4, and 3-3, each of which is the light-emitting device of one embodiment of the present invention, were found to have favorable lifetime.

Example 3

Synthesis Example 1

In this synthesis example, a method for synthesizing N-3',5'-ditertiarybutyl-1,1'-biphenyl-4-yl-N-1,1'-biphenyl-2-yl-9,9,-dimethyl-9H-fluoren-2-amine (abbreviation: mmtBuBioFBi), which is the organic compound of one embodiment of the present invention and was used in the above example, will be described. The structure of mmtBuBioFBi is shown below.

[Chemical formula 13]

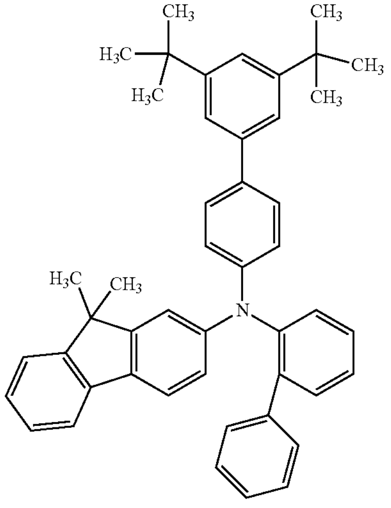

(mmtBuBioFBi)

Into a three-neck flask were put 2.22 g (7.4 mmol) of 4-chloro-3',5'-di-tert-butyl-1,1'-biphenyl, 2.94 g (8.1 mmol) of 2-(2-biphenylyl)amino-9,9-dimethylfluorene, 2.34 g (24.4 mmol) of sodium-tert-butoxide (abbreviation: tBuONa), and 37 mL of xylene. The mixture was degassed under reduced pressure, and then the air in the flask was replaced with nitrogen. To this mixture, 107.6 mg (0.31 mmol) of di-tert-butyl(1-methyl-2,2-diphenylcyclopropyl) phosphine (abbreviation: cBRIDP (registered trademark)) and 28.1 mg (0.077 mmol) of allylpalladium chloride dimer (abbreviation: [PdCl(allyl)]2) were added. This mixture was heated at 100° C. for approximately four hours. After that, the temperature of the flask was lowered to approximately 70° C., and approximately 4 mL of water was added to the mixture, so that a solid was precipitated. The precipitated solid was separated by filtration. The filtrate was concentrated, and the obtained solution was purified by silica gel column chromatography. The obtained solution was concentrated. After that, ethanol was added thereto and the obtained solution was concentrated again; this process was performed three times to obtain an ethanol suspension. After that, recrystallization was performed on the ethanol suspension. The precipitate was cooled to approximately −10° C. and then filtrated, and the obtained solid was dried at approximately 130° C. under reduced pressure, whereby 2.07 g of a target white solid was obtained in a yield of 45%. The synthesis scheme of this synthesis example is shown below.

[Chemical formula 14]

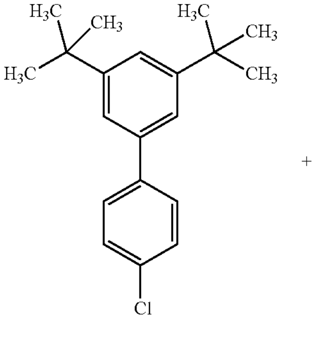

-continued

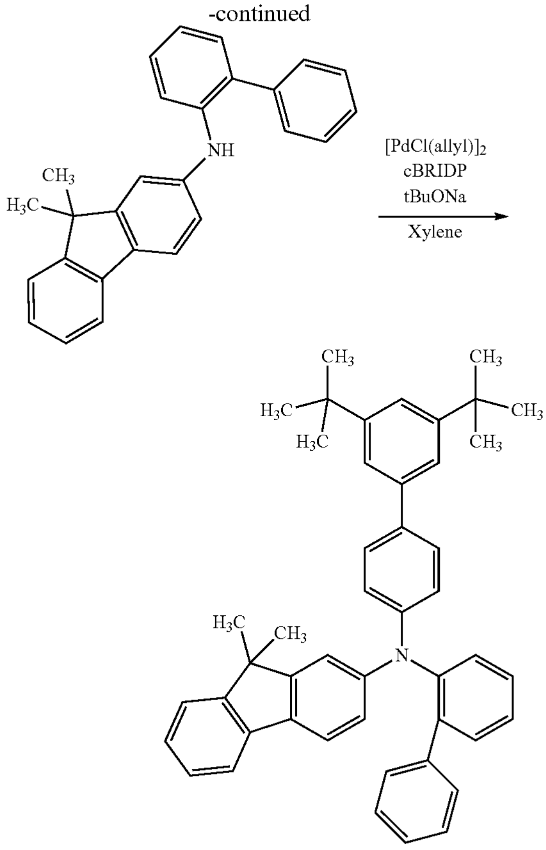

(mmtBuBioFBi)

Analysis results by nuclear magnetic resonance ($^1$H-NMR) spectroscopy of the white solid obtained in this synthesis example are shown below. The results show that mmtBuBioFBi was synthesized in this synthesis example.

$^1$H-NMR ($CDCl_3$, 500 MHz):δ=1.29 (s, 6H), 1.38 (s, 18H), 6.76 (dd, $J_1$=8.0 Hz, $J_2$=2.0 Hz, 1H), 6.87 (d, J=2.5 Hz, 1H), 7.00-7.08 (m, 5H), 7.18-7.23 (m, 3H), 7.27-7.43 (m, 12H), 7.55 (d, J=7.5 Hz, 1H).

Then, 2.0 g of the obtained solid was purified by a train sublimation method. The purification by sublimation was conducted by heating at 225° C. under a pressure of 3.77 Pa with an argon flow rate of 15.0 mL/min. After the purification by sublimation, 1.9 g of a white solid was obtained at a collection rate of 95%.

The refractive index of mmtBuBioFBi was measured by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method.

The results show that mmtBuBioFBi is a material with a low refractive index: the ordinary refractive index is within the range of 1.50 to 1.75 in the entire blue emission region (from 455 nm to 465 nm), and the ordinary refractive index at 633 nm is within the range of 1.45 to 1.70.

Next, the hole mobility of mmtBuBioFBi was calculated. The hole mobility was calculated by two kinds of methods: one is a method by calculation with simulation from the electrical characteristics of a measurement element in which only holes serve as carriers; the other is an impedance spectroscopy (IS) method.

In the IS method, a micro sinusoidal voltage signal ($V=V_0[\exp(j\omega t)]$) is applied to an EL device, and the impedance of the EL element ($Z=V/I$) is obtained from a phase difference between the current amplitude of a response current signal ($I=I_0\exp[j(\omega t+\phi)]$) and the input signal. By applying the voltage to the EL element while the frequency of the voltage is changed from a high level to a low level, components having various relaxation times that contribute to the impedance can be separated and measured.

Here, admittance Y (=1/Z), which is the reciprocal number of the impedance, can be represented by conductance G and susceptance B as shown in the following formula (1).

[Formula 1]

$$Y = \frac{1}{Z} = G + jB \tag{1}$$

In addition, by a single injection model, calculation of the following formulae (2) and (3) can be performed. Here, gin the formula (4) is differential conductance. In the formula, C represents capacitance, θ represents a transit angle (ωt), ω represents angular frequency, t represents transit time, and d represents a thickness. For the analysis, the current equation, the Poisson equation and the current continuity equation are used and a diffusion current and a trap state are ignored.

[Formula 2]

$$G = \frac{g\theta^3}{6}\frac{\theta - \sin\theta}{(\theta - \sin\theta)^2 + \left(\frac{\theta^2}{2} + \cos\theta - 1\right)^2} \tag{2}$$

$$B = \omega C = \frac{g\theta^3}{6}\frac{\frac{\theta^2}{2} + \cos\theta - 1}{(\theta - \sin\theta)^2 + \left(\frac{\theta^2}{2} + \cos\theta - 1\right)^2} \tag{3}$$

$$g = \frac{9}{4}\varepsilon\mu\frac{V_0}{d^3} \tag{4}$$

A method for calculating mobility from the frequency characteristics of capacitance is a −ΔB method. A method for calculating mobility from the frequency characteristics of conductance is a ωΔG method.

In practice, first, a measurement element is fabricated using a material whose carrier mobility is intended to be calculated. The measurement element of this example is designed such that only holes flow therein as carriers. In this specification, a method for calculating mobility from the frequency characteristics of capacitance (the −ΔB method) is described.

The structure of the measurement element is shown in the following table. Note that in the table, APC is an alloy film of silver (Ag), palladium (Pd), and copper (Cu), ITSO is an indium tin oxide containing silicon oxide, OCHD-001 is an electron acceptor material, $MoO_x$ is a molybdenum oxide, and Al is aluminum. The mobility of a material used for a second layer formed to a thickness of 500 nm can be calculated.

TABLE 7

| Anode | | First layer | Second layer | Third layer | Cathode |
|---|---|---|---|---|---|
| 100 nm | 50 nm | 5 nm | 500 nm | 5 nm | 100 nm |
| APC | ITSO | mmtBuBioFBi: OCHD-001 (1:0.1) | mmtBuBioFBi | mmtBuBioFBi: $MoO_x$ (1:1) | Al |

Figure 27:
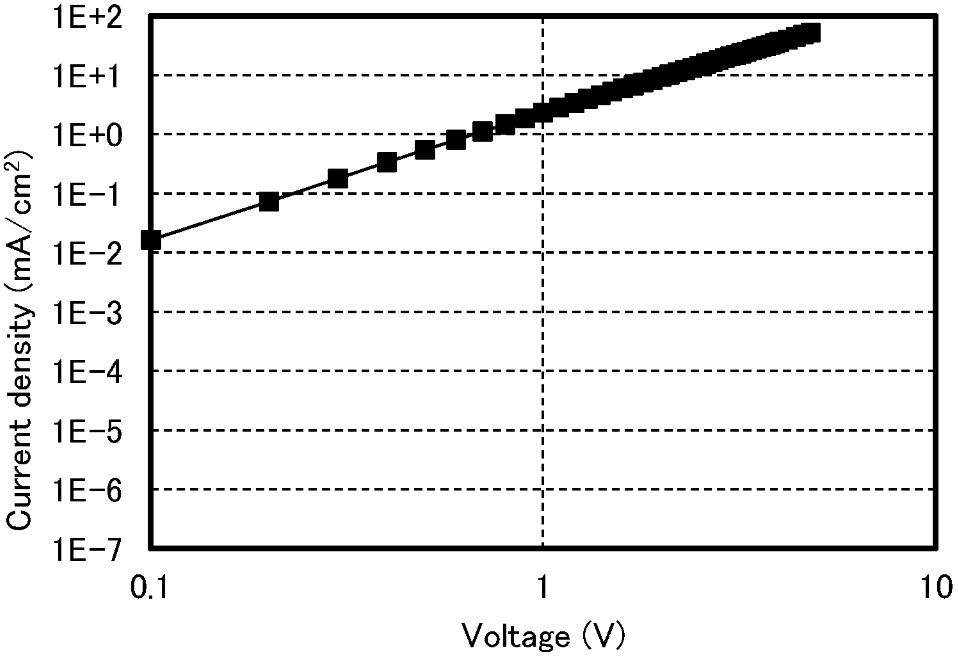
FIG. 27 shows the current density-voltage characteristics of a measurement element that includes mmtBuBioFBi and whose carriers are holes only.

FIG. 27 shows the current density-voltage characteristics of the measurement element.

The impedance was measured under the conditions where the frequency was 1 Hz to 3 MHz, the AC voltage was 70 mV, and the DC voltage was applied in the range of 5.0 V to 9.0 V. Here, capacitance is calculated from admittance, which is the reciprocal number of the obtained impedance (the above formula (1)).

The frequency characteristics of the capacitance C are obtained from a phase difference in current, which is generated because a space charge generated by carriers injected by the micro voltage signal cannot completely follow the micro AC voltage. The transit time of the injected carriers in the film is defined by time T until the carriers reach a counter electrode, and is represented by the following formula (5). Note that L represents a thickness.

[Formula 3]

$$T = \frac{4}{3}\frac{L^2}{\mu V_0} \tag{5}$$

A negative susceptance change (−ΔB) corresponds to a value (−ωΔC) obtained by multiplying a capacitance change −ΔC by angular frequency ω. According to the formula (3), there is a relation between peak frequency on the lowest frequency side $f'_{max}$ ($=\omega_{max}/2\pi$) and the transit time T as shown in the following formula (6).

[Formula 4]

$$T = \frac{4.5}{2\pi f'_{max}} \tag{6}$$

The transit time T can be obtained from the peak frequency on the lowest frequency side $f'_{max}$ obtained from the frequency characteristics of −ΔB calculated from the above measurement (i.e., at a DC voltage of 7.0 V) (see the above formula (6)); therefore, the hole mobility at a voltage of 7.0 V in this case can be calculated from the above formula (5). Through the same measurement with the DC voltage in the range of 5.0 V to 9.0 V, the hole mobility at each voltage (electric field strength) can be calculated, so that the electric field strength dependence of the mobility can also be measured.

Figure 28:
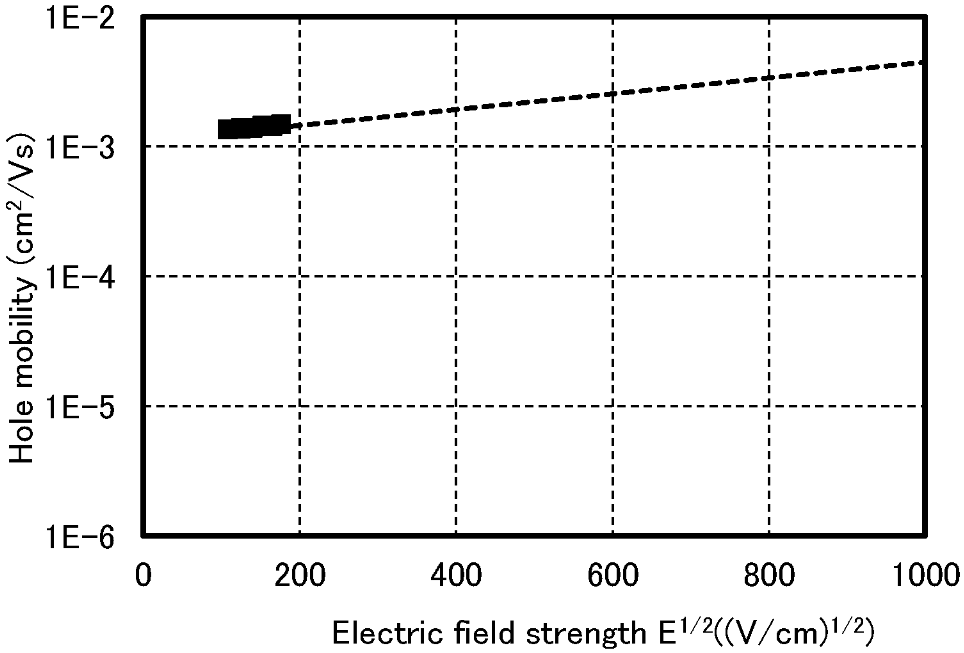
FIG. 28 shows hole mobility of mmtBuBioFBi.

FIG. 28 shows the electric field strength dependence of the hole mobility of mmtBuBioFBi, which was obtained from the above calculation method. Note that hole mobility calculated by simulation is shown together by a dotted line. Note that the horizontal axis in FIG. 28 represents the one-half power of electric field strength calculated from voltage.

For the simulation, Setfos (drift-diffusion module produced by CYBERNET SYSTEMS Co., Ltd.) was used. The simulation parameters are as follows: the work function of ITSO serving as the anode was 5.36 eV, the work function of Al serving as the cathode was 4.2 eV, and the HOMO level of mmtBuBioFBi was −5.42 eV. The charge density of the second layer was $1.0\times10^{18}$ $cm^{-3}$.

The work functions of the electrodes were measured by photoelectron spectroscopy using "AC-2" produced by Riken Keiki Co., Ltd. in the air.

The HOMO level of the organic compound was measured by cyclic voltammetry (CV) measurement. Note that for the measurement, an electrochemical analyzer (ALS 600A or 600C, produced by BAS Inc.) was used, and the measurement was performed on a solution obtained by dissolving each compound in N,N-dimethylformamide (abbreviation: DMF). In the measurement, the potential of a working electrode with respect to a reference electrode was changed within an appropriate range, so that the oxidation peak potential and the reduction peak potential were obtained. In addition, the HOMO level of the compound was obtained from the estimated redox potential of the reference electrode of −4.94 eV and the obtained peak potential.

Thus, mmtBuBioFBi has hole mobility higher than or equal to $1\times10^{-3}$ $cm^2/Vs$, showing that mmtBuBioFBi is an organic compound having high hole mobility and excellent characteristics.

Example 4

Synthesis Example 2

In this synthesis example, a method for synthesizing N,N-bis(4-cyclohexylphenyl)-9,9,-dimethyl-9H-fluoren-2-amine (abbreviation: dchPAF), which is the organic compound of the one embodiment of the present invention and used in the example, will be described. The structure of dchPAF is shown below.

[Chemical formula 15]

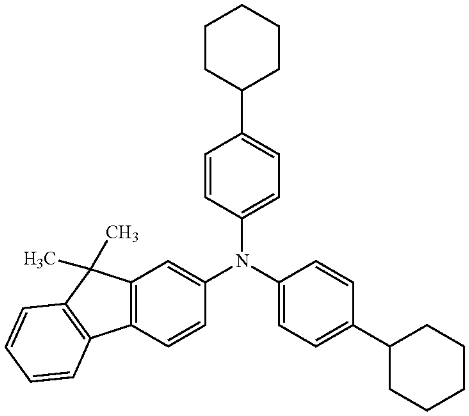

(dchPAF)

Step 1: Synthesis of N,N-bis(4-cyclohexylphenyl)-9,9,-dimethyl-9H-fluoren-2-amine (Abbreviation: dchPAF)

In a three-neck flask were put 10.6 g (51 mmol) of 9,9-dimethyl-9H-fluoren-2-amine, 18.2 g (76 mmol) of 4-cyclohexyl-1-bromobenzene, 21.9 g (228 mmol) of sodium-tert-butoxide, and 255 mL of xylene. The mixture was degassed under reduced pressure, and then the air in the flask was replaced with nitrogen. The mixture was stirred while being heated to approximately 50° C. Then, 370 mg (1.0 mmol) of allylpalladium(II) chloride dimer (abbreviation: $[(Allyl)PdCl]_2$) and 1660 mg (4.0 mmol) of di-tert-butyl(1-methyl-2,2-diphenylcyclopropyl)phosphine (abbreviation: cBRIDP (registered trademark)) were added, and the mixture was heated at 120° C. for approximately five hours. After that, the temperature of the flask was lowered to approximately 60° C., and approximately 4 mL of water was added to the mixture, so that a solid was precipitated. The precipitated solid was separated by filtration. The filtrate was concentrated, and the obtained solution was purified by silica gel column chromatography. The obtained solution was concentrated to give a condensed toluene solution. The toluene solution was dropped into ethanol for reprecipitation. The precipitate was collected by filtration at approximately 10° C. and the obtained solid was dried at approximately 80° C. under reduced pressure, whereby 10.1 g of a target white solid was obtained in a yield of 40%. The synthesis scheme of Step 1 is shown below.

[Chemical formula 16]

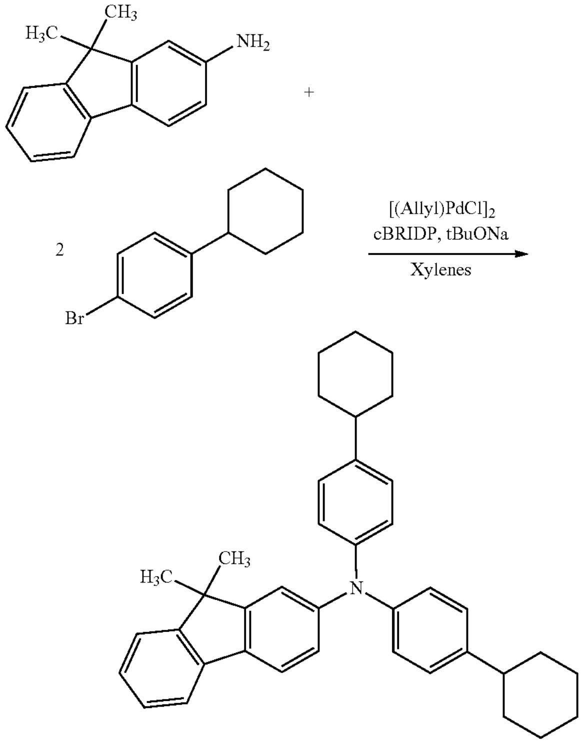

(dchPAF)

Analysis results by nuclear magnetic resonance ($^1H$-NMR) spectroscopy of the white solid obtained in Step 1 are shown below. The results show that dchPAF was synthesized in this synthesis example.

$^1H$-NMR. δ ($CDCl_3$): 7.60 (d, 1H, J=7.5 Hz), 7.53 (d, 1H, J=8.0 Hz), 7.37 (d, 2H, J=7.5 Hz), 7.29 (td, 1H, J=7.5 Hz, 1.0 Hz), 7.23 (td, 1H, J=7.5 Hz, 1.0 Hz), 7.19 (d, 1H, J=1.5 Hz), 7.06 (m, 8H), 6.97 (dd, 1H, J=8.0 Hz, 1.5 Hz), 2.41-2.51 (brm, 2H), 1.79-1.95 (m, 8H), 1.70-1.77 (m, 2H), 1.33-1.45 (brm, 14H), 1.19-1.30 (brm, 2H).

Then, 5.6 g of the obtained solid was purified by a train sublimation method. The purification by sublimation was conducted by heating at 215° C. under a pressure of 3.0 Pa with the argon flow rate of 12.0 mL/min. After the purification by sublimation, 5.2 g of a pale yellowish white solid was obtained at a collection rate of 94%.

The refractive index of dchPAF was measured by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method.

The results show that dchPAF is a material with a low refractive index: the ordinary refractive index is within the range of 1.50 to 1.75 in the entire blue emission region (from 455 nm to 465 nm), and the ordinary refractive index at 633 nm is within the range of 1.45 to 1.70.

Example 5

Synthesis Example 3

In this synthesis example, a method for synthesizing N-[(3',5'-ditertiarybutyl)-1,1'-biphenyl-4-yl]-N-(4-cyclohexylphenyl)-9,9-dimethyl-9H-fluoren-2-amine (abbreviation: mmtBuBichPAF), which is the organic compound of one embodiment of the present invention and used in the example, will be described. The structure of mmtBuBichPAF is shown below.

[Chemical formula 17]

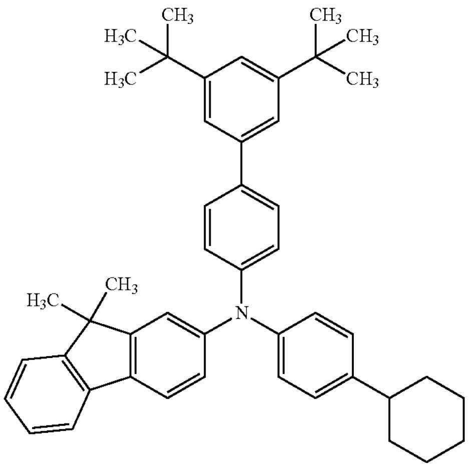

(mmtBuBichPAF)

Step 1: Synthesis of 3',5'-ditertiarybutyl-4-chloro-1,1'-biphenyl

In a three-neck flask were put 13.5 g (50 mmol) of 3,5-ditertiarybutyl-1-bromobenzene, 8.2 g (52.5 mmol) of 4-chlorophenylboronic acid, 21.8 g (158 mmol) of potassium carbonate, 125 mL of toluene, 31 mL of ethanol, and 40 mL of water. The mixture was degassed under reduced pressure, and then the air in the flask was replaced with nitrogen. To this mixture, 225 mg (1.0 mmol) of palladium acetate and 680 mg (2.0 mmol) of tris(2,6-methylphenyl) phosphine (abbreviation: $P(o\text{-}Tol)_3$) were added, and the mixture was heated and refluxed at 80° C. for approximately three hours. After that, the temperature of the flask was lowered to room temperature, and the mixture was separated into an organic layer and an aqueous layer. Magnesium sulfate was added to this solution for drying to be concentrated. The obtained solution was purified by silica gel column chromatography. The obtained solution was concentrated and dried for hardening. After that, hexane was added for recrystallization. The mixed solution in which a white solid was precipitated was cooled with ice and filtrated. The obtained solid was dried at approximately 60° C. in a vacuum, whereby 9.5 g of a target white solid was obtained in a yield of 63%. The synthesis scheme of Step 1 is shown below.

[Chemical formula 18]

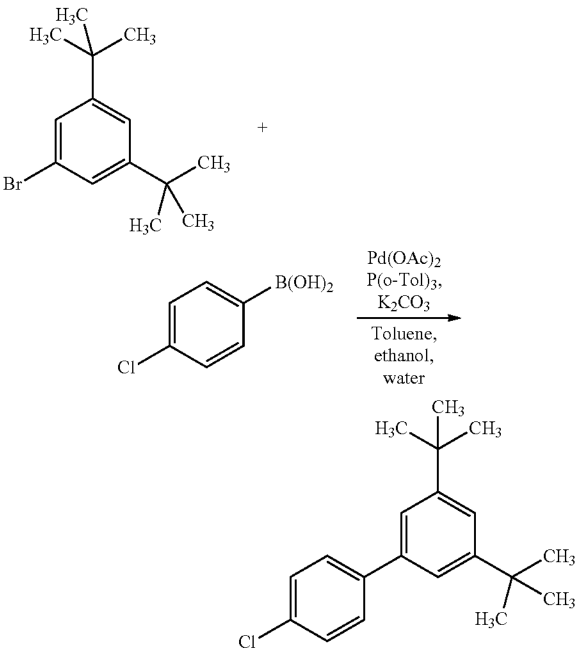

Step 2: Synthesis of N-(4-cyclohexylphenyl)-N-(9,9-dimethyl-9H-fluoren-2yl)amine In a three-neck flask were put 10.5 g (50 mmol) of 9,9-dimethyl-9H-fluoren-2-amine, 12.0 g (50 mmol) of 4-cyclohexyl-1-bromobenzene, 14.4 g (150 mmol) of sodium-tert-butoxide, and 250 mL of xylene. The mixture was degassed under reduced pressure, and then the air in the flask was replaced with nitrogen. The mixture was stirred while being heated to approximately 50° C. Then, 183 mg (0.50 mmol) of allylpalladium(II) chloride dimer (abbreviation: $[(Allyl)PdCl]_2$) and 821 mg (2.0 mmol) of di-tert-butyl (1-methyl-2,2-diphenylcyclopropyl)phosphine (abbreviation: cBRIDP (registered trademark)) were added, and the mixture was heated at 90° C. for approximately six hours. After that, the temperature of the flask was lowered to approximately 60° C., approximately 4 mL of water was added to the mixture, and a precipitated solid was separated by filtration. The filtrate was concentrated, and the obtained solution was purified by silica gel column chromatography. The obtained solution was concentrated to give a condensed toluene solution. This toluene solution was dried at approximately 60° C. in a vacuum, whereby a 17.3 g of a target brown oily substance was obtained in a yield of 92%. The synthesis scheme of Step 2 is shown below.

[Chemical formula 19]

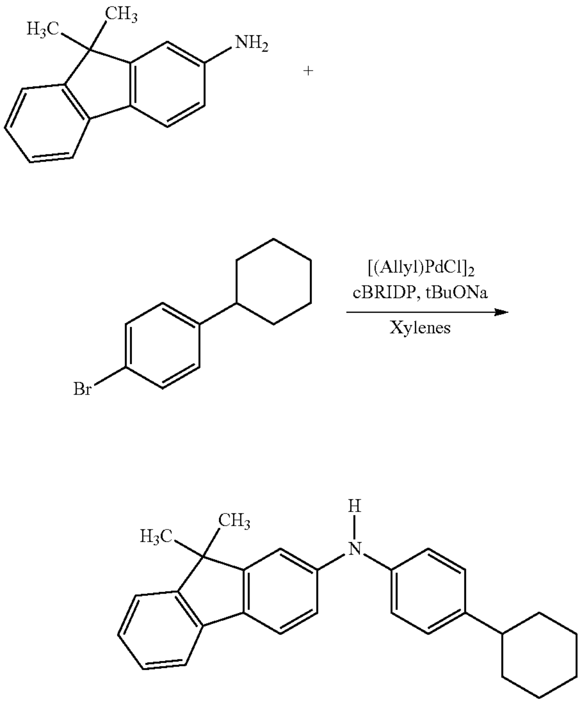

Step 3: Synthesis of N-[(3',5'-ditertiarybutyl)-1,1'-biphenyl-4-yl]-N-(4-cyclohexylphenyl)-9,9-dimethyl-9H-fluoren-2-amine (Abbreviation: mmtBuBichPAF)

In a three-neck flask were put 3.2 g (10.6 mmol) of 3',5'-ditertiarybutyl-4-chloro-1,1'-biphenyl obtained in Step 1, 3.9 g (10.6 mmol) of N-(4-cyclohexylphenyl)-N-(9,9-dimethyl-9H-fluoren-2yl)amine obtained in Step 2, 3.1 g (31.8 mmol) of sodium-tert-butoxide, and 53 mL of xylene. The mixture was degassed under reduced pressure, and then the air in the flask was replaced with nitrogen. The mixture was stirred while being heated to approximately 50° C. Then, 39 mg (0.11 mmol) of allylpalladium(II) chloride dimer (abbreviation: $[(Allyl)PdCl]_2$) and 150 mg (0.42 mmol) of di-tert-butyl(1-methyl-2,2-diphenylcyclopropyl) phosphine (abbreviation: cBRIDP (registered trademark)) were added, and this mixture was heated at 120° C. for approximately three hours. After that, the temperature of the flask was lowered to approximately 60° C., and approximately 1 mL of water was added to the mixture, so that a solid was precipitated. The precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitated solid was filtrated at approximately 20° C., and the obtained solid was dried at approximately 80° C. under reduced pressure, whereby 5.8 g of a target white solid was obtained in a yield of 87%. The synthesis scheme of Step 3 is shown below.

[Chemical formula 20]

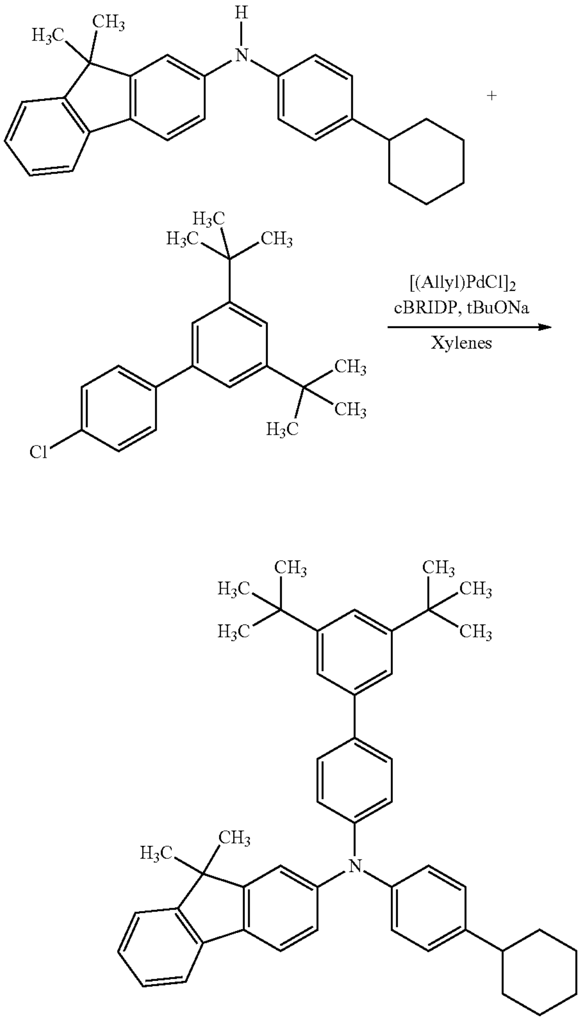

(mmtBuBichPAF)

Analysis results by nuclear magnetic resonance ($^1$H-NMR) spectroscopy of the white solid obtained in Step 3 are shown below. The results show that N-[(3',5'-ditertiarybutyl)-1,1'-biphenyl-4-yl]-N-(4-cyclohexylphenyl)-9,9-dimethyl-9H-fluoren-2-amine (abbreviation: mmtBuBichPAF) was synthesized in this synthesis example.

$^1$H-NMR. δ ($CDCl_3$): 7.63 (d, 1H, J=7.5 Hz), 7.57 (d, 1H, J=8.0 Hz), 7.44-7.49 (m, 2H), 7.37-7.42 (m, 4H), 7.31 (td, 1H, J=7.5 Hz, 2.0 Hz), 7.23-7.27 (m, 2H), 7.15-7.19 (m, 2H), 7.08-7.14 (m, 4H), 7.05 (dd, 1H, J=8.0 Hz, 2.0 Hz), 2.43-2.53 (brm, 1H), 1.81-1.96 (m, 4H), 1.75 (d, 1H, J=12.5 Hz), 1.32-1.48 (m, 28H), 1.20-1.31 (brm, 1H).

Next, 3.5 g of the obtained solid was purified by a train sublimation method. The purification by sublimation was conducted by heating at 255° C. under a pressure of 3.0 Pa with the argon flow rate of 11.8 mL/min. After the purification by sublimation, 3.1 g of a pale yellowish white solid was obtained at a collection rate of 89%.

The refractive index of mmtBuBichPAF was measured by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method.

The results show that mmtBuBichPAF is a material with a low refractive index: the ordinary refractive index is within the range of 1.50 to 1.75 in the entire blue emission region (from 455 nm to 465 nm), and the ordinary refractive index at 633 nm is within the range of 1.45 to 1.70.

Example 6

In this example, a light-emitting device including the organic compound of one embodiment of the present invention will be described in detail. Structural formulae of typical organic compounds used in this example are shown below.

[Chemical formulae 21]

(i)

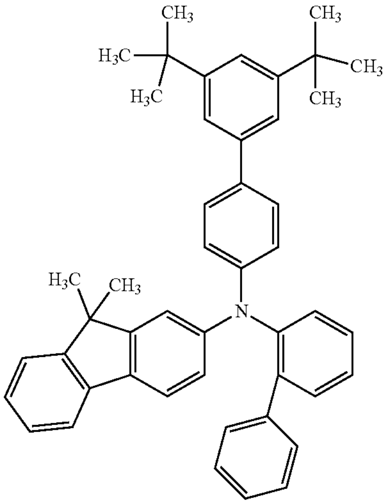

mmtBuBioFBi (xiv)

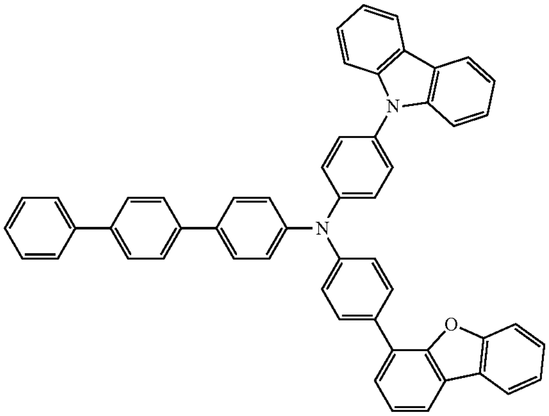

YGTPDBfB (x)

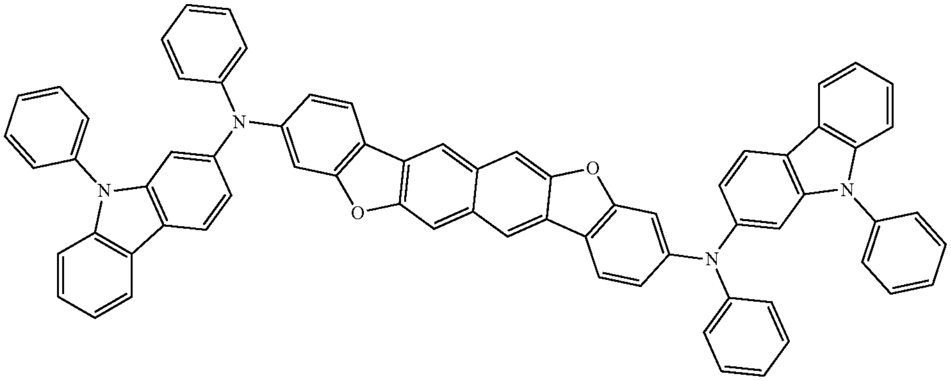

3,10PCA2Nbf(IV)-02

-continued
(xv)
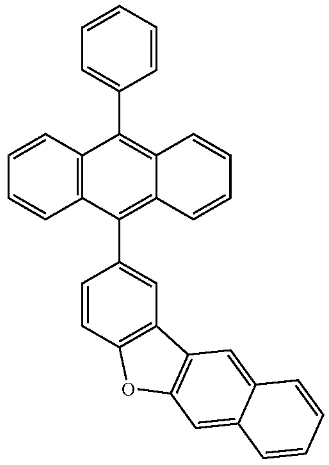
Bnf(II)PhA
(xvi)
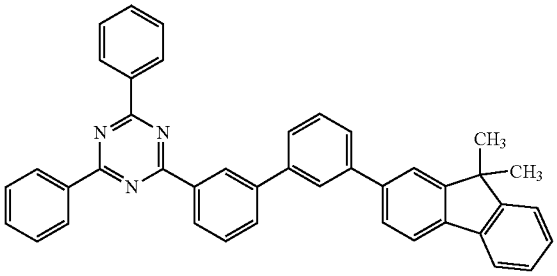
mFBPTzn
(xvii)
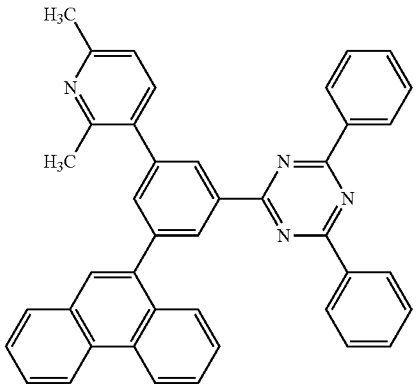
mPn-mDMePyPTzn
(xii)
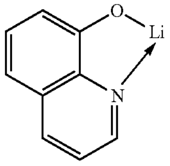
Liq
(xiii)
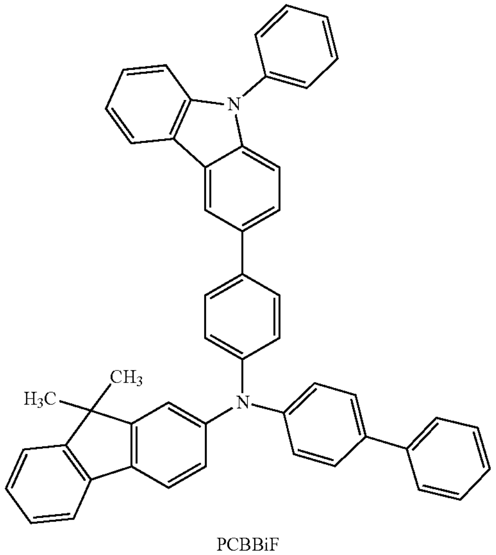
PCBBiF
(xviii)
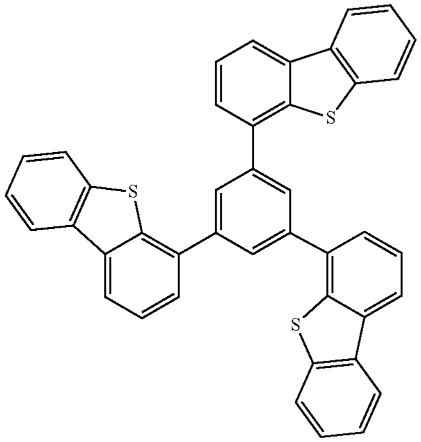
DBT3P-11

(Method for Fabricating Light-Emitting Device 20)

First, silver (Ag) was deposited over a glass substrate to a thickness of 100 nm to form a reflective electrode. After that, indium tin oxide containing silicon oxide (ITSO) was deposited by a sputtering method to form the first electrode 101. The thickness of the first electrode 101 was 10 nm and the electrode area was 2 mm×2 mm.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus so that a surface over which the first electrode 101 was formed faced downward. Then, a low-refractive-index organic compound (low-n HTM) and an electron acceptor material (OCHD-001) were deposited over the first electrode 101 to a thickness of 10 nm by co-evaporation using an evaporation method with resistance heating so that the weight ratio of the low-n HTM to the OCHD-001 was 1:0.1; thus, the hole-injection layer 111 was formed.

Note that N-3',5'-ditertiarybutyl-1,1'-biphenyl-4-yl-N-1,1'-biphenyl-2-yl-9,9,-dimethyl-9H-fluoren-2-amine (abbreviation: mmtBuBioFBi) represented by the structural formula (i) was used as the low-n HTM.

Next, mmtBuBioFBi was deposited over the hole-injection layer 111 by evaporation to a thickness of 120 nm to form the hole-transport layer 112. Then, N-[4-(9H-carbazol-9-yl)phenyl]-N-[4-(4-dibenzofuranyl)phenyl]-[1,1':4',1"-terphenyl]-4-amine (abbreviation: YGTPDBfB) represented by the structural formula (xiv) was deposited by evaporation to a thickness of 10 nm, whereby an electron-blocking layer was formed.

Subsequently, 2-(10-phenyl-9-anthracenyl)-benzo[b]naphtho[2,3-d]furan (abbreviation: Bnf(II)PhA) represented by the structural formula (xv) and 3,10-bis[N-(9-phenyl-9H-carbazol-2-yl)-N-phenylamino]naphtho[2,3-b;6,7-b']bis-benzofuran (abbreviation: 3,10PCA2Nbf(IV)-02) represented by the structural formula (x) were deposited by co-evaporation to a thickness of 25 nm such that the weight ratio of Bnf(II)PhA to 3,10PCA2Nbf(IV)-02 was 1:0.015, whereby the light-emitting layer 113 was formed.

After that, 2-[3'-(9,9-dimethyl-9H-fluoren-2-yl)-1,1'-biphenyl-3-yl]-4,6-diphenyl-1,3,5-triazine (abbreviation: mFBPTzn) represented by the structural formula (xvi) was deposited over the light-emitting layer 113 by evaporation to a thickness of 10 nm, whereby a hole-blocking layer was formed.

Then, 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by the structural formula (xvii) and 8-quinolinolato-lithium (abbreviation: Liq) represented by the structural formula (xii) were deposited over the hole-blocking layer by co-evaporation to a thickness of 25 nm so that the weight ratio of mPn-mDMePyPTzn to Liq was 1:1; thus, the electron-transport layer 114 was formed.

After the formation of the electron-transport layer 114, lithium fluoride (LiF) was deposited by evaporation to a thickness of 1 nm to form the electron-injection layer 115. Then, silver (Ag) and magnesium (Mg) were deposited by co-evaporation to a thickness of 15 nm so that the weight ratio of Ag to Mg was 10:1; thus, the second electrode 102 is formed. In that manner, a light-emitting device 20 was fabricated. Note that the second electrode 102 has a light-transmitting property, and the light-emitting device 20 is a top-emission light-emitting device in which emitted light is extracted from the second electrode side. Over the second electrode 102, 4,4',4"-(benzene-1,3,5-triyl)tri(dibenzothiophene) (abbreviation: DBT3P-II) represented by the structure formula (xviii) was deposited by evaporation to a thickness of 70 nm to improve outcoupling efficiency.

(Method for Fabricating Comparative Light-Emitting Device 20)

A comparative light-emitting device 20 was fabricated in a manner similar to that for the light-emitting device 20 except that mmtBuBioFBi in the light-emitting device 20 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (xiii).

The structures of the light-emitting device 20 and the comparative light-emitting device 20 are listed in the following tables.

TABLE 8

| Hole-injection layer | Hole-transport layer | Electron-blocking layer | Light-emitting layer | Hole-blocking layer | Electron-transport layer | Electron-injection layer |
|---|---|---|---|---|---|---|
| 10 nm HTM: OCHD-001 (1:0.1) | *2 HTM | 10 nm YGTPDBfB | 25 nm Bnf(II)PhA: 3,10PCA2Nbf(IV)-02 (1:0.015) | 10 nm mFBPTzn | 20 nm mPn-mDMePyPTzn: Liq (1:1) | 1 nm LiF |

*2 Light-emitting device 20: 120 nm, Comparative light-emitting device 20: 100 nm

TABLE 9

| | HTM |
|---|---|
| Light-emitting device 20 | mmtBuBioFBi |
| Comparative light-emitting device 20 | PCBBiF |

The following table shows the ordinary refractive indices $n_o$, the birefringence Δn, and the alignment order parameters S of the deposited films of the low-n HTM and PCBBiF serving as a comparative material. The low-n HTM and PCBBiF were used in the hole-injection layers and the hole-transport layers.

TABLE 10

| | HTM | Refractive index $n_o$ (@458 nm) | Birefringence $\Delta n$ (@458 nm) | Alignment order parameter S |
|---|---|---|---|---|
| Light-emitting device 20 | mmtBuBioFBi | 1.74 | 0.004 | −0.059 |
| Comparative light-emitting device 20 | PCBBiF | 1.83 | 0.243 | −0.281 |

The light-emitting device and the comparative light-emitting device were sealed using a glass substrate in a glove box containing a nitrogen atmosphere so as not to be exposed to the air (a sealing material was applied to surround the devices and UV treatment and heat treatment at 80° C. for 1 hour were performed at the time of sealing). Then, the initial characteristics of the light-emitting devices were measured.

Figure 29:
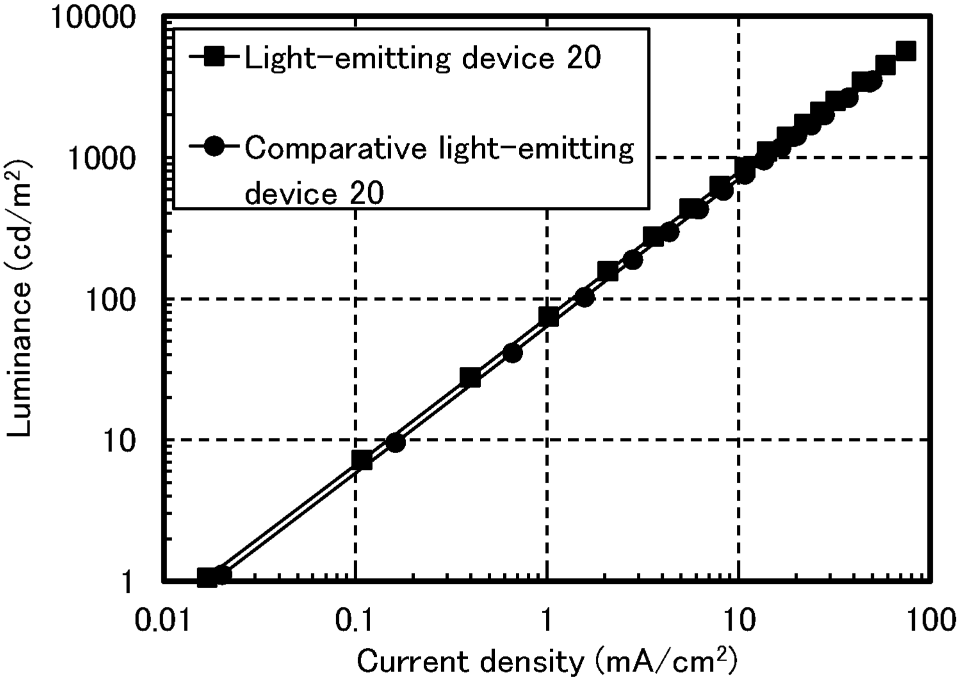
FIG. 29 shows the luminance-current density characteristics of a light-emitting device 20 and a comparative light-emitting device 20.
Figure 30:
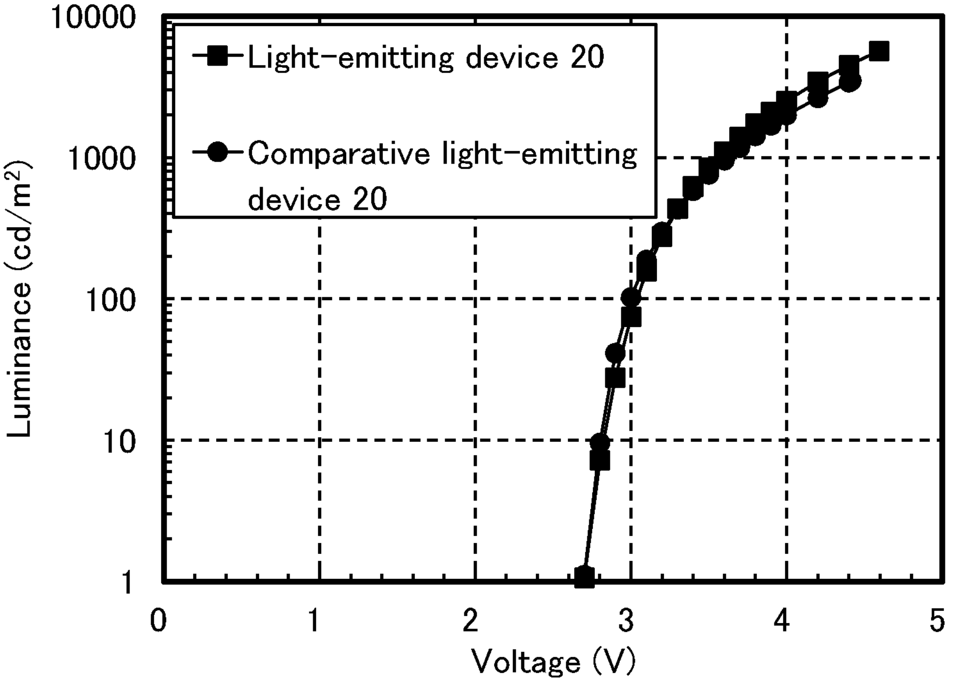
FIG. 30 shows the luminance-voltage characteristics of the light-emitting device 20 and the comparative light-emitting device 20.
Figure 31:
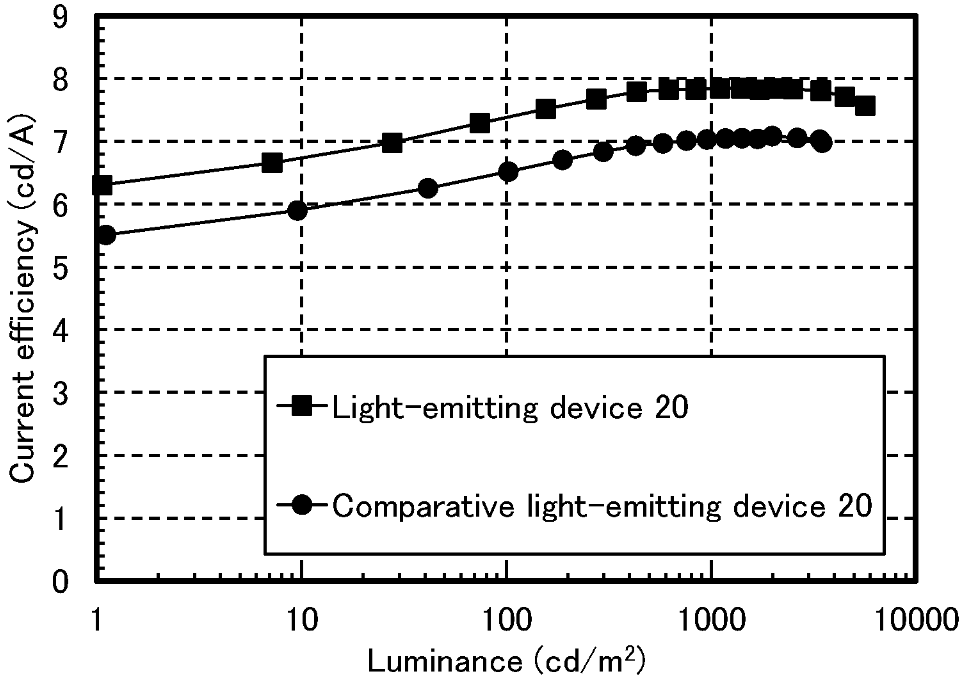
FIG. 31 shows the current efficiency-luminance characteristics of the light-emitting device 20 and the comparative light-emitting device 20.
Figure 32:
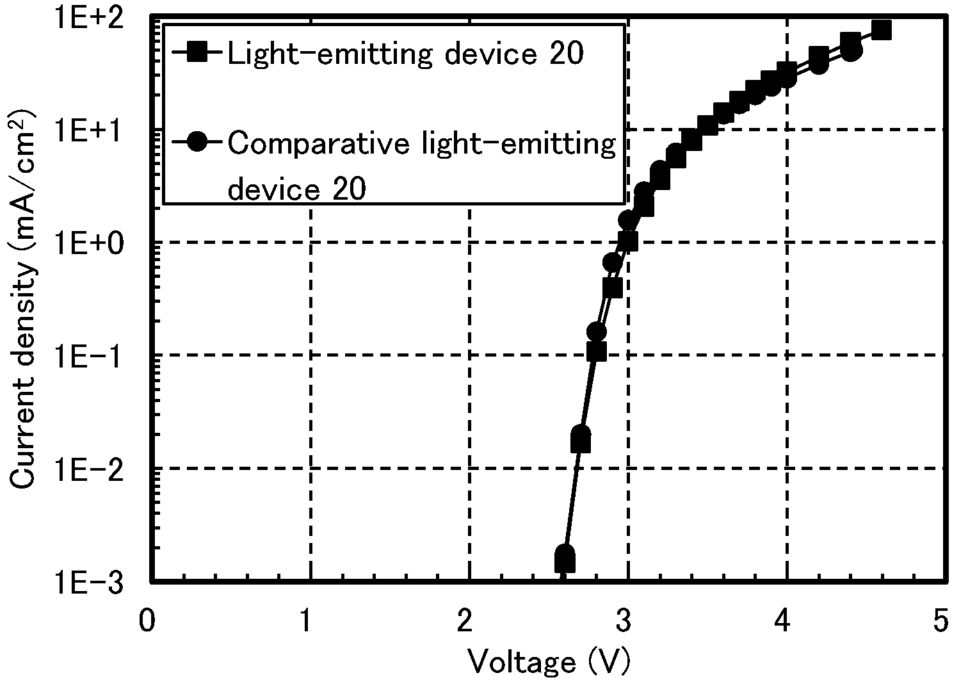
FIG. 32 shows the current density-voltage characteristics of the light-emitting device 20 and the comparative light-emitting device 20.
Figure 33:
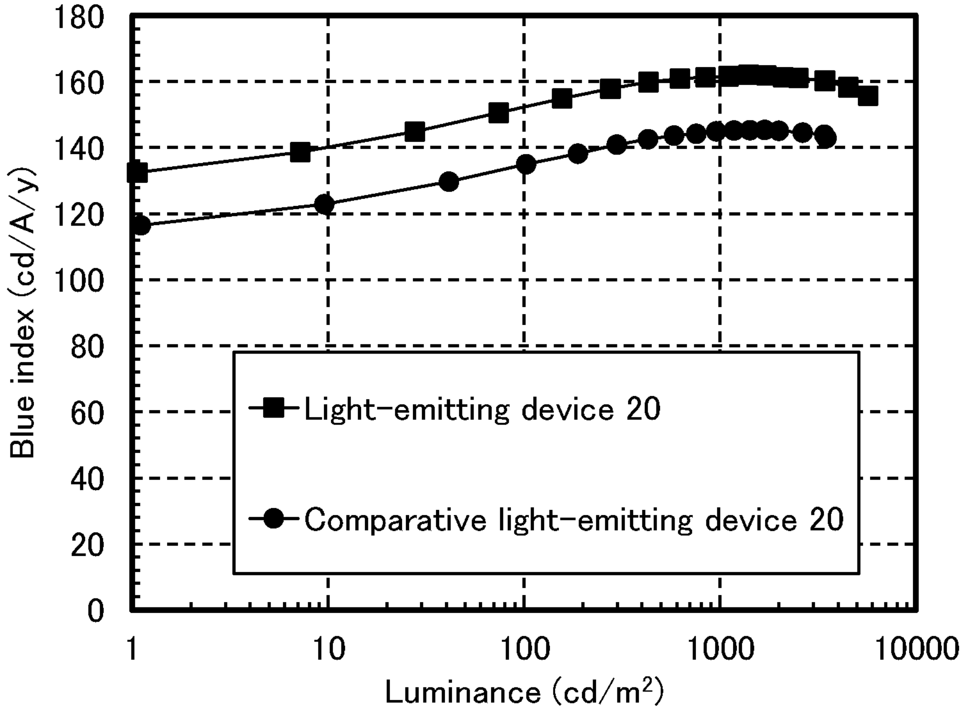
FIG. 33 shows the blue index-luminance characteristics of the light-emitting device 20 and the comparative light-emitting device 20.
Figure 34:
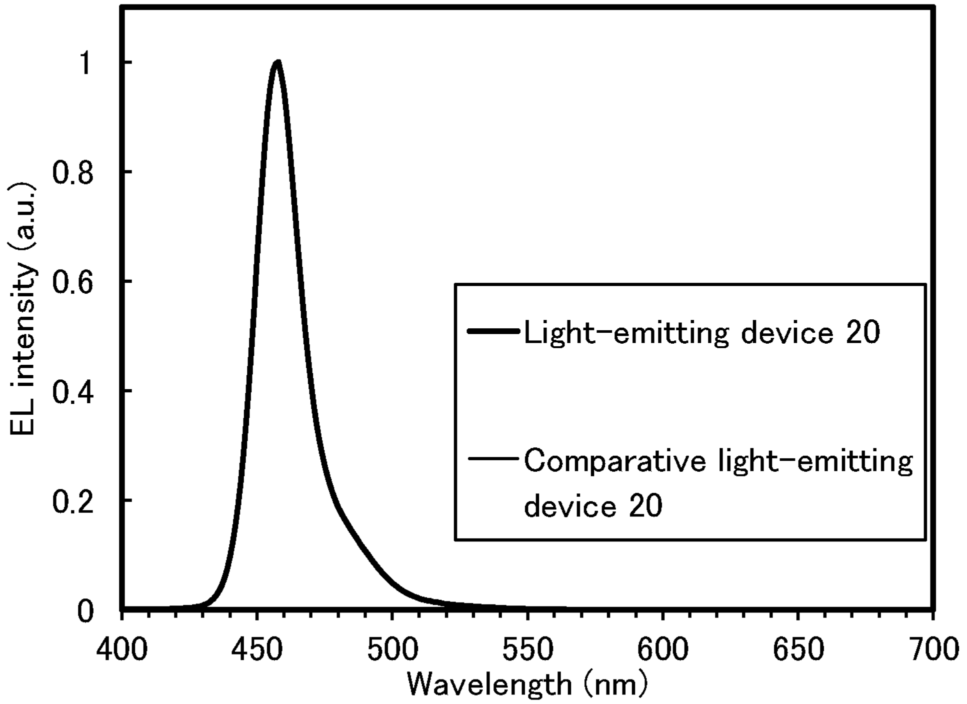
FIG. 34 shows the emission spectra of the light-emitting device 20 and the comparative light-emitting device 20.

FIG. 29 shows the luminance-current density characteristics of the light-emitting device 20 and the comparative light-emitting device 20, FIG. 30 shows the luminance-voltage characteristics thereof, FIG. 31 shows the current efficiency-luminance characteristics thereof, FIG. 32 shows the current density-voltage characteristics thereof, FIG. 33 shows the blue index-luminance characteristics thereof, and FIG. 34 shows the emission spectra thereof. Table 11 shows the main characteristics of the light-emitting devices at a luminance of about 1000 cd/m$^2$. Luminance, CIE chromaticity, and emission spectra were measured with a spectroradiometer (UR-UL1R produced by TOPCON TECHNOHOUSE CORPORATION). Note that the blue index (BI) is a value obtained by dividing current efficiency (cd/A) by chromaticity y, and is one of the indicators of characteristics of blue light emission. As the chromaticity y is smaller, the color purity of blue light emission tends to be higher. With high color purity, a wide range of blue can be expressed even with a small number of luminance components; thus, using blue light emission with high color purity reduces the luminance needed for expressing blue, leading to lower power consumption. Thus, BI that is based on chromaticity y, which is one of the indicators of color purity of blue, is suitably used as a means for showing efficiency of blue light emission. The light-emitting device with higher BI can be regarded as a blue light-emitting device having higher efficiency for a display.

TABLE 11

| | Voltage (V) | Current (mA) | Current density (mA/cm$^2$) | Chromaticity x | Chromaticity y | Current efficiency (cd/A) | BI (cd/A/y) |
|---|---|---|---|---|---|---|---|
| Light-emitting device 20 | 3.6 | 0.56 | 14.1 | 0.14 | 0.05 | 7.8 | 162 |
| Comparative light-emitting device 20 | 3.6 | 0.54 | 13.6 | 0.14 | 0.05 | 7.0 | 145 |

FIG. 29 to FIG. 34 show that the light-emitting device 20 of one embodiment of the present invention has a significantly high blue index and favorable emission efficiency and chromaticity by including a low-refractive-index organic compound in the hole-injection layer and the hole-transport layer, while exhibiting a driving voltage equivalent to that of the comparative light-emitting device 20. Accordingly, the light-emitting device of one embodiment of the present invention is a light-emitting device with low power consumption.

Figure 35:
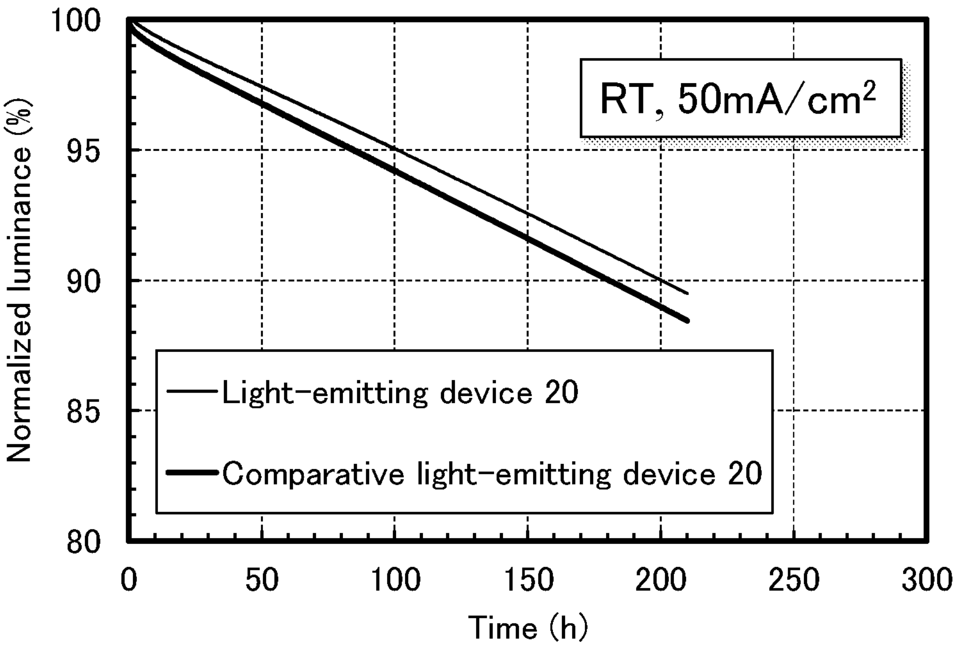
FIG. 35 shows the time dependence of normalized luminance of the light-emitting device 20 and the comparative light-emitting device 20.

FIG. 35 is a graph showing a change in luminance over driving time of the light-emitting device 20 and the comparative light-emitting device 20 at a current density of 50 mA/cm$^2$. As shown in FIG. 35, the light-emitting device 20, which is the light-emitting device of one embodiment of the present invention, was found to have more favorable lifetime than the comparative light-emitting device 20.

Example 7

In this example, light-emitting devices including the organic compounds of embodiments of the present invention and comparative light-emitting devices will be described in detail. Structural formulae of typical organic compounds used in this example are shown below.

[Chemical formulae 22]

(i)

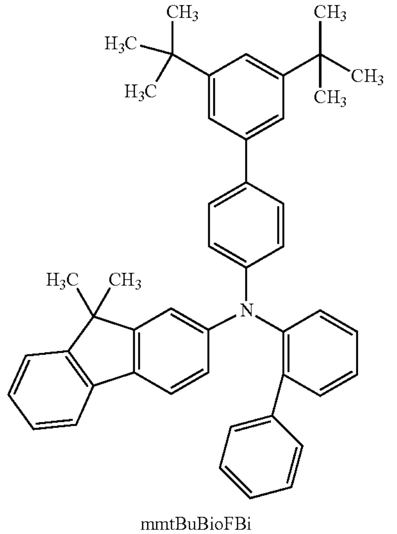

mmtBuBioFBi (viii)

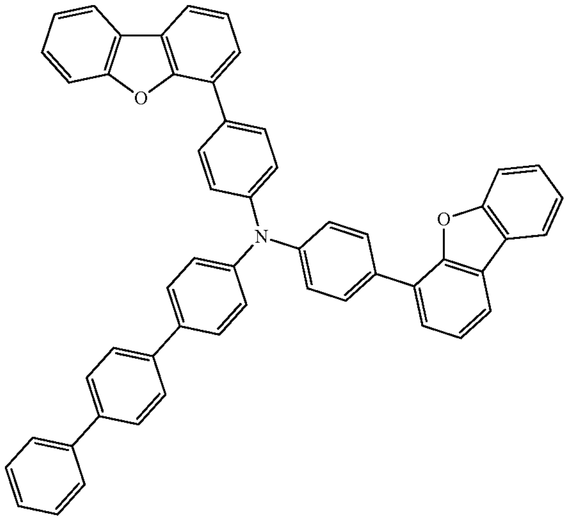

DBfBB1TP

-continued
(ix)
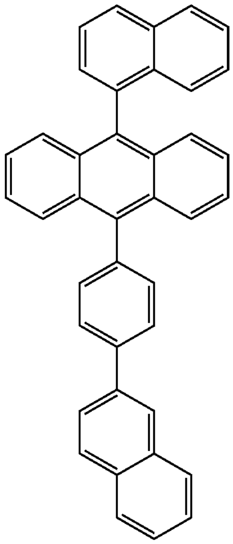
αN-βNPAnth
(xii)
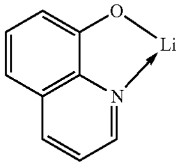
Liq
(xxi)
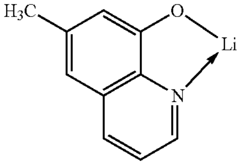
Li-6mq
(x)
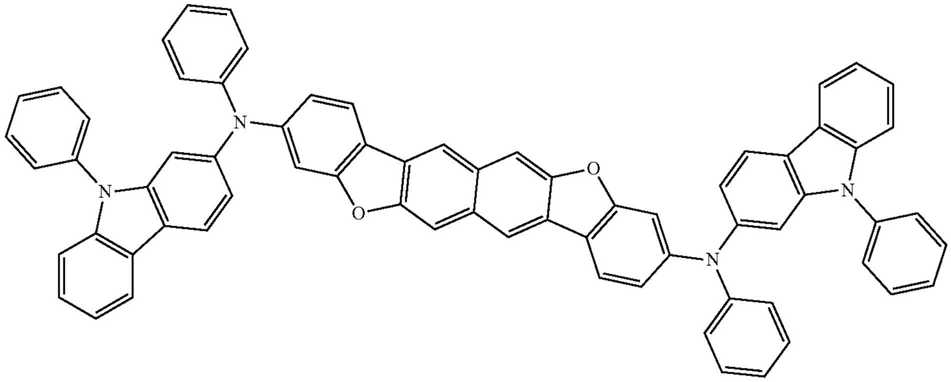
3,10PCA2Nbf(IV)-02

-continued
(xvii)
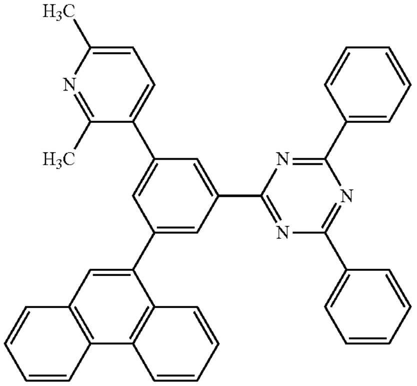
mPn-mDMePyPTzn
(xiii)
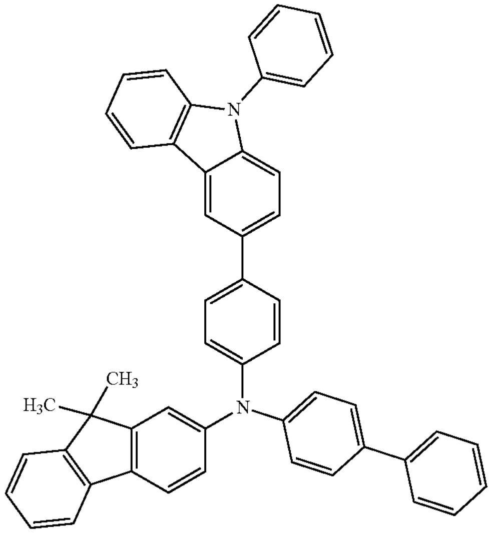
PCBBiF
(xiii)
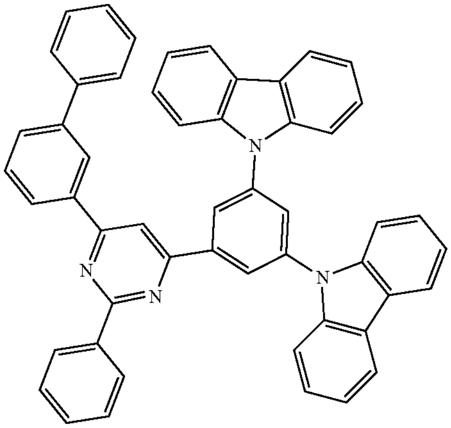
6mBP-4Cz2PPm
(xx)
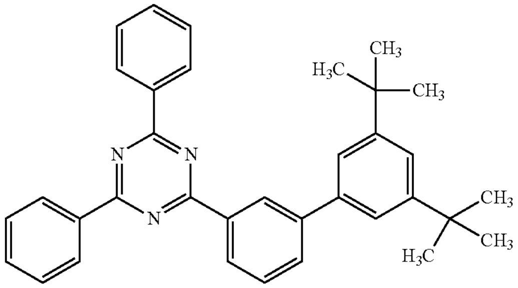
mmtBumBPTzn
(xviii)
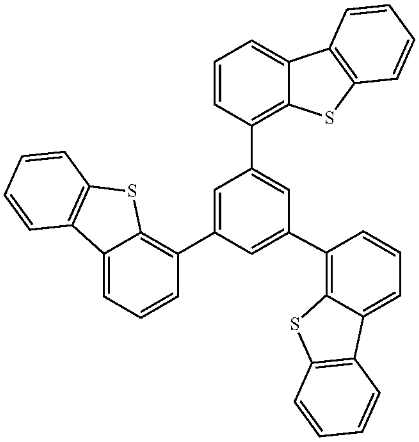
DBT3P-11

(Method for Fabricating Light-Emitting Device 30)

First, silver (Ag) was deposited over a glass substrate to a thickness of 100 nm to form a reflective electrode. After that, indium tin oxide containing silicon oxide (ITSO) was deposited by a sputtering method to form the first electrode 101. The thickness of the first electrode 101 was 10 nm and the electrode area was 2 mm×2 mm.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus so that a surface over which the first electrode 101 was formed faced downward. Then, a low-refractive-index organic compound (low-n HTM) and an electron acceptor material (OCHD-001) were deposited over the first electrode 101 to a thickness of 10 nm by co-evaporation using an evaporation method with resistance heating so that the weight ratio of the low-n HTM to the OCHD-001 was 1:0.1; thus, the hole-injection layer 111 was formed.

Note that N-3',5'-ditertiarybutyl-1,1'-biphenyl-4-yl-N-1, 1'-biphenyl-2-yl-9,9,-dimethyl-9H-fluoren-2-amine (abbreviation: mmtBuBioFBi) represented by the structural formula (i) was used as the low-n HTM.

Subsequently, mmtBuBioFBi was deposited over the hole-injection layer 111 by evaporation to a thickness of 125 nm to form the hole-transport layer 112. Then, N,N-bis[4-(dibenzofuran-4-yl)phenyl]-4-amino-p-terphenyl (abbreviation: DBfBB1TP) represented by the structural formula (viii) was deposited by evaporation to a thickness of 10 nm, whereby an electron-blocking layer was formed.

Then, 9-(1-naphthyl)-10-[4-(2-naphthyl)phenyl]anthracene (abbreviation: αN-PNPAnth) represented by the structural formula (ix) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by the structural formula (x) were deposited by co-evaporation to a thickness of 20 nm so that the weight ratio of αN-βNPAnth to 3,10PCA2Nbf(IV)-02 was 1:0.015; thus, the light-emitting layer 113 was formed.

After that, 6-(1,1'-biphenyl-3-yl)-4-[3,5-bis(9H-carbazol-9-yl)phenyl]-2-phenylpyrimidine (abbreviation: 6mBP-4Cz2PPm) represented by the structural formula (xix) was deposited over the light-emitting layer 113 by evaporation to a thickness of 10 nm, whereby a hole-blocking layer was formed. Then, 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by the structural formula (xvii) and 8-quinolinolato-lithium (abbreviation: Liq) represented by the structural formula (xii) were deposited by co-evaporation to a thickness of 20 nm so that the weight ratio of mPn-mDMePyPTzn to Liq was 1:1; thus, the electron-transport layer 114 was formed.

After the formation of the electron-transport layer 114, lithium fluoride (LiF) was deposited by evaporation to a thickness of 1 nm to form the electron-injection layer 115. Then, silver (Ag) and magnesium (Mg) were deposited by co-evaporation to a thickness of 15 nm so that the weight ratio of Ag to Mg was 10:1; thus, the second electrode 102 was formed. In that manner, a light-emitting device 30 was fabricated. Note that the second electrode 102 has a light-transmitting property, and the light-emitting device 30 is a top-emission light-emitting device in which emitted light is extracted from the second electrode side. Over the second electrode 102, 4,4',4"-(benzene-1,3,5-triyl)tri(dibenzothiophene) (abbreviation: DBT3P-II) represented by the structure formula (xviii) was deposited by evaporation to a thickness of 70 nm to improve outcoupling efficiency.

(Method for Fabricating Light-Emitting Device 31)

A light-emitting device 31 was fabricated in a manner similar to that for the light-emitting device 30 except that mPn-mDMePyPTzn in the light-emitting device 30 was replaced with 2-{(3',5'-di-tert-butyl)-1,1'-biphenyl-3-yl}-4, 6-diphenyl-1,3,5-triazine (abbreviation: mmtBumBPTzn) represented by the structural formula (xx) and Liq in the light-emitting device 30 was replaced with 6-methyl-8-quinolinolato-lithium (abbreviation: Li-6mq) represented by the structural formula (xxi).

(Method for Fabricating Comparative Light-Emitting Device 30)

A comparative light-emitting device 30 was fabricated in a manner similar to that for the light-emitting device 31 except that mmtBuBioFBi in the light-emitting device 31 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (xiii) and the thickness of the hole-transport layer was changed to 115 nm.

(Method for Fabricating Comparative Light-Emitting Device 31)

A comparative light-emitting device 31 was fabricated in a manner similar to that for the light-emitting device 30 except that mmtBuBioFBi in the light-emitting device 30 was replaced with PCBBiF and the thickness of the hole-transport layer was changed to 115 nm.

The structures of the light-emitting devices and the comparative light-emitting devices are listed in the following table.

TABLE 12

| Hole-injection layer | Hole-transport layer | Electron-blocking layer | Light-emitting layer | Hole-blocking layer | Electron-transport layer | Electron-injection layer |
|---|---|---|---|---|---|---|
| 10 nm<br>HTM:<br>OCHD-001<br>(1:0.1) | *3<br>HTM | 10 nm<br>DBfBB1TP | 20 nm<br>αN-βNPAnth:<br>3,10PCA2Nbf(IV)-02<br>(1:0.015) | 10 nm<br>6mBP-4Cz2PPm | 20 nm<br>ETM:<br>Li complex<br>(1:1) | 1 nm<br>LiF |

*3 Light-emitting devices 30 and 31: 125 nm

Comparative light-emitting devices 30 and 31: 115 nm

TABLE 13

| | HTM | ETM | Li complex |
|---|---|---|---|
| Light-emitting device 30 | mmtBuBioFBi | mPn-mDMePyPTzn | Liq |
| Light-emitting device 31 | | mmtBumBPTzn | Li-6mq |
| Comparative light-emitting device 30 | PCBBiF | | |
| Comparative light-emitting device 31 | | mPn-mDMePyPTzn | Liq |

The following table shows the ordinary refractive indices $n_o$, the birefringence Δn, and the alignment order parameters S of the deposited films of the low-n HTM and PCBBiF serving as a comparative material. The low-n HTM and PCBBiF were used in the hole-injection layers and the hole-transport layers.

TABLE 14

| | HTM | Refractive index $n_o$ (@458 nm) | Birefringence Δn (@458 nm) | Alignment order parameter S |
|---|---|---|---|---|
| Light-emitting device 30 | mmtBuBioFBi | 1.74 | 0.004 | −0.059 |
| Light-emitting device 31 | | | | |
| Comparative light-emitting device 30 | PCBBiF | 1.83 | 0.243 | −0.281 |
| Comparative light-emitting device 31 | | | | |

The light-emitting devices and the comparative light-emitting devices were sealed using a glass substrate in a glove box containing a nitrogen atmosphere so as not to be exposed to the air (a sealing material was applied to surround the devices and UV treatment and heat treatment at 80° C. for one hour were performed at the time of sealing). Then, the initial characteristics of the light-emitting devices were measured. Note that particular treatment for improving outcoupling efficiency was not performed on the glass substrate over which the light-emitting device was formed.

Figure 36:
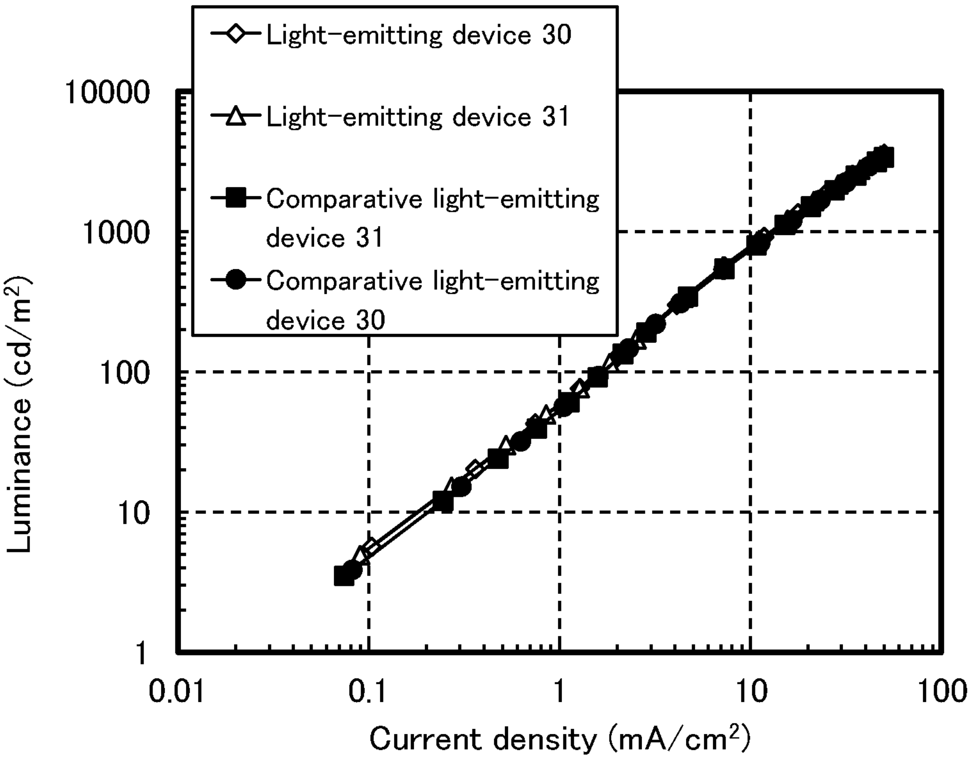
FIG. 36 shows the luminance-current density characteristics of light-emitting devices 30 and 31 and comparative light-emitting devices 30 and 31.
Figure 37:
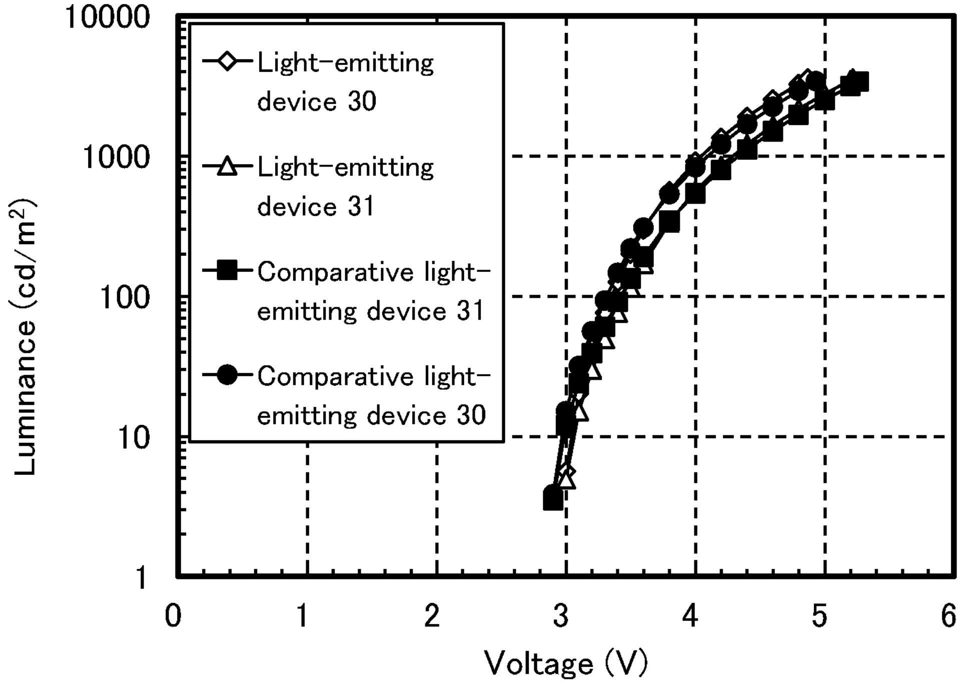
FIG. 37 shows the luminance-voltage characteristics of the light-emitting devices 30 and 31 and the comparative light-emitting devices 30 and 31.
Figure 38:
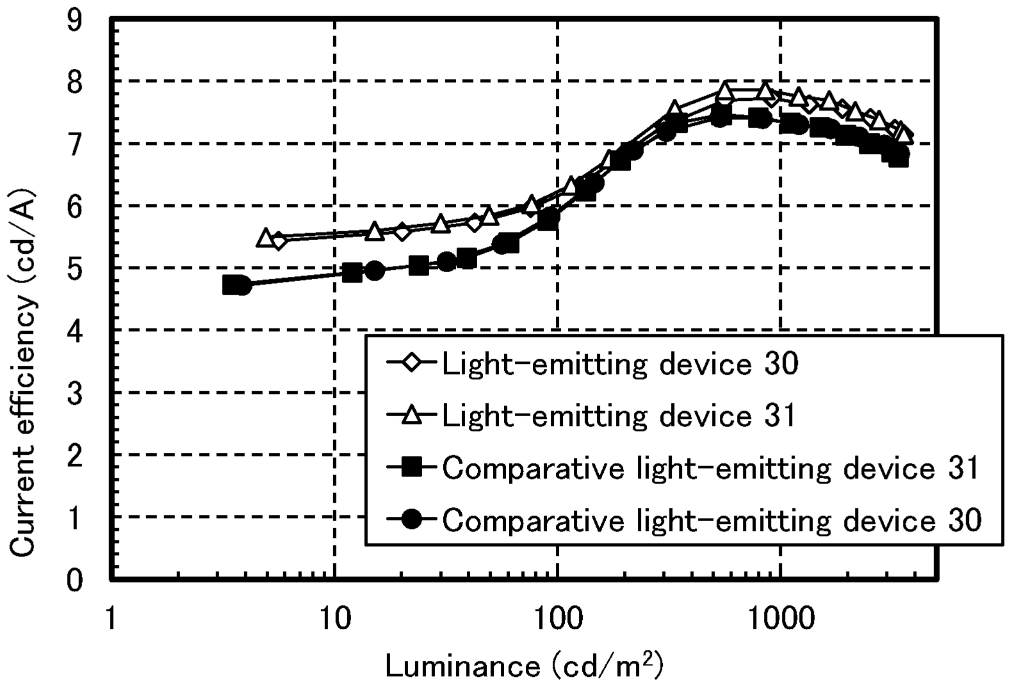
FIG. 38 shows the current efficiency-luminance characteristics of the light-emitting devices 30 and 31 and the comparative light-emitting devices 30 and 31.
Figure 39:
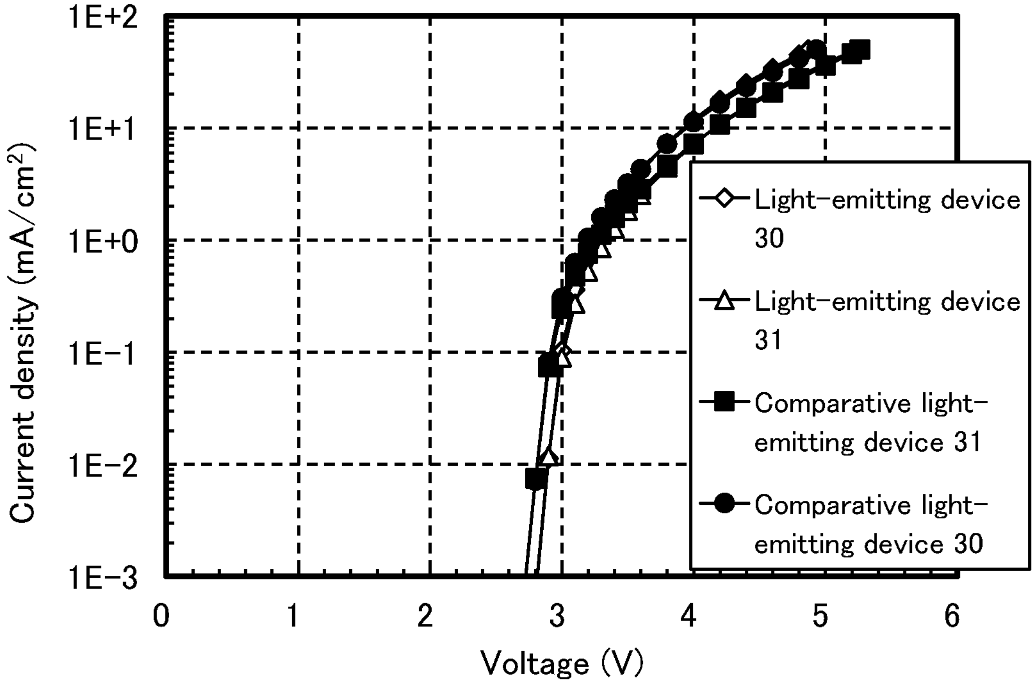
FIG. 39 shows the current density-voltage characteristics of the light-emitting devices 30 and 31 and the comparative light-emitting devices 30 and 31.
Figure 40:
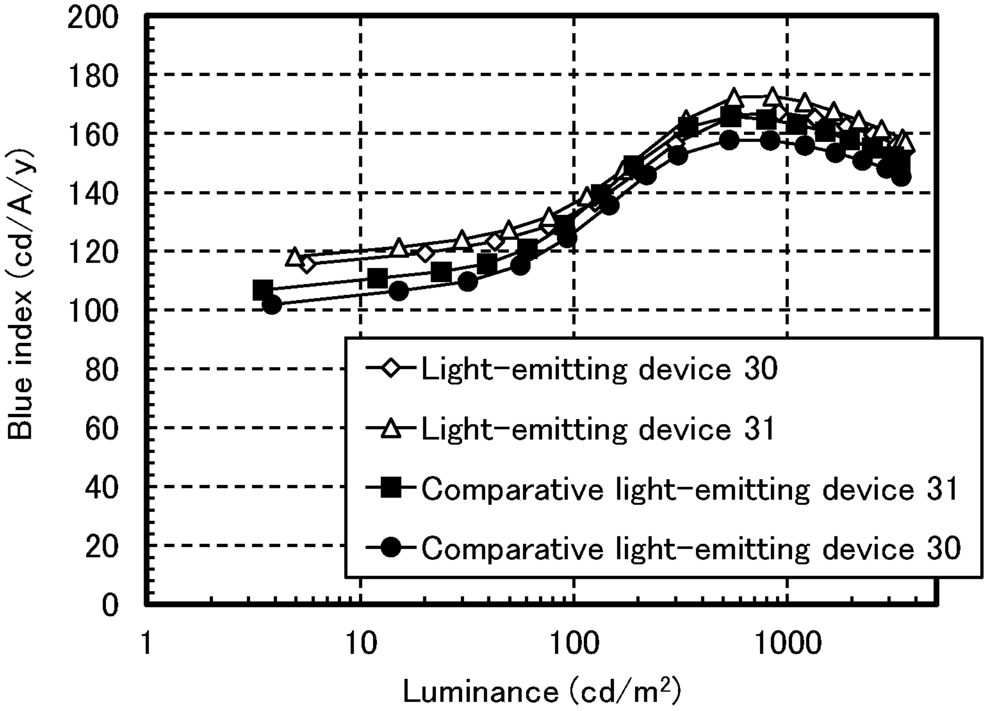
FIG. 40 shows the blue index-luminance characteristics of the light-emitting devices 30 and 31 and the comparative light-emitting devices 30 and 31.
Figure 41:
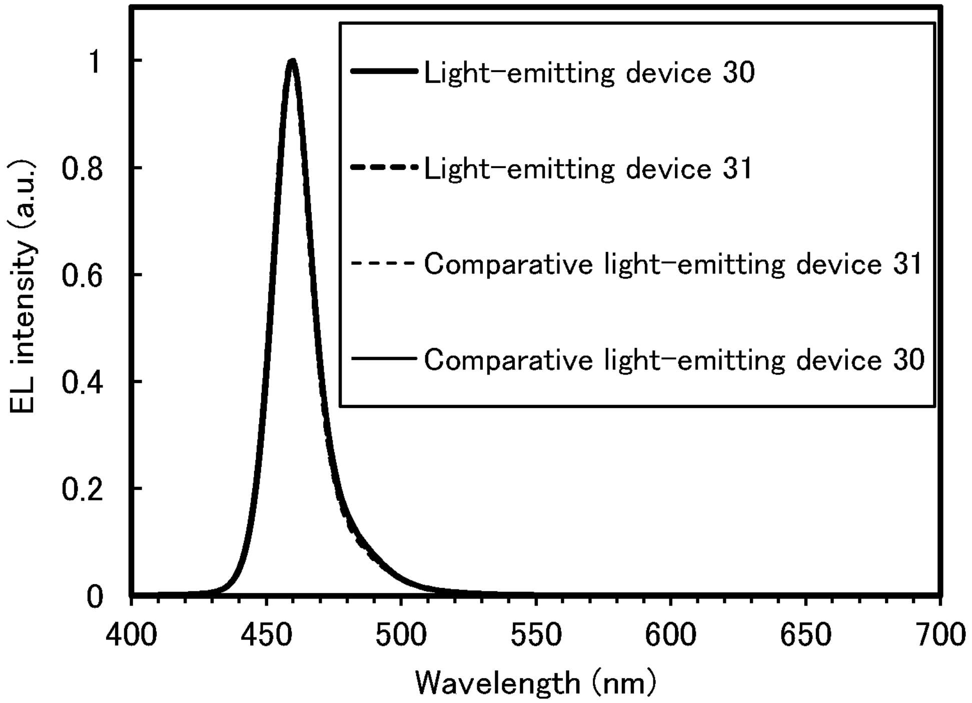
FIG. 41 shows the emission spectra of the light-emitting devices 30 and 31 and the comparative light-emitting devices 30 and 31.

FIG. 36 shows the luminance-current density characteristics of the light-emitting devices 30 and 31 and the comparative light-emitting devices 30 and 31, FIG. 37 shows the luminance-voltage characteristics thereof, FIG. 38 shows the current efficiency-luminance characteristics thereof, FIG. 39 shows the current density-voltage characteristics thereof, FIG. 40 shows the blue index-luminance characteristics thereof, and FIG. 41 shows the emission spectra thereof. Table 15 shows the main characteristics of the light-emitting devices at a luminance of about 1000 cd/m$^2$. Luminance, CIE chromaticity, and emission spectra were measured with a spectroradiometer (UR-UL1R produced by TOPCON TECHNOHOUSE CORPORATION).

TABLE 15

| | Voltage (V) | Current (mA) | Current density (mA/cm$^2$) | Chromaticity x | Chromaticity y | Current efficiency (cd/A) | BI (cd/A/y) |
|---|---|---|---|---|---|---|---|
| Light-emitting device 30 | 4.0 | 0.47 | 11.8 | 0.14 | 0.05 | 7.7 | 167 |
| Light-emitting device 31 | 4.2 | 0.43 | 10.9 | 0.14 | 0.05 | 7.9 | 173 |
| Comparative light-emitting device 30 | 4.4 | 0.61 | 15.2 | 0.14 | 0.04 | 7.3 | 166 |
| Comparative light-emitting device 31 | 4.0 | 0.45 | 11.2 | 0.14 | 0.05 | 7.4 | 158 |

FIG. 36 to FIG. 41 show that the light-emitting devices of one embodiment of the present invention each have a significantly high blue index and favorable emission efficiency and chromaticity as compared to the comparative light-emitting devices by including a low-refractive-index organic compound in the hole-injection layer and the hole-transport layer. Accordingly, the light-emitting devices of one embodiment of the present invention are light-emitting devices with low power consumption. Note that mmtBumBPTzn and Li-6mq, which were used in the electron-transport layers of the light-emitting device 31 and the comparative light-emitting device 30, have a lower refractive index than PCBBiF and Liq, which were used in the light-emitting device 30 and the comparative light-emitting device 31.

Figure 42:
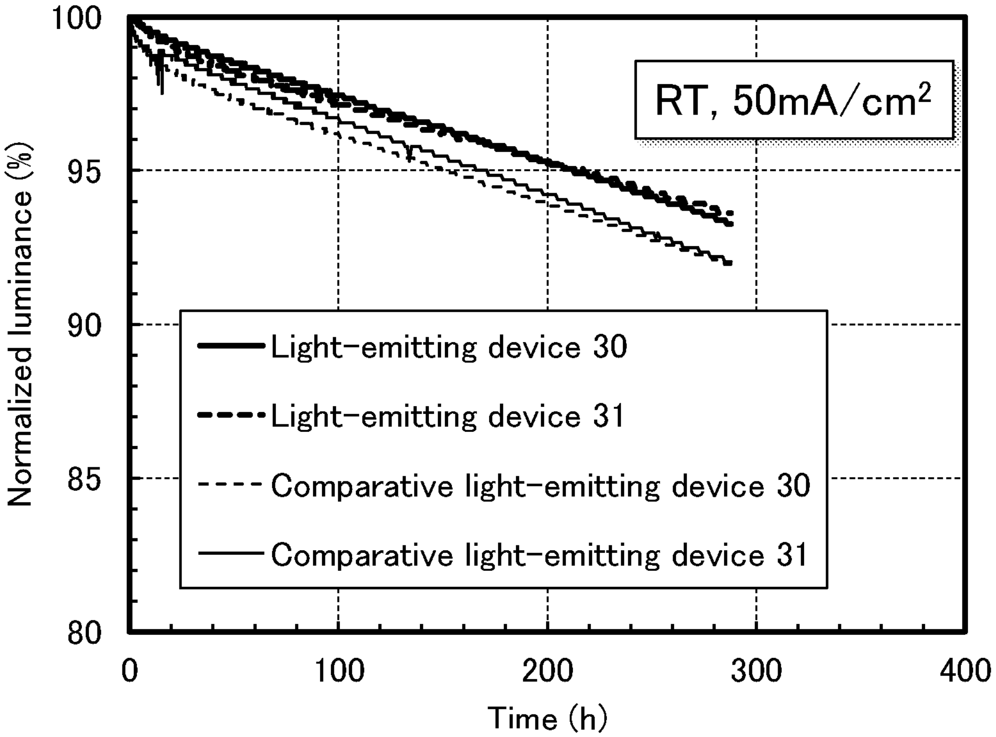
FIG. 42 shows the time dependence of normalized luminance of the light-emitting devices 30 and 31 and the comparative light-emitting devices 30 and 31.

FIG. 42 is a graph showing a change in luminance over driving time of the light-emitting devices 30 and 31 and the comparative light-emitting devices 30 and 31 at a current density of 50 mA/cm$^2$. As shown in FIG. 42, the light-emitting devices 30 and 31, which are the light-emitting devices of embodiments of the present invention, were found to have favorable lifetime.

REFERENCE EXAMPLES

Reference Synthesis Example 1

In this example, a method for synthesizing N-(3,5-ditertiarybutylphenyl)-N-(3',5',-ditertiarybutyl-1,1'-biphenyl-4-yl)-9,9,-dimethyl-9H-fluoren-2-amine (abbreviation: mmtBuBimmtBuPAF), which was used as the low-refractive-index organic compound in Example 1, will be described. The structure of mmtBuBimmtBuPAF is shown below.

[Chemical formula 23]

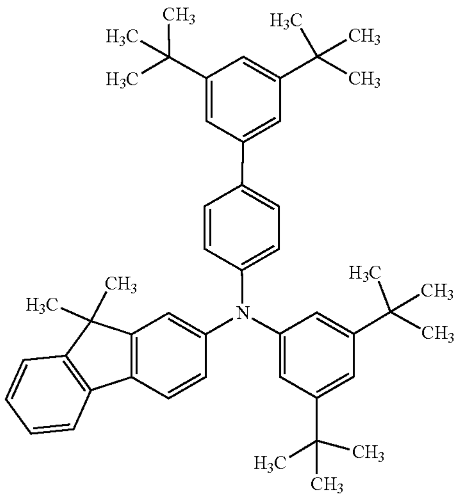

(mmtBuBimmtBuPAF)

Step 1: Synthesis of 3',5'-ditertiarybutyl-4-chloro-1,1'-biphenyl

The synthesis was conducted in a similar manner to the Step 1 of the synthesis example 3 in Example 3.

Step 2: Synthesis of N-(3',5'-ditertiarybutyl-1,1'-biphenyl-4-yl)-N-(9,9,-dimethyl-9H-fluoren-2-yl) amine In a three-neck flask were put 2.8 g (13.5 mmol) of 9,9-dimethyl-9H-fluoren-2-amine, 6.1 g (20.3 mmol) of 3',5'-ditertiarybutyl-4-chloro-1,1'-biphenyl obtained in Step 1, 5.8 g (60.8 mmol) of sodium-tert-butoxide, and 70 mL of xylene, and the mixture was degassed under reduced pressure. Then, the air in the flask was replaced with nitrogen. The mixture was stirred while being heated to approximately 50° C. Then, 100 mg (0.27 mmol) of allylpalladium(II) chloride dimer (abbreviation: $[(Allyl)PdCl]_2$) and 381 mg (1.08 mmol) of di-tert-butyl(1-methyl-2,2-diphenylcyclopropyl)phosphine (abbreviation: cBRIDP (registered trademark)) were added, and the mixture was heated at 120° C. for approximately three hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. A toluene solution of the obtained mixture was purified by silica gel column chromatography, and the resulting solution was concentrated to give a condensed toluene solution. The precipitate was filtrated at 20° C., and the obtained solid was dried at approximately 80° C. under reduced pressure, whereby 2.9 g of a brown oily substance N-(3',5'-ditertiarybutyl-1,1'-biphenyl-4-yl)-N-(9,9,-dimethyl-9H-fluoren-2-yl)amine was obtained in a yield of 46%. The synthesis scheme of Step 2 is shown below

[Chemical formula 24]

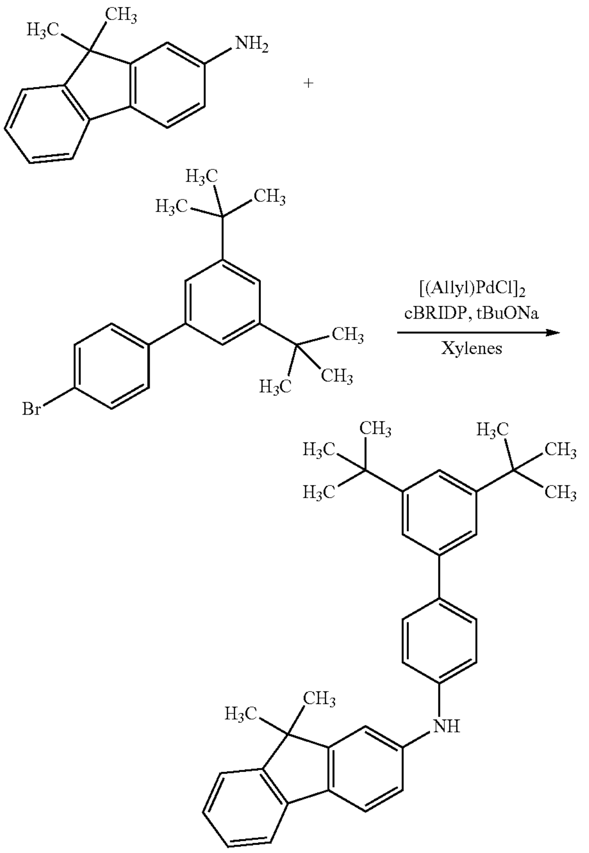

Step 3: Synthesis of N-(3,5-ditertiarybutylphenyl)-N-(3',5',-ditertiarybutyl-1,1'-biphenyl-4-yl)-9,9,-dimethyl-9H-fluoren-2-amine (Abbreviation: mmtBuBimmtBuPAF)

In a three-neck flask were put 2.7 g (5.7 mmol) of N-(3',5'-ditertiarybutyl-1,1'-biphenyl-4-yl)-N-(9,9,-dimethyl-9H-fluoren-2-yl)amine obtained in Step 2, 1.5 g (5.7 mmol) of 3,5-ditertiarybutyl-1-bromobenzene, 1.6 g (17.0 mmol) of sodium-tert-butoxide, and 30 mL of xylene. This mixture was degassed under reduced pressure, and then the air in the flask was replaced with nitrogen. The mixture was stirred while being heated to approximately 50° C. Then, 21 mg (0.057 mmol) of allylpalladium(II) chloride dimer (abbreviation: [(Allyl)PdCl]2) and 73 mg (0.208 mmol) of di-tert-butyl(1-methyl-2,2-diphenylcyclopropyl)phosphine (abbreviation: cBRIDP (registered trademark)) were added, and the mixture was heated at 120° C. for approximately 7 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. A toluene solution of the obtained mixture was purified by silica gel column chromatography, and the resulting solution was concentrated to give a condensed toluene solution. The precipitate was filtrated at 20° C., and the obtained solid was dried at approximately 80° C. under reduced pressure, whereby 3.6 g of a target white solid was obtained in a yield of 95%. The synthesis scheme of Step 3 is shown below.

[Chemical formula 25]

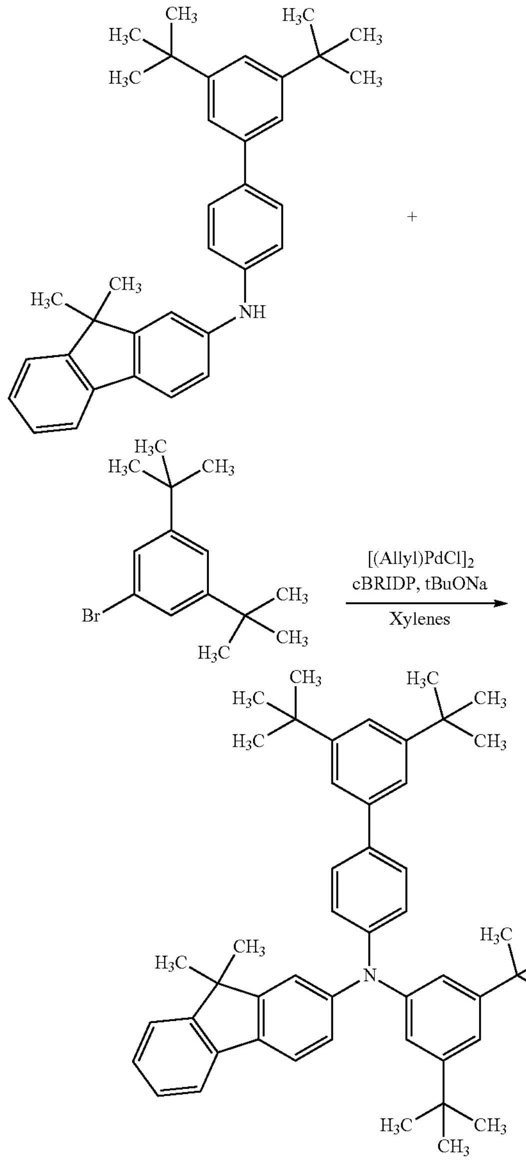

(mmtBuBimmtBuPAF)

Analysis results by nuclear magnetic resonance ($^1$H-NMR) spectroscopy of the white solid obtained in Step 3 are shown below. The results show that N-(3,5-ditertiary-butylphenyl)-N-(3',5',-ditertiarybutyl-1,1'-biphenyl-4-yl)-9,9,-dimethyl-9H-fluoren-2-amine (abbreviation: mmtBuBimmtBuPAF) was synthesized in this synthesis example.

$^1$H-NMR. δ ($CDCl_3$): 7.64 (d, 1H, J=7.5 Hz), 7.57 (d, 1H, J=8.0 Hz), 7.48 (d, 2H, J=8.0 Hz), 7.43 (m, 2H), 7.39 (m, 2H), 7.31 (td, 1H, J=6.0 Hz, 1.5 Hz), 7.15-7.25 (m, 4H), 6.97-7.02 (m, 4H), 1.42 (s, 6H), 1.38 (s, 18H), 1.25 (s, 18H).

Next, 3.2 g of the obtained solid was purified by a train sublimation method. The purification by sublimation was conducted by heating at 210° C. under a pressure of 3.0 Pa with the argon flow rate of 19.3 mL/min. After the purification by sublimation, 3.0 g of a pale yellowish white solid was obtained at a collection rate of 94%.

The refractive index of mmtBuBimmtBuPAF was measured by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method.

The results show that mmtBuBimmtBuPAF is a material with a low refractive index: the ordinary refractive index of mmtBuBimmtBuPAF is within the range of 1.50 to 1.75 in the entire blue emission region (from 455 nm to 465 nm), and the ordinary refractive index of mmtBuBimmtBuPAF at 633 nm is within the range of 1.45 to 1.70.

Reference Synthesis Example 2

In this example, a method for synthesizing N-(3,3",5,5"-tetra-t-butyl-1,1':3',1"-terphenyl-5'-yl)-N-(4-cyclohexylphenyl)-9,9-dimethyl-9H-fluoren-2-amine (abbreviation: mmtBumTPchPAF), which was used as the low-refractive-index organic compound in Example 1, will be described. The structure of mmtBumTPchPAF is shown below.

[Chemical formula 26]

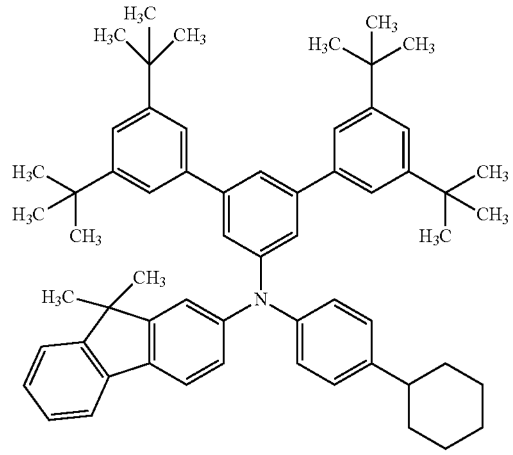

(mmtBumTPChPAF)

Step 1: Synthesis of 3,3",5,5"-tetra-t-butyl-5'-chloro-1,1':3',1"-terphenyl

In a three-neck flask were put 1.66 g (6.14 mmol) of 1,3-dibromo-5-chlorobenzene, 4.27 g (13.5 mmol) of 2-(3,5-di-t-butylphenyl)-4,4,5,5-tetramethyl-1,3,2-dioxaborolane, 187 mg (0.614 mmol) of tris(2-methylphenyl)phosphine (abbreviation: P(o-tolyl)$_3$), 13.5 mL of a 2M aqueous solution of potassium carbonate, 20 mL of toluene, and 10 mL of ethanol. The mixture was degassed by being stirred under reduced pressure, and then the air in the flask was replaced with nitrogen. To the mixture, 27.5 mg (0.122 mmol) of palladium(II) acetate was added, and the mixture was stirred at 80° C. under a nitrogen stream for approximately four hours. After the stirring, water was added to this mixture to separate the mixture into an organic layer and an aqueous layer. Then, an aqueous layer was subjected to extraction with toluene. The obtained solution of the extract and the organic layer were combined, and the mixture was washed with water and saturated saline and dried with magnesium sulfate. This mixture was separated by gravity filtration, and the filtrate was concentrated to give a yellow oily substance. This oily substance was purified by silica gel column chromatography. The obtained fraction was concentrated, whereby 2.98 g of a target white solid was obtained in a yield of 99%. The synthesis scheme of Step 1 is shown below.

[Chemical formula 27]

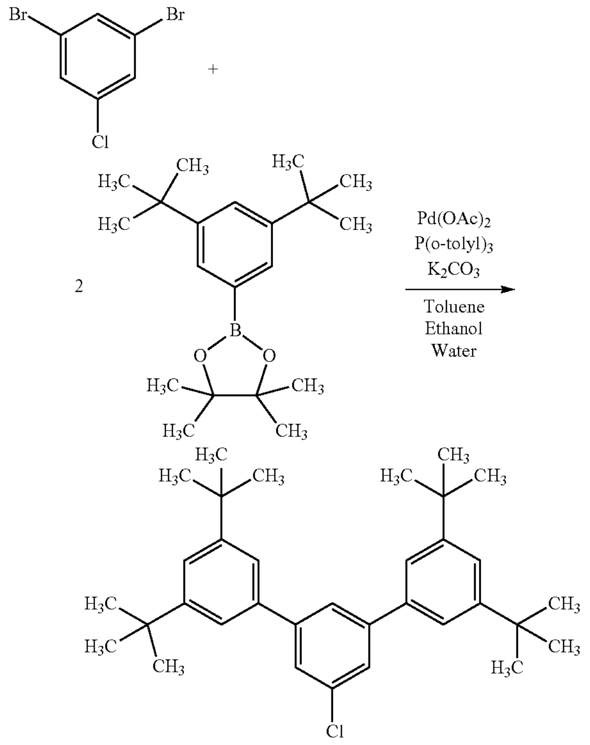

Analysis results by nuclear magnetic resonance ($^1$H-NMR) spectroscopy of the white solid obtained in Step 1 are shown below. The results show that the organic compound 3,3",5,5"-tetra-t-butyl-5'-chloro-1,1':3',1"-terphenyl was synthesized in Step 1.

$^1$H-NMR (300 MHz, $CDCl_3$):δ=7.63-7.64 (m, 1H), 7.52-7.47 (m, 4H), 7.44-7.40 (m, 4H), 1.38 (s, 36H).

Step 2: Synthesis of N-(4-cyclohexylphenyl)-N-(9,9-dimethyl-9H-fluoren-2yl)amine The synthesis was performed in a manner similar to Step 2 of the synthesis example 3 in Example 3.

Step 3: Synthesis of N-(3,3",5,5"-tetra-t-butyl-1,1':3',1"-terphenyl-5'-yl)-N-(4-cyclohexylphenyl)-9,9-dimethyl-9H-fluoren-2-amine (Abbreviation: mmtBumTPchPAF)

In a three-neck flask were put 2.69 g (7.32 mmol) of N-(4-cyclohexylphenyl)-N-(9,9-dimethyl-9H-fluoren-2yl) amine obtained in Step 2, 2.98 g (6.09 mmol) of 3,3",5,5"-tetra-t-butyl-5'-chloro-1,1':3',1"-terphenyl obtained in Step 1, 0.103 g (0.292 mmol) of di-tert-butyl(1-methyl-2,2-diphenylcyclopropyl)phosphine (abbreviation: cBRIDP (registered trademark)), 1.76 g (18.3 mmol) of sodium-tert-butoxide, and 30 mL of xylene. The mixture was degassed by being stirred under reduced pressure, and then the air in the flask was replaced with nitrogen. Then, 26.7 mg (0.0730 mmol) of allylpalladium(II) chloride dimer (abbreviation: $[(Allyl)PdCl]_2$) was added to this mixture, and the mixture was stirred at 120° C. under a nitrogen stream for approximately 10 hours. After the stirring, water was added to the mixture to separate the mixture into an organic layer and an aqueous layer. The obtained aqueous layer was subjected to extraction with toluene. The obtained solution of the extract and the organic layer were combined, and the mixture was washed with water and saturated saline and dried with magnesium sulfate. The mixture was separated by gravity filtration, and the obtained filtrate was concentrated to give a black oily substance. This oily substance was purified by silica gel column chromatography. The obtained fraction was concentrated to give a pale yellow oily substance. This oily substance was purified by high performance liquid column chromatography (developing solvent: chloroform). The obtained fraction was concentrated to give a white solid. Ethanol was added to this solid, followed by irradiation with ultrasonic waves. The solid was collected by suction filtration, whereby 3.36 g of a target white solid was obtained in a yield of 67%. The synthesis scheme of Step 3 is shown below.

[Chemical formula 28]

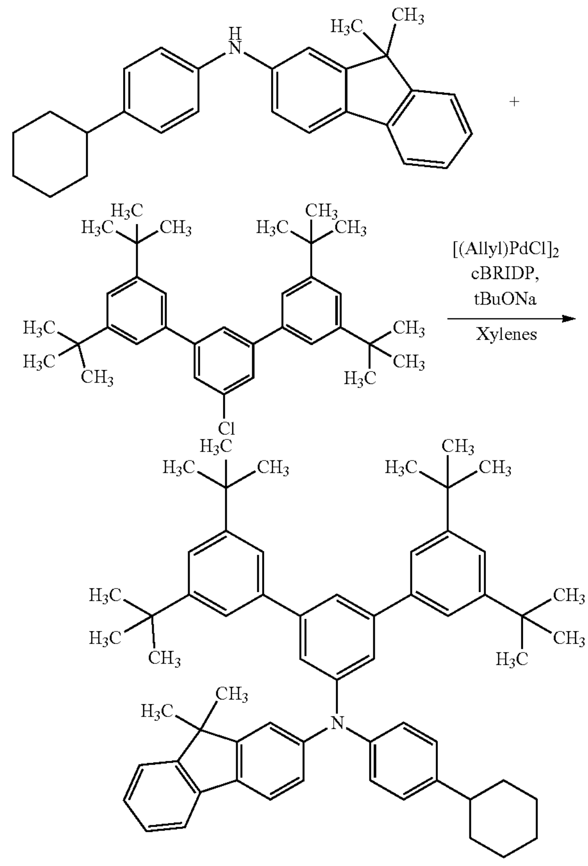

(mmtBumTPchPAF)

Then, 3.36 g of the obtained white solid was purified by a train sublimation method. The purification by sublimation was conducted by heating at 240° C. under a pressure of 5.0 Pa with an argon flow rate of 10 mL/min. After the purification by sublimation, 1.75 g of a colorless transparent glassy solid was obtained at a collection rate of 52%.

Analysis results by nuclear magnetic resonance ($^1$H-NMR) spectroscopy of the white solid obtained in Step 3 are shown below. The results show that N-(3,3",5,5"-tetra-t-butyl-1,1':3',1"-terphenyl-5'-yl)-N-(4-cyclohexylphenyl)-9,9-dimethyl-9H-fluoren-2-amine (abbreviation: mmtBumTPchPAF) was synthesized in this synthesis example.

$^1$H-NMR (300 MHz, $CDCl_3$): δ=7.63 (d, J=6.6 Hz, 1H), 7.58 (d, J=8.1 Hz, 1H), 7.42-7.37 (m, 4H), 7.36-7.09 (m, 14H), 2.55-2.39 (m, 1H), 1.98-1.20 (m, 51H).

The refractive index of mmtBumTPchPAF was measured by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method.

The results show that mmtBumTPchPAF is a material with a low refractive index: the ordinary refractive index is within the range of 1.50 to 1.75 in the entire blue emission region (from 455 nm to 465 nm), and the ordinary refractive index at 633 nm is within the range of 1.45 to 1.70.

Reference Synthesis Example 3

In this example, a method for synthesizing N-(1,1'-biphenyl-2-yl)-N-(3,3",5',5"-tetra-tert-butyl-1,1':3',1"-terphenyl-5-yl)-9,9-dimethyl-9H-fluoren-2-amine (abbreviation: mmtBumTPoFBi-02), which was used as the low-refractive-index organic compound in Example 1, will be described. The structure of mmtBumTPoFBi-02 is shown below.

[Chemical formula 29]

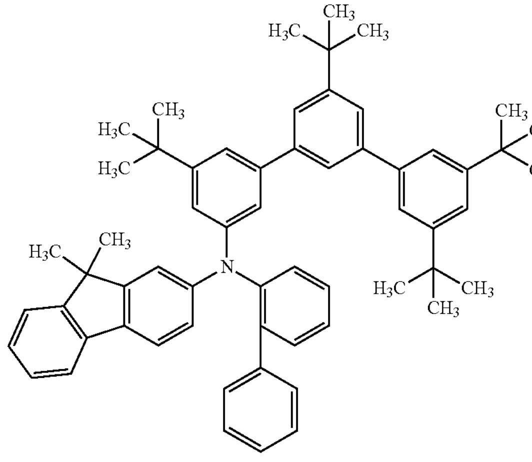

(mmtBumTPoFBi-01)

Step 1: Synthesis of 3-bromo-3',5,5'-tri-tert-butylbiphenyl

Into a three-neck flask were put 37.2 g (128 mmol) of 1,3-dibromo-5-tert-butylbenzene, 20.0 g (85 mmol) of 3,5-di-tert-butylphenylboronic acid, 35.0 g (255 mmol) of potassium carbonate, 570 mL of toluene, 170 mL of ethanol, and 130 mL of tap water. The mixture was degassed under reduced pressure, and then the air in the flask was replaced with nitrogen. Then, 382 mg (1.7 mmol) of palladium acetate and 901 mg (3.4 mmol) of triphenylphosphine were added, and the mixture was heated at 40° C. for approximately five hours. After that, the temperature of the flask was lowered to room temperature and the mixture was separated into an organic layer and an aqueous layer. Magnesium sulfate was added to this organic layer to eliminate moisture, whereby the organic layer was concentrated. The obtained solution was purified by silica gel column chromatography, whereby 21.5 g of a target colorless oily substance was obtained in a yield of 63%. The synthesis scheme of Step 1 is shown below.

[Chemical formula 30]

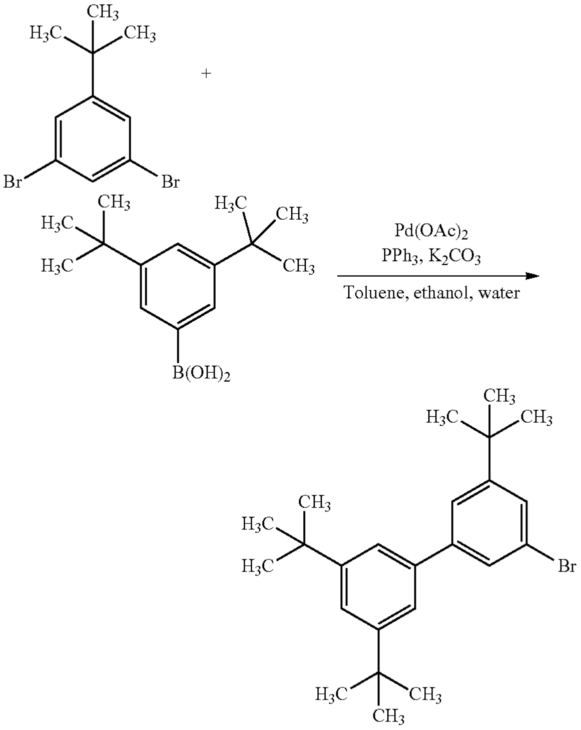

Step 2: Synthesis of 2-(3',5,5'-tri-tert-butyl[1,1'-biphenyl]-3-yl)-4,4,5,5-tetramethyl-1,3,2-dioxaborolane Into a three-neck flask were put 15.0 g (38 mmol) of 3-bromo-3',5,5'-tri-tert-butylbiphenyl obtained in Step 1, 10.5 g (41 mmol) of 4,4,4',4',5,5,5',5'-octamethyl-2,2'-bi-1,3,2-dioxaborolane, 11.0 g (113 mmol) of potassium acetate, and 125 mL of N,N-dimethylformamide. The mixture was degassed under reduced pressure, the air in the flask was replaced with nitrogen, 1.5 g (1.9 mmol) of [1,1'-bis(diphenylphosphino)ferrocene]dichloropalladium(II) (abbreviation: $Pd(dppf)Cl_2$) was added thereto, and the mixture was heated at 100° C. for approximately three hours. Then, the temperature of the flask was lowered to room temperature, and the mixture was separated into an organic layer and an aqueous layer, and extraction was performed with ethyl acetate. Magnesium sulfate was added to the solution of the extract to eliminate moisture, whereby the solution of the extract was concentrated. A toluene solution of the obtained mixture was purified by silica gel column chromatography, and the resulting solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C.

under reduced pressure, whereby 13.6 g of a target white solid was obtained in a yield of 81%. The synthesis scheme of Step 2 is shown below.

[Chemical formula 31]

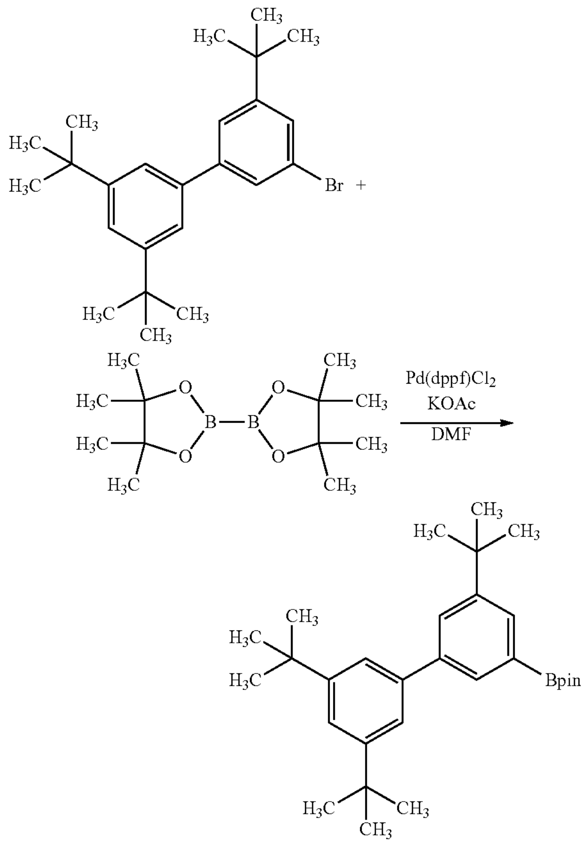

Step 3: Synthesis of 3-bromo-3",5,5',5"-tetra-tert-butyl-1,1':3',1"-terphenyl

Into a three-neck flask were put 5.0 g (11.1 mmol) of 2-(3',5,5'-tri-tert-butyl[1,1'-biphenyl]-3-yl)-4,4,5,5-tetramethyl-1,3,2-dioxaborolane, 4.8 g (16.7 mmol) of 1,3-dibromo-5-tert-butylbenzene, 4.6 g (33.3 mmol) of potassium carbonate, 56 mL of toluene, 22 mL of ethanol, and 17 mL of tap water. The mixture was degassed under reduced pressure, and then the air in the flask was replaced with nitrogen. Then, 50 mg (0.22 mmol) of palladium acetate and 116 mg (0.44 mmol) of triphenylphosphine were added, and the mixture was heated at 80° C. for approximately 10 hours. After that, the temperature of the flask was lowered to room temperature, and the mixture was separated into an organic layer and an aqueous layer. Magnesium sulfate was added to this solution to eliminate moisture, whereby this solution was concentrated. The obtained hexane solution was purified by silica gel column chromatography, whereby 3.0 g of a target white solid was obtained in a yield of 51.0%. The synthesis scheme of 3-bromo-3",5,5',5"-tetra-tert-butyl-1,1':3',1"-terphenyl of Step 3 is shown below.

[Chemical formula 32]

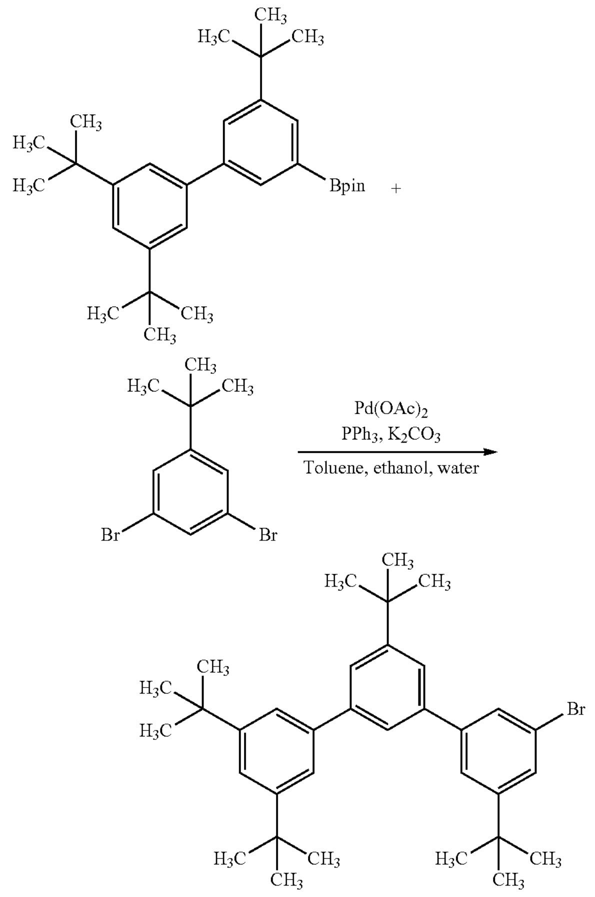

Step 4: Synthesis of mmtBumTPoFBi-02

Into a three-neck flask were put 5.8 g (10.9 mmol) of 3-bromo-3",5,5',5"-tetra-tert-butyl-1,1':3',1"-terphenyl obtained in Step 3, 3.9 g (10.9 mmol) of N-(1,1'-biphenyl-4-yl)-N-phenyl-9,9-dimethyl-9H-fluoren-2-amine, 3.1 g (32.7 mmol) of sodium-tert-butoxide, and 55 mL of toluene. The mixture was degassed under reduced pressure, the air in the flask was replaced with nitrogen, 64 mg (0.11 mmol) of bis(dibenzylideneacetone)palladium(0) and 132 mg (0.65 mmol) of tri-tert-butylphosphine were added thereto, and the mixture was heated at 80° C. for approximately two hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 8.1 g of a target white solid was obtained in a yield of 91%. The synthesis scheme of mmtBumTPoFBi-02 is shown below.

[Chemical formula 33]

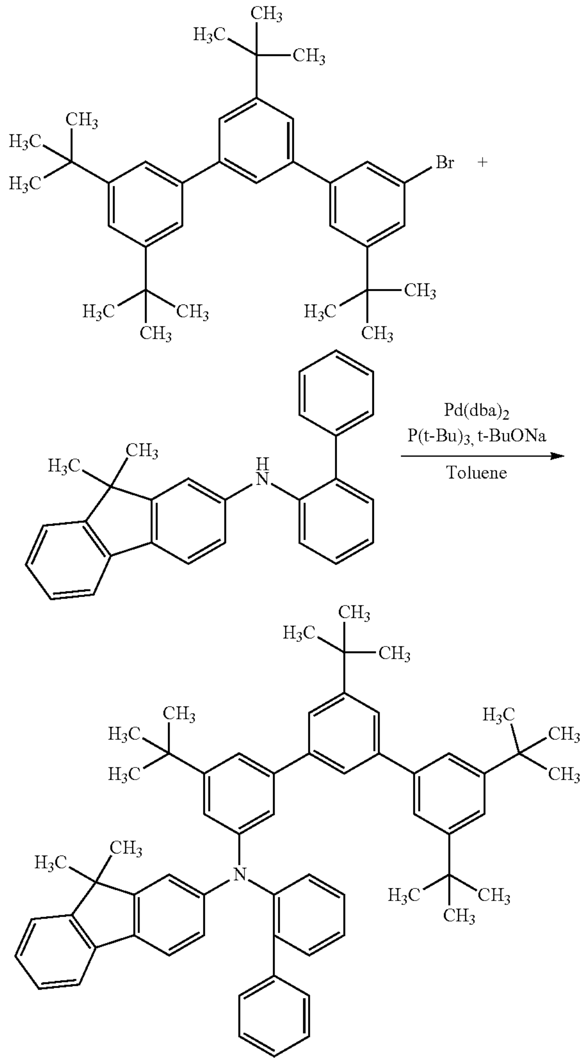

(mmtBumTPoFBi-02)

Analysis results by nuclear magnetic resonance ($^1$H-NMR) spectroscopy of the white powder obtained in the above step are shown below. The results show that N-(1,1'-biphenyl-2-yl)-N-(3,3",5',5"-tetra-tert-butyl-1,1':3',1"-terphenyl-5-yl)-9,9-dimethyl-9H-fluoren-2-amine (abbreviation: mmtBumTPoFBi-02) was synthesized in this synthesis example.

$^1$H-NMR. δ ($CDCl_3$): 7.56 (d, 1H, J=7.4 Hz), 7.50 (dd, 1H, J=1.7 Hz), 7.33-7.46 (m, 11H), 7.27-7.29 (m, 2H), 7.22 (dd, 1H, J=2.3 Hz), 7.15 (d, 1H, J=6.9 Hz), 6.98-7.07 (m, 7H), 6.93 (s, 1H), 6.84 (d, 1H, J=6.3 Hz), 1.38 (s, 9H), 1.37 (s, 18H), 1.31 (s, 6H), 1.20 (s, 9H).

The refractive index of mmtBumTPoFBi-02 was measured by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method.

The results show that mmtBumTPoFBi-02 is a material with a low refractive index: the ordinary refractive index is 1.69 to 1.70 in the entire blue emission region (from 455 nm to 465 nm), which is within the range of 1.50 to 1.75, and the ordinary refractive index at 633 nm is 1.64, which is within the range of 1.45 to 1.70.

Reference Synthesis Example 4

In this example, a method for synthesizing N-(4-cyclohexylphenyl)-N-(3,3",5',5"-tetra-tert-butyl-1,1':3',1"-terphenyl-5-yl)-9,9-dimethyl-9H-fluoren-2-amine (abbreviation: mmtBumTPchPAF-02), which was used as the low-refractive-index organic compound in Example 1, will be described. The structure of mmtBumTPchPAF-02 is shown below.

[Chemical Formula 34]

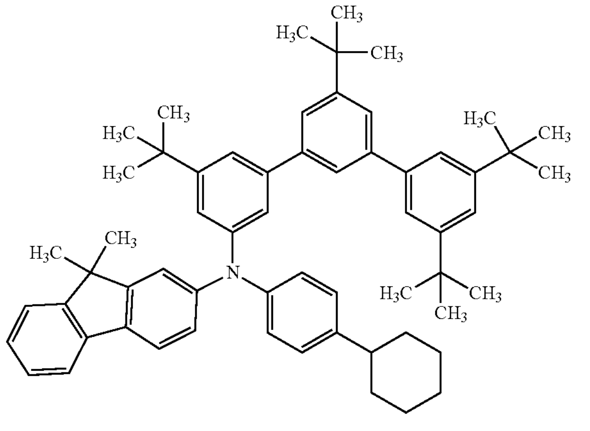

(mmtBumTPChPAF-02)

Step 1: Synthesis of 3-bromo-3',5,5'-tri-tert-butylbiphenyl

The synthesis was performed in a manner similar to Step 1 of the reference synthesis example 3.

Step 2: Synthesis of 2-(3',5,5'-tri-tert-butyl[1,1'-biphenyl]-3-yl)-4,4,5,5-tetramethyl-1,3,2-dioxaborolane The synthesis was performed in a manner similar to Step 2 of the reference synthesis example 3.

Step 3: Synthesis of 3-bromo-3",5,5',5"-tetra-tert-butyl-1,1':3',1"-terphenyl The synthesis was performed in a manner similar to Step 3 of the reference synthesis example 3.

Step 4: Synthesis of mmtBumTPchPAF-02

Into a three-neck flask were put 3.0 g (5.6 mmol) of 3-bromo-3",5,5',5"-tetra-tert-butyl-1,1':3',1"-terphenyl obtained in Step 3, 2.1 g (5.6 mmol) of N-(4-cyclohexylphenyl)-N-(9,9-dimethyl-9H-fluoren-2-yl)amine, 1.6 g (16.9 mmol) of sodium-tert-butoxide, and 28 mL of toluene. The mixture was degassed under reduced pressure, the air in the flask was replaced with nitrogen, 65 mg (0.11 mmol) of bis(dibenzylideneacetone)palladium(0) (abbreviation: Pd(dba)$_2$) and 139 mg (0.34 mmol) of 2-dicyclohexylphosphino-2',6'-dimethoxybiphenyl (abbreviation: S-Phos) were added thereto, and the mixture was heated at 80° C. for approximately two hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 3.7 g of a target white solid was obtained in a yield of 80%. The synthesis scheme of mmtBumTPchPAF-02 is shown below.

[Chemical formula 35]

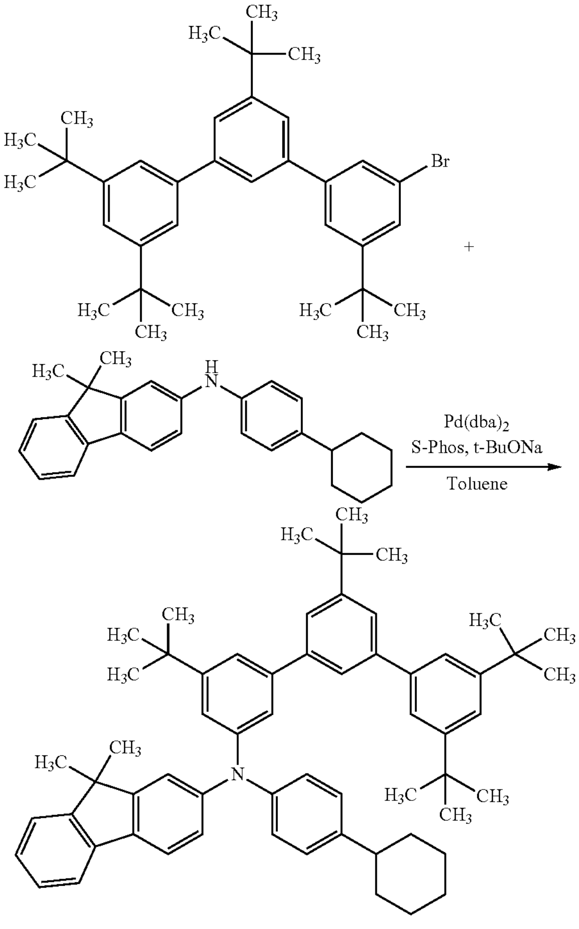

(mmtBumTPChPAF-02)

Analysis results by nuclear magnetic resonance ($^1$H-NMR) spectroscopy of the white solid obtained in the above step are shown below. The results show that N-(4-cyclohexylphenyl)-N-(3,3",5',5"-tetra-tert-butyl-1,1':3',1"-terphenyl-5-yl)-9,9-dimethyl-9H-fluoren-2-amine (abbreviation: mmtBumTPchPAF-02) was synthesized in this synthesis example.

$^1$H-NMR. δ ($CDCl_3$): 7.62 (d, 1H, J=7.5 Hz), 7.56 (d, 1H, J=8.0 Hz), 7.50 (dd, 1H, J=1.7 Hz), 7.46-7.47 (m, 2H), 7.43 (dd, 1H, J=1.7 Hz), 7.37-7.39 (m, 3H), 7.29-7.32 (m, 2H), 7.23-7.25 (m, 2H), 7.20 (dd, 1H, J=1.7 Hz), 7.09-7.14 (m, 5H), 7.05 (dd, 1H, J=2.3 Hz), 2.46 (brm, 1H), 1.83-1.88 (m, 4H), 1.73-1.75 (brm, 1H), 1.42 (s, 6H), 1.38 (s, 9H), 1.36 (s, 18H), 1.29 (s, 9H).

Next, 3.5 g of the obtained white solid was purified by a train sublimation method at 265° C. under a pressure of 4.0 Pa with an argon gas flow rate of 15.0 mL/min. After the purification by sublimation, 3.1 g of a pale yellowish white solid was obtained at a collection rate of 89%.

The refractive index of mmtBumTPchPAF-02 was measured by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method.

The results show that mmtBumTPchPAF-02 is a material with a low refractive index: the ordinary refractive index is 1.67 to 1.68 in the entire blue emission region (from 455 nm to 465 nm), which is within the range of 1.50 to 1.75, and the ordinary refractive index at 633 nm is 1.62, which is within the range of 1.45 to 1.70.

This application is based on Japanese Patent Application Serial No. 2020-149062 filed with Japan Patent Office on Sep. 4, 2020 and Japanese Patent Application Serial No. 2021-011706 filed with Japan Patent Office on Jan. 28, 2021, the entire contents of which are hereby incorporated by reference.

What is claimed is:

1. A light-emitting device comprising:
an anode;
a cathode; and
an EL layer between the anode and the cathode,
wherein the EL layer comprises a light-emitting layer and a hole-transport region,
wherein the hole-transport region is between the anode and the light-emitting layer,
wherein the hole-transport region comprises an organic compound,
wherein the organic compound comprises an arylamine structure, and
wherein when the organic compound is formed into a deposited film, an ordinary refractive index of the deposited film with respect to light with a wavelength of 458 nm is greater than or equal to 1.50 and less than or equal to 1.75, and a birefringence Δn of the deposited film with respect to light with a wavelength of 458 nm is greater than or equal to 0 and less than or equal to 0.008.

2. A light-emitting device comprising:
an anode;
a cathode; and
an EL layer between the anode and the cathode,
wherein the EL layer comprises a light-emitting layer and a hole-transport region,
wherein the hole-transport region is between the anode and the light-emitting layer,
wherein the hole-transport region comprises an organic compound,
wherein the organic compound comprises an arylamine structure, and
wherein when the organic compound is formed into a deposited film, an ordinary refractive index of the deposited film with respect to light with a wavelength of 458 nm is greater than or equal to 1.50 and less than or equal to 1.75, and an alignment order parameter of the deposited film with respect to light with a wavelength corresponding to a longest wavelength where an absorption peak appears in an absorption spectrum is greater than or equal to −0.07 and less than or equal to 0.00.

3. The light-emitting device according to claim 1, wherein a group comprising a para-biphenyl structure is bonded to at least one of nitrogen atoms of amine of the arylamine structure in the organic compound.

4. The light-emitting device according to claim 2, wherein a group comprising a para-biphenyl structure is bonded to at least one of nitrogen atoms of amine of the arylamine structure in the organic compound.

5. A light-emitting device comprising:
an anode;
a cathode; and
an EL layer between the anode and the cathode,
wherein the EL layer comprises a light-emitting layer and a hole-transport region,
wherein the hole-transport region is between the anode and the light-emitting layer,
wherein the hole-transport region comprises an organic compound,
wherein the organic compound comprises an arylamine structure,
wherein when the organic compound is formed into a deposited film, an ordinary refractive index of the deposited film with respect to light with a wavelength of 458 nm is greater than or equal to 1.50 and less than or equal to 1.75, and a birefringence Δn of the deposited film with respect to light with a wavelength of 458 nm is greater than or equal to 0 and less than or equal to 0.04, and
wherein a 1,1'-biphenyl-4-yl group is bonded to a nitrogen atom of amine in the organic compound.

6. A light-emitting device comprising:
an anode;
a cathode; and
an EL layer between the anode and the cathode,
wherein the EL layer comprises a light-emitting layer and a hole-transport region,
wherein the hole-transport region is between the anode and the light-emitting layer,
wherein the hole-transport region comprises an organic compound,
wherein the organic compound comprises an arylamine structure,
wherein when the organic compound is formed into a deposited film, an ordinary refractive index of the deposited film with respect to light with a wavelength of 458 nm is greater than or equal to 1.50 and less than or equal to 1.75, and an alignment order parameter of the deposited film with respect to light with a wavelength corresponding to a longest wavelength where an absorption peak appears in an absorption spectrum is greater than or equal to −0.10 and less than or equal to 0.00, and
wherein a 1,1'-biphenyl-4-yl group is bonded to a nitrogen atom of amine in the organic compound.

7. The light-emitting device according to claim 5, wherein the organic compound comprises at least one of an alkyl group having 3 to 8 carbon atoms and a cycloalkyl group having 6 to 12 carbon atoms in at least one of 2'-, 3'-, 4'-, and 5'-positions in the 1,1'-biphenyl-4-yl group.

8. The light-emitting device according to claim 6, wherein the organic compound comprises at least one of an alkyl group having 3 to 8 carbon atoms and a cycloalkyl group having 6 to 12 carbon atoms in at least one of 2'-, 3'-, 4'-, and 5'-positions in the 1,1'-biphenyl-4-yl group.

9. The light-emitting device according to claim 7, wherein the organic compound comprises a tert-butyl group in the 3'- and 5'-positions in the 1,1'-biphenyl-4-yl group.

10. The light-emitting device according to claim 8, wherein the organic compound comprises a tert-butyl group in the 3'- and 5'-positions in the 1,1'-biphenyl-4-yl group.

11. The light-emitting device according to claim 5, wherein benzene rings in one or a plurality of aniline structures included in the arylamine structure each independently comprise a substituent in a para-position in the organic compound.

12. The light-emitting device according to claim 6, wherein benzene rings in one or a plurality of aniline structures included in the arylamine structure each independently comprise a substituent in a para-position in the organic compound.

13. The light-emitting device according to claim 3, wherein one of benzene rings in a plurality of aniline structures included in the arylamine structure comprises a cyclohexyl group in a para-position in the organic compound.

14. The light-emitting device according to claim 4, wherein one of benzene rings in a plurality of aniline structures included in the arylamine structure comprises a cyclohexyl group in a para-position in the organic compound.

15. The light-emitting device according to claim 11, wherein one of the benzene rings in the plurality of aniline structures included in the arylamine structure comprises a cyclohexyl group in a para-position in the organic compound.

16. The light-emitting device according to claim 12, wherein one of the benzene rings in the plurality of aniline structures included in the arylamine structure comprises a cyclohexyl group in a para-position in the organic compound.

17. The light-emitting device according to claim 3, wherein one of benzene rings in a plurality of aniline structures included in the arylamine structure comprises a phenyl group in an ortho-position in the organic compound.

18. The light-emitting device according to claim 4, wherein one of benzene rings in a plurality of aniline structures included in the arylamine structure comprises a phenyl group in an ortho-position in the organic compound.

19. The light-emitting device according to claim 11, wherein one of the benzene rings in the plurality of aniline structures included in the arylamine structure comprises a phenyl group in an ortho-position in the organic compound.

20. The light-emitting device according to claim 12, wherein one of the benzene rings in the plurality of aniline structures included in the arylamine structure comprises a phenyl group in an ortho-position in the organic compound.

21. The light-emitting device according to claim 1, wherein a fluorenyl group is bonded to a nitrogen atom of amine of the arylamine structure in the organic compound.

22. The light-emitting device according to claim 2, wherein a fluorenyl group is bonded to a nitrogen atom of amine of the arylamine structure in the organic compound.

23. The light-emitting device according to claim 5, wherein a fluorenyl group is bonded to a nitrogen atom of amine of the arylamine structure in the organic compound.

24. The light-emitting device according to claim 6, wherein a fluorenyl group is bonded to a nitrogen atom of amine of the arylamine structure in the organic compound.

25. The light-emitting device according to claim 1, wherein the organic compound is a monoamine compound.

26. The light-emitting device according to claim 2, wherein the organic compound is a monoamine compound.

27. The light-emitting device according to claim 5, wherein the organic compound is a monoamine compound.

28. The light-emitting device according to claim 6, wherein the organic compound is a monoamine compound.

29. The light-emitting device according to claim 1,
wherein the hole-transport region comprises a hole-injection layer and a hole-transport layer,
wherein the hole-injection layer is between the anode and the hole-transport layer, and
wherein the organic compound is included in at least one of the hole-injection layer and the hole-transport layer.

30. The light-emitting device according to claim 2,
wherein the hole-transport region comprises a hole-injection layer and a hole-transport layer,
wherein the hole-injection layer is between the anode and the hole-transport layer, and
wherein the organic compound is included in at least one of the hole-injection layer and the hole-transport layer.

31. The light-emitting device according to claim 5,
wherein the hole-transport region comprises a hole-injection layer and a hole-transport layer,
wherein the hole-injection layer is between the anode and the hole-transport layer, and
wherein the organic compound is included in at least one of the hole-injection layer and the hole-transport layer.

32. The light-emitting device according to claim 6,
wherein the hole-transport region comprises a hole-injection layer and a hole-transport layer,
wherein the hole-injection layer is between the anode and the hole-transport layer, and
wherein the organic compound is included in at least one of the hole-injection layer and the hole-transport layer.

33. The light-emitting device according to claim 29, wherein a substance exhibiting an acceptor property is included in the hole-injection layer.

34. The light-emitting device according to claim 30, wherein a substance exhibiting an acceptor property is included in the hole-injection layer.

35. The light-emitting device according to claim 31, wherein a substance exhibiting an acceptor property is included in the hole-injection layer.

36. The light-emitting device according to claim 32, wherein a substance exhibiting an acceptor property is included in the hole-injection layer.

37. An electronic apparatus comprising:
the light-emitting device according to claim 1; and
a sensor, an operation button, speaker, or a microphone.

38. An electronic apparatus comprising:
the light-emitting device according to claim 2; and
a sensor, an operation button, speaker, or a microphone.

39. An electronic apparatus comprising:
the light-emitting device according to claim 5; and
a sensor, an operation button, speaker, or a microphone.

40. An electronic apparatus comprising:
the light-emitting device according to claim 6; and
a sensor, an operation button, speaker, or a microphone.

41. A light-emitting apparatus comprising:
the light-emitting device according to claim 1; and
a transistor or a substrate.

42. A light-emitting apparatus comprising:
the light-emitting device according to claim 2; and
a transistor or a substrate.

43. A light-emitting apparatus comprising:
the light-emitting device according to claim 5; and
a transistor or a substrate.

44. A light-emitting apparatus comprising:
the light-emitting device according to claim 6; and
a transistor or a substrate.

45. A lighting device comprising:
the light-emitting device according to claim 1; and
a housing.

46. A lighting device comprising:
the light-emitting device according to claim 2; and
a housing.

47. A lighting device comprising:
the light-emitting device according to claim 5; and
a housing.

48. A lighting device comprising:
the light-emitting device according to claim 6; and
a housing.

* * * * *